(12) United States Patent
Morgan et al.

(10) Patent No.: US 7,998,736 B2
(45) Date of Patent: Aug. 16, 2011

(54) ADOPTIVE IMMUNOTHERAPY WITH ENHANCED T LYMPHOCYTE SURVIVAL

(75) Inventors: Richard A. Morgan, Columbia, MD (US); Steven A. Rosenberg, Potomac, MD (US); Cary Hsu, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 682 days.

(21) Appl. No.: 11/576,621

(22) PCT Filed: Oct. 7, 2005

(86) PCT No.: PCT/US2005/036407
§ 371 (c)(1),
(2), (4) Date: May 9, 2007

(87) PCT Pub. No.: WO2007/037780
PCT Pub. Date: Apr. 5, 2007

(65) Prior Publication Data
US 2008/0050341 A1  Feb. 28, 2008

Related U.S. Application Data

(60) Provisional application No. 60/617,768, filed on Oct. 12, 2004, provisional application No. 60/617,340, filed on Oct. 8, 2004.

(51) Int. Cl.
C12N 5/10 (2006.01)
C12N 5/16 (2006.01)
C12N 5/0783 (2006.01)
A61K 48/00 (2006.01)

(52) U.S. Cl. ............... 435/325; 435/372.3; 424/93.21

(58) Field of Classification Search .............. 435/325, 435/372.3; 424/93.21
See application file for complete search history.

(56) References Cited

U.S. PATENT DOCUMENTS

| | | | |
|---|---|---|---|
| 4,965,195 A | | 10/1990 | Namen et al. |
| 6,809,191 B2 * | | 10/2004 | Qiu et al. .................. 536/23.5 |
| 2003/0026790 A1 * | | 2/2003 | Hwu et al. .................. 424/93.21 |

FOREIGN PATENT DOCUMENTS

| | | | |
|---|---|---|---|
| WO | WO 95/27722 | * | 10/1995 |
| WO | WO 98/36768 | * | 8/1998 |
| WO | WO 98/36768 A1 | | 8/1998 |
| WO | WO 2004/034789 A1 | | 4/2004 |
| WO | WO 2004/059556 | * | 7/2004 |
| WO | WO 2004/059556 A2 | | 7/2004 |

OTHER PUBLICATIONS

Kim et al. Human Gene Therapy 5:1457-1466; 1994.*
Klebanoff et al. (Feb. 17, 2004) PNAS, vol. 101(7) 1969-1974.*
Ishimitsu et al. (2001) J. Immunol., vol. 166(3), 1991-2001.*
Marks-Konczalik et al. (2000) PNAS, vol. 97 (21) 11445-11450.*
Bonini et al. (1997) Science, vol. 276, 1719-1724.*
Liu et al. (2001)J. Immunol., vol. 67, 6356-6365.*
Arthur et al., *Cancer Gene Ther.*, 4(1),17-25 (1997).
Bradel-Tretheway et al., *J Virol Meth.*, 111, 145-156 (2003).
Ishimitsu et al., *J. Immunol.*, 166(3), 1991-2001 (2001).
Klebanoff et al., *Proc. Natl. Acad. Sci. U.S.A.*, 101(7),1969-1974 (2004).
Marrack et al., *Ann. Rev. Immunol.*, 22, 765-787 (2004).
Oh et al., *Proc. Natl. Acad. Sci. U.S.A.*, 100(6), 3392-3397 (2003).
Perera et al.,*Proc. Natl. Acad. Sci. U.S.A.*, 98(9),5146-5151 (2001)—online publication on Apr. 10, 2001.
Ramakrishna et al., *J. Virol.*, 78, 9174-9189 (2004).
Schluns et al., *Nature Rev. Immunol.*, 3, 269-279 (2003).
Verhoeyen et al., *Blood*, 101(6), 2167-2174 (2003).
Xin et al., *Vaccine*, 17(7-8),858-866 (1999).
Young et al., *Mol. Cell. Biol.*, 11(2), 854-863 (1991).
Hsu et al., *Journal of Immunology*, 175(11):7226-7234 (Dec. 1, 2005).
Kim et al., *Human Gene Therapy*, 5(12):1457-1466 (Dec. 1994).
Liu et al., *Journal of Immunology*, 167(11):6356-6365 (Dec. 1, 2001).
Hofacker, *Nucleic Acids Research*, 31(13), 3429-3431 (2003).

* cited by examiner

*Primary Examiner* — Anne Marie S Wehbe
(74) *Attorney, Agent, or Firm* — Leydig, Voit & Mayer

(57) ABSTRACT

The invention provides for compositions, e.g., pharmaceutical compositions, comprising a T lymphocyte, or a population thereof, expressing at least one recombinant polynucleotide encoding a cytokine that enhances T lymphocyte survival during the contraction phase of an immune response. The invention further provides an isolated T lymphocyte, or population thereof, expressing at least one recombinant polynucleotide encoding the cytokine, wherein the polynucleotide comprises a non-native coding sequence encoding the cytokine. Also provided is the use of such compositions and T lymphocytes, or populations thereof, for the treatment or prevention of a medical condition e.g., cancer. A method of preparing the a T lymphocyte with enhanced T cell survival is further provided herein.

21 Claims, 31 Drawing Sheets

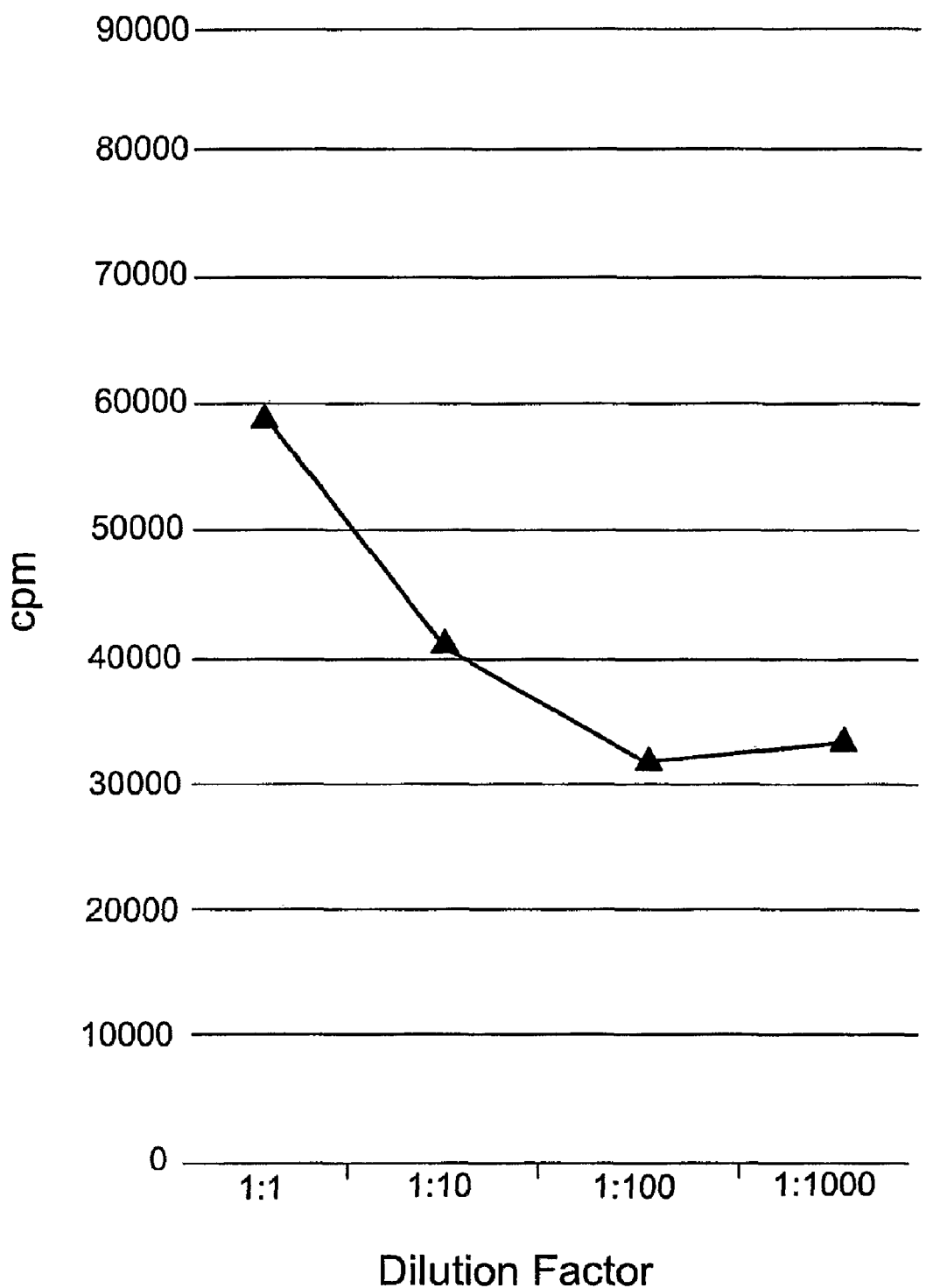

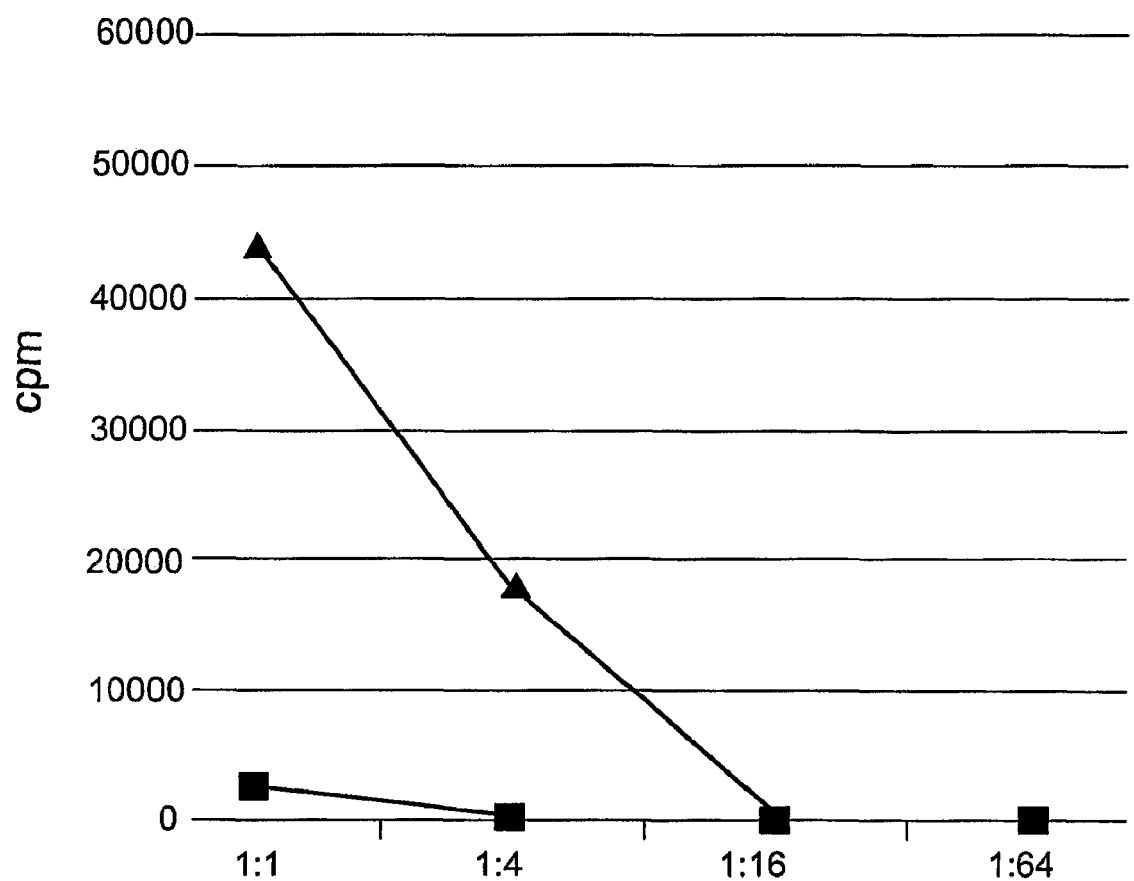

☐ Indicates that alternate codons were substituted

\* Indicates replacement of a wild type codon with usage frequency <20%

SEQUENCE LISTING

<160> NUMBER OF SEQ ID NOS: 10

<210> SEQ ID NO 1
<211> LENGTH: 152
<212> TYPE: PRT
<213> ORGANISM: Homo sapiens

<400> SEQUENCE: 1

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 2
<211> LENGTH: 135
<212> TYPE: PRT
<213> ORGANISM: Homo sapiens

<400> SEQUENCE: 2

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 3
<211> LENGTH: 344

```
<212> TYPE: DNA
<213> ORGANISM: Artificial
<220> FEATURE:
<223> OTHER INFORMATION: Synthetic

<400> SEQUENCE: 3
gtggtctcca ccacgcgtaa ctgggtgaat gtgatcagcg atctgaagaa gatcgaggat      60
ctgatccagt ccatgcacat cgatgccacc ctgtataccg agagcgatgt gcaccccagc    120
tgcaaggtga ccgccatgaa gtgctttctg ctggagctgc aggtgatctc cctggagtcc    180
ggagatgcca gcatccacga taccgtggag aatctgatca tcctggccaa caacagcctg    240
tcctccaatg gcaatgtgac cgagtcggga tgcaaggagt gcgaggagct ggaggagaag    300
aatatcaagg agtttctgca gagctttgta catattgtcc aaat                    344

<210> SEQ ID NO 4
<211> LENGTH: 363
<212> TYPE: DNA
<213> ORGANISM: Artificial
<220> FEATURE:
<223> OTHER INFORMATION: Synthetic

<400> SEQUENCE: 4
gtggtctcca ccacgcgtaa ctgggtgaat gtgatcagcg atctgaagaa gatcgaggat      60
ctgatccagt ccatgcacat cgatgccacc ctgtataccg agagcgatgt gcaccccagc    120
tgcaaggtga ccgccatgaa gtgctttctg ctggagctgc aggtgatctc cctggagtcc    180
ggagatgcca gcatccacga taccgtggag aatctgatca tcctggccaa caacagcctg    240
tcctccaatg gcaatgtgac cgagtcggga tgcaaggagt gcgaggagct ggaggagaag    300
aatatcaagg agtttctgca gagctttgta catattgtcc aaatgttcat caacacttct    360
tga                                                                  363

<210> SEQ ID NO 5
<211> LENGTH: 2116
<212> TYPE: DNA
<213> ORGANISM: Homo sapiens

<400> SEQUENCE: 5
acatccgcgg caacgcctcc ttggtgtcgt ccgcttccaa taaccagct tgcgtcctgc      60 acacttgtgg cttccgtgca cacattaaca actcatggtt ctagctccca gtcgccaagc    120
gttgccaagg cgttgagaga tcatctggga agtcttttac ccagaattgc tttgattcag    180
gccagctggt ttttcctgcg gtgattcgga aattcgcgaa ttcctctggt cctcatccag    240
gtgcgcggga agcaggtgcc caggagagag gggataatga agattccatg ctgatgatcc    300
caaagattga acctgcagac caagcgcaaa gtagaaactg aaagtacact gctggcggat    360
cctacggaag ttatggaaaa ggcaaagcgc agagccacgc cgtagtgtgt gccgccccc    420 ttgggatgga tgaaactgca gtcgcggcgt gggtaagagg aaccagctgc agagatcacc    480
ctgcccaaca cagactcggc aactccgcgg aagaccaggg tcctgggagt gactatgggc    540
ggtgagagct tgctcctgct ccagttgcgg tcatcatgac tacgcccgcc tcccgcagac    600
catgttccat gtttctttta ggtatatctt tggacttcct ccctgatcc ttgttctgtt    660 gccagtagca tcatctgatt gtgatattga aggtaaagat ggcaaacaat atgagagtgt    720
tctaatggtc agcatcgatc aattattgga cagcatgaaa gaaattggta gcaattgcct    780
gaataatgaa tttaactttt ttaaaagaca tatctgtgat gctaataagg aaggtatgtt    840
tttattccgt gctgctcgca gttgaggca atttcttaaa atgaatagca ctggtgattt    900
```

```
tgatctccac ttattaaaag tttcagaagg cacaacaata ctgttgaact gcactggcca    960
ggttaaagga agaaaaccag ctgccctggg tgaagcccaa ccaacaaaga gtttggaaga   1020
aaataaatct ttaaaggaac agaaaaaact gaatgacttg tgtttcctaa agagactatt   1080
acaagagata aaacttgtt ggaataaaat tttgatgggc actaaagaac actgaaaaat   1140
atggagtggc aatatagaaa cacgaacttt agctgcatcc tccaagaatc tatctgctta   1200
tgcagttttt cagagtggaa tgcttcctag aagttactga atgcaccatg gtcaaaacgg   1260
attagggcat ttgagaaatg catattgtat tactagaaga tgaatacaaa caatggaaac   1320
tgaatgctcc agtcaacaaa ctatttctta tatatgtgaa catttatcaa tcagtataat   1380
tctgtactga tttttgtaag acaatccatg taaggtatca gttgcaataa tacttctcaa   1440
acctgtttaa atatttcaag acattaaatc tatgaagtat ataatggttt caaagattca   1500
aaattgacat tgctttactg tcaaaataat tttatggctc actatgaatc tattatactg   1560
tattaagagt gaaaattgtc ttcttctgtg ctggagatgt tttagagtta acaatgatat   1620
atggataatg ccggtgagaa taagagagtc ataaaccttta agtaagcaac agcataacaa   1680
ggtccaagat acctaaaaga gatttcaaga gatttaatta atcatgaatg tgtaacacag   1740
tgccttcaat aaatggtata gcaaatgttt tgacatgaaa aaaggacaat ttcaaaaaaa   1800
taaaataaaa taaaaataaa ttcacctagt ctaaggatgc taaaccttag tactgagtta   1860
cattgtcatt tatatagatt ataacttgtc taaataagtt tgcaatttgg gagatatatt   1920
tttaagataa taatatatgt ttacctttta attaatgaaa tatctgtatt taattttgac   1980
actatatctg tatataaaat attttcatac agcattacaa attgcttact ttggaataca   2040
tttctccttt gataaaataa atgagctatg tattaacaaa aaaaaaaaaa aaaaaaaaa    2100
aaaaaaaaaa aaaaaa                                                   2116

<210> SEQ ID NO 6
<211> LENGTH: 1202
<212> TYPE: DNA
<213> ORGANISM: Homo sapiens

<400> SEQUENCE: 6
tgtccggcgc cccccgggag ggaactgggt ggccgcaccc tcccggctgc ggtggctgtc     60
gccccccacc ctgcagccag gactcgatgg agaatccatt ccaatatatg gccatgtggc    120
tctttggagc aatgttccat catgttccat gctgctgctg acgtcacatg gagcacagaa    180
atcaatgtta gcagatagcc agcccataca agatcgtatt gtattgtagg aggcatcgtg    240
gatggatggc tgctggaaac cccttgccat agccagctct tcttcaatac ttaaggattt    300
accgtggctt tgagtaatga gaatttcgaa accacatttg agaagtattt ccatccagtg    360
ctacttgtgt ttacttctaa acagtcattt tctaactgaa gctggcattc atgtcttcat    420
tttgggctgt ttcagtgcag ggcttcctaa aacagaagcc aactgggtga atgtaataag    480
tgatttgaaa aaaattgaag atcttattca atctatgcat attgatgcta ctttatatac    540
ggaaagtgat gttcaccccca gttgcaaagt aacagcaatg aagtgctttc tcttggagtt    600
acaagttatt tcacttgagt ccggagatgc aagtattcat gatacagtag aaaatctgat    660
catcctagca aacaacagtt tgtcttctaa tgggaatgta acagaatctg gatgcaaaga    720
atgtgaggaa ctggaggaaa aaaatattaa agaattttg cagagttttg tacatattgt    780
ccaaatgttc atcaacactt cttgattgca attgattctt tttaaagtgt ttctgttatt    840
aacaaacatc actctgctgc ttagacataa caaaacactc ggcatttaaa atgtgctgtc    900
```

```
aaaacaagtt tttctgtcaa gaagatgatc agaccttgga tcagatgaac tcttagaaat    960
gaaggcagaa aaatgtcatt gagtaatata gtgactatga acttctctca gacttacttt   1020
actcattttt ttaatttatt attgaaattg tacatatttg tggaataatg taaaatgttg   1080
aataaaaata tgtacaagtg ttgtttttta agttgcactg atattttacc tcttattgca   1140
aaatagcatt tgtttaaggg tgatagtcaa attatgtatt ggtggggctg ggtaccaatg   1200
ct                                                                  1202
```

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7

```
ggggtggacc atcctctaga                                                 20
```

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8

```
accgtcgact gcagaattcg                                                 20
```

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

```
Gly Ile Leu Gly Phe Val Phe Thr Leu
1               5
```

<210> SEQ ID NO 10
<211> LENGTH: 114
<212> TYPE: PRT
<213> ORGANISM: Homo sapiens

<400> SEQUENCE: 10

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80
```

```
Thr Glu Ser Gly Cys Lys Glu Cys Glu Leu Glu Glu Lys Asn Ile
                85              90              95

Lys Glu Phe Leu Gln Ser Phe Val His Ile Val Gln Met Phe Ile Asn
                100             105             110

Thr Ser
```

ADOPTIVE IMMUNOTHERAPY WITH ENHANCED T LYMPHOCYTE SURVIVAL

CROSS-REFERENCE TO RELATED APPLICATIONS

This patent application is a U.S. National Phase of International Patent Application No. PCT/US05/36407, filed Oct. 7, 2005, which claims priority to U.S. Provisional Patent Application No. 60/617,340, filed on Oct. 8, 2004, and U.S. Provisional Patent Application No. 60/617,768, filed on Oct. 12, 2004.

BACKGROUND OF THE INVENTION

This invention pertains to modification of T lymphocytes for therapy, research, and other uses. The T cell modifications enhance T lymphocyte survival.

Adoptive T lymphocyte transfer (adoptive immunotherapy) is the transfer of T lymphocytes to a subject for the therapy of disease. It has great potential for the therapy of a wide variety of diseases including cancer and infectious diseases. Adoptive immunotherapy takes advantage of the immune response, in which the T lymphocyte plays a central role.

The immune response is often thought of as having distinct phases. These phases have been referred to as the initiation, expansion, contraction, and maintenance or memory phases (Schuluns & Lefrancois, *Nature Rev.* 3:269-79 (2003)). After an antigen is recognized, the immune response is "initiated." This is followed by a rapid increase in the number of cells participating in the immune response during the "expansion phase." Without expansion the immune response tends to be ineffective. The next phase, the "contraction phase," controls the size of the immune response to prevent an excessive response that might damage the host. Apoptosis, a specific type of programmed cell death, is an important cellular process during the contraction phase of the immune response. If contraction is excessive, a short-lived and/or weak immune response can result. Finally, for sustained immunity, the immune response must enter the "maintenance phase" and generate "memory T lymphocytes."

An obstacle limiting the efficacy of adoptive immunotherapy is the short-lived survival of the transferred cells. For example, in vitro activation is a step frequently employed in adoptive immunotherapy, but in vitro activated T lymphocytes tend to undergo apoptosis upon in vivo transfer. IL-2 has been given to patients to stimulate their immune response in general, and to augment adoptive immunotherapy. IL-2 does not enhance the survival of T lymphocytes during the contraction stage of the immune response or favor the formation of T lymphocytes, but may be used to prolong or continue the expansion phase. IL-2, however, has significant toxicities when administered to patients and patients cannot always tolerate sufficient amounts of IL-2 required for optimum adoptive immunotherapy. Toxicities associated with high-dose IL-2 include chills, nausea, vomiting, diarrhea, and "capillary-leak syndrome" (which can require intensive care). In addition, patients undergoing high-dose IL-2 therapy frequently also receive prophylactic antibiotic therapy.

The foregoing shows that there is a need to improve adoptive immunotherapy.

The present invention attenuates this need by providing T lymphocytes with enhanced survival during the contraction phase of the immune response, and compositions comprising the same. Advantageously, the invention attenuates the needs in the art by a method that can avoid the toxicity associated with conventional high-dose IL-2 therapy. These and other advantages of the invention, as well as additional inventive features, will be apparent from the description of the invention provided herein.

BRIEF SUMMARY OF THE INVENTION

The invention provides T lymphocytes expressing a recombinant polynucleotide encoding a cytokine that enhances T lymphocyte survival during the contraction phase of the immune response, and compositions, e.g., pharmaceutical compositions, comprising the same. In addition, the invention provides a method of preparing T lymphocytes with enhanced survival, comprising the transformation, e.g., transduction, of T lymphocytes with a recombinant polynucleotide encoding a cytokine that enhances T lymphocyte survival during the contraction and maintenance phases of the immune response. The method can be practiced in vivo, or ex vivo and optionally can further include transferring the transformed, e.g., transduced, cells into a mammal. When the T lymphocytes are transformed, e.g., transduced, ex vivo and transferred to a recipient mammal, the mammal is preferably the same mammal from which the T lymphocytes were obtained (i.e., the T lymphocytes are autologous). The compositions, e.g., pharmaceutical compositions, and methods of the invention can be used in the treatment of a medical condition, e.g., cancer, infectious disease, autoimmune disease, and immunodeficiency. The compositions and methods of the invention also can be used in vitro to modify cell cultures. The compositions and methods of the invention also can be stored and used to provide reagents into which recombinant T cell receptors (TCRs) and other moieties can be transferred, each of which themselves have utility.

The recombinant polynucleotide transformed, e.g., transduced, into the T lymphocytes preferably encodes a functional portion, variant or fusion of IL-7, IL-15, or both IL-7 and IL-15, which of course includes unmodified IL-7 and/or IL-15.

BRIEF DESCRIPTION OF THE SEVERAL VIEWS OF THE DRAWINGS

FIG. 1 illustrates the biological activity of IL-15 expressed by transformed cells, in accordance with an embodiment of the invention. FIG. 1B is a graph of the proliferation of CTLL-2 cells in the presence of different amounts of recombinant human IL-15. FIG. 1C is a graph of the proliferation of CTLL-2 cells in the presence of supernatants of SupT1 cells expressing the MSGIN control vector (♦), MSGV-IL-15 vector (■), or MSGV-Super IL-15 vector (▲).

FIG. 2 is a graph of the cell count (in millions) vs. the days of cytokine withdrawal for untransduced cells (UT (♦)) and cells transduced with a control vector (MSGIN(X)), an IL-2- (▲), IL-7-(■), or IL-15-(●) encoding vector.

FIG. 3 is a graph of the IFN-γ produced in response to exposure to melanoma cells (526 (solid black bar), 624 (solid white bar), 888 (striped bar), and 938 (solid gray bar)) by untransduced cells (NV), L2D8 cells (positive control), or cells transduced with vectors encoding a TCR (TCR), IL-2, IL-7, or IL-15.

FIG. 4 is a graph of the IFN-γ produced by untransduced PBLs (NV), or PBLs transduced with a vector encoding a TCR, IL-2, IL-7, or IL-15, upon exposure to antigen presenting cells pulsed with different concentrations of gp100 peptide (0 to 100 ng/ml).

FIG. 5 is the amino acid sequence of a mature IL-15 protein illustrating codon optimization (SEQ ID NO: 10), in accordance with an embodiment of the invention. The mature protein contains 114 amino acids. Sixty-three codons are replaced with alternate sequences coding for the same amino acid. Nineteen of the substitutions result in a shift from a rarely utilized codon (<20%) to a more frequently utilized codon.

DETAILED DESCRIPTION OF THE INVENTION

Figure 1A:
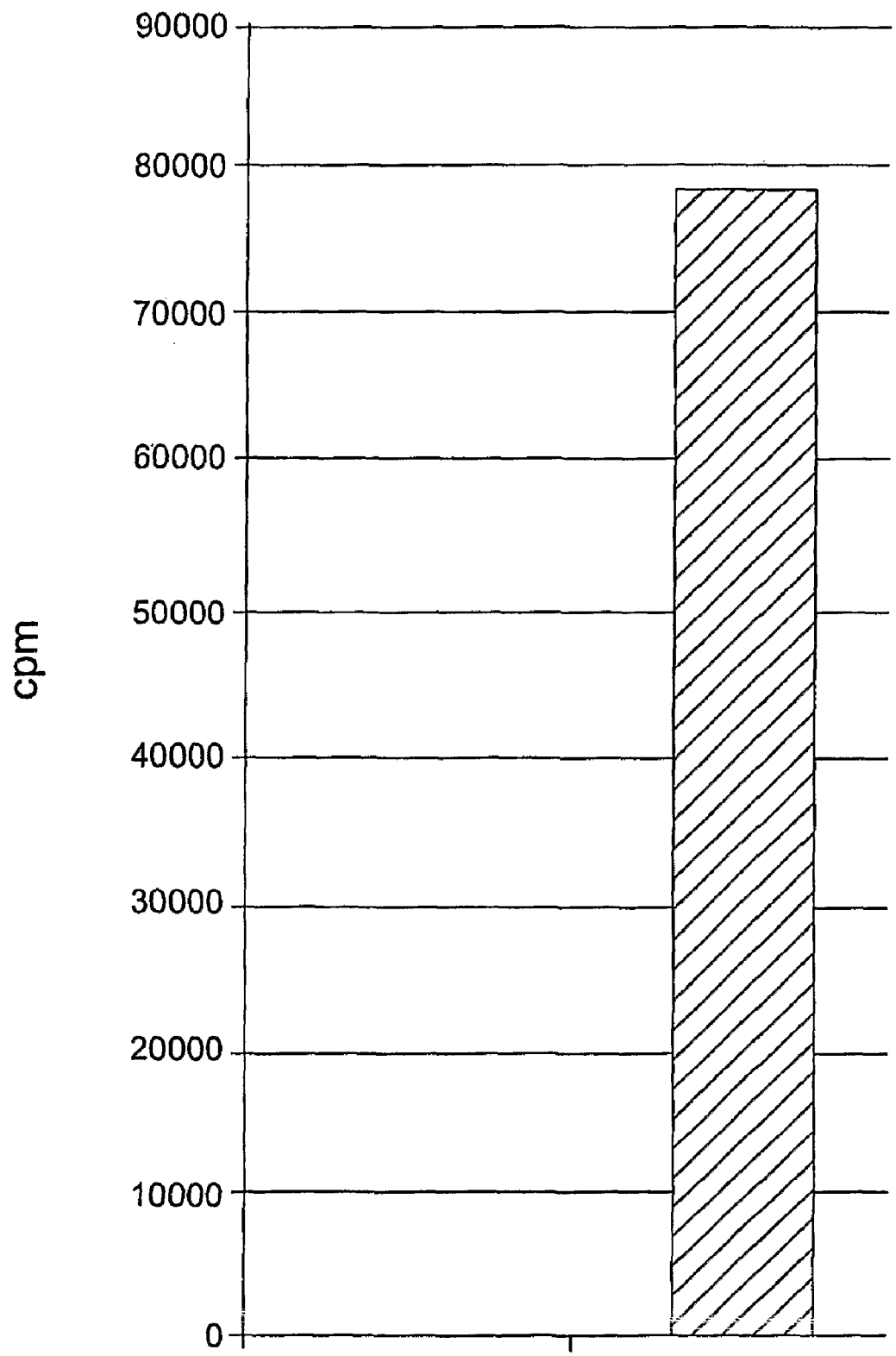
FIG. 1A is a graph of the proliferation of CTLL-2 cells (as determined by the uptake of $^3$H-thymidine) in the absence (left bar) and in the presence (right bar) of IL-2.

The present invention seeks to modulate the contraction and/or maintenance phases of the immune response by providing T lymphocytes having enhanced survival. Thus, the invention seeks to balance cell proliferation and cell death as further described herein.

The present invention provides a T lymphocyte, or a population thereof, as well as compositions, e.g., pharmaceutical compositions, comprising the same. The T lymphocyte of the present invention expresses at least one recombinant polynucleotide encoding at least one cytokine that enhances T lymphocyte survival during the contraction phase of an immune response.

For purposes herein, the T lymphocyte can be any T lymphocyte, such as a cultured T lymphocyte, e.g., a primary T lymphocyte, or a T lymphocyte from a cultured T cell line, e.g., Jurkat, SupT1, etc., or a T lymphocyte obtained from a mammal. If obtained from a mammal, the T lymphocyte can be obtained from numerous sources, including but not limited to blood, bone marrow, lymph node, the thymus, or other tissues or fluids. T lymphocytes can also be enriched for or purified. Preferably, the T lymphocyte is a human T lymphocyte. More preferably, the T lymphocyte is a T lymphocyte isolated from a human. The T lymphocyte can be any type of T lymphocyte and can be of any developmental stage, including but not limited to, CD4$^+$/CD8$^+$ double positive T lymphocytes, CD4$^+$ helper T lymphocytes, e.g., Th$_1$ and Th$_2$ cells, CD8$^+$ T lymphocytes (e.g., cytotoxic T lymphocytes), peripheral blood mononuclear cells (PBMCs), peripheral blood leukocytes (PBLs), tumor infiltrating lymphocytes (TILs), memory T cells, naïve T lymphocytes, and the like. Preferably, the T lymphocyte is a TIL or a PBMC.

The present inventive compositions can comprise a single T lymphocyte or a population thereof. The population of T lymphocytes can be a heterogeneous population comprising the T lymphocyte expressing the recombinant polynucleotide encoding the cytokine, in addition to at least one other cell, e.g., a T lymphocyte, which does not express the recombinant polynucleotide encoding the cytokine, or a cell other than a T lymphocyte, e.g., a B cell, a macrophage, a neutrophil, an erythrocyte, a hepatocyte, an endothelial cell, an epithelial cells, a muscle cell, a brain cell, etc. Alternatively, the population of T lymphocytes can be a substantially homogeneous population, in which the population mainly comprises T lymphocytes expressing the recombinant polynucleotide encoding the cytokine. The population also can be a clonal population of T lymphocytes, in which all T lymphocytes of the population are clones of a single T lymphocyte expressing a recombinant polynucleotide encoding the cytokine, such that all T lymphocytes of the population express the recombinant polynucleotide. In accordance with an embodiment of the invention, a clonal population is preferred.

The T lymphocyte of the present invention or of the present inventive compositions expresses at least one recombinant polynucleotide encoding at least one cytokine, as discussed herein. In other words, the T lymphocyte expresses a cytokine which is encoded by the recombinant polynucleotide. The recombinant polynucleotide can encode more than one cytokine, e.g., two, three, four, five, or more cytokines. For instance, the recombinant polynucleotide can comprise a first recombinant polynucleotide and a second recombinant polynucleotide. In a preferred embodiment, the first recombinant polynucleotide encodes IL-7, or a functional portion, fusion, or variant thereof, and the second recombinant polynucleotide encodes IL-15, or a functional portion, fusion, or variant thereof. Alternatively, the recombinant polynucleotide can comprise more than one copy of the coding sequence which encodes the cytokine, e.g., two copies of the IL-15 gene in tandem.

With respect to the present invention, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication, in vivo replication, or de novo synthesis. The term "polynucleotide" as used herein includes "oligonucleotide," "nucleic acid," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the recombinant polynucleotide does not comprise any insertions, deletions, inversions, and/or substitutions. However, it may be suitable in some instances, as discussed herein, for the recombinant polynucleotide to comprise one or more insertions, deletions, inversions, and/or substitutions.

The recombinant polynucleotides can be constructed based on chemical synthesis and/or enzymatic ligation reactions using procedures known in the art. See, for example, Sambrook et al., *Molecular Cloning: A Laboratory Manual*, 3$^{rd}$ Ed., Cold Spring Harbor Press, Cold Spring Harbor, N.Y. (2001) and Ausubel et al., Current Protocols in Molecular Biology, Greene Publishing Associates and John Wiley & Sons, New York, N.Y. (1994). For example, an oligonucleotide can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the recombinant polynucleotides include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3) w, and 2,6-diaminopurine. Alternatively, one or more of the polynucleotides of the present invention can be purchased from companies, such as Macromolecular Resources (Fort Collins, Colo.) and Synthegen (Houston, Tex.).

The term "isolated" as used herein means having been removed from its natural environment. The polynucleotides of the present invention can alternatively or additionally be purified. The term "purified" as used herein means having been increased in purity, wherein "purity" is a relative term, and not to be necessarily construed as absolute purity. For example, the purity can be at least 50%, can be greater than 60%, 70% or 80%, or can be 100%.

The recombinant polynucleotide can encode any cytokine, provided that the cytokine has the ability to enhance T lymphocyte survival during the contraction phase of an immune response. This enhanced survival during the contraction phase results in a more effective immune response and increased memory T lymphocyte function. It is preferable that the cytokine also facilitates the formation and survival of memory T lymphocytes. Among the suitable cytokines are those that prolong T lymphocyte survival during the contraction phase, such that, for example (but not limited to), when peripheral blood lymphocytes (PBLs) are transformed (e.g., transduced) with the recombinant polynucleotide, the cytokine produced is capable of maintaining at least about 25% of the transduced PBLs viable in vitro for at least 15 days, e.g., when cultured in RPMI 1640, supplemented with 5% normal human serum, in the absence of added cytokines, such as IL-2. Preferably, the cytokine produced maintains at least about 50%, e.g., about 75%, of the transduced PBLs viable in vitro in the absence of added cytokine. More preferably, the cytokine produced maintains 90% or more of the transduced PBLs viable in vitro in the absence of added cytokine. Such cytokines encoded by the recombinant polynucleotide can be, for example, IL-7, IL-15, IL-4, IL-12, IL-21, or IL-23. Preferably, the cytokine is IL-7 or IL-15.

Interleukin-15 (IL-15) is a cytokine involved in T cell development. IL-15 is not normally expressed by T lymphocytes and is normally provided by other cells. Additionally, it is believed that IL-15 is naturally presented to the T lymphocytes on the surface of other cells (i.e., IL-15 is presented to T cells in trans).

The cytokine encoded by the recombinant polynucleotide can comprise the full-length, wildtype cytokine, e.g., wildtype human IL-15 (SEQ ID NO: 6) or wildtype human IL-7 (SEQ ID NO: 5), or a functional portion, functional fusion, or functional variant thereof. By "functional portion," it is meant a fragment or part of the cytokine, e.g., IL-7 or IL-15, which fragment or part retains the biological activity of the cytokine. Functional portions of the cytokine, e.g., IL-7 or IL-15, encompass, for example, those parts of the cytokine that retain the ability to enhance T lymphocyte survival to a similar extent, the same extent, or to a higher extent, as the full-length, wildtype cytokine.

The term "functional fusion" as used herein refers to a fusion protein or chimeric protein comprising a full-length, wildtype cytokine, e.g., IL-7 or IL-15, or a functional portion thereof, fused to another protein or portion thereof. The functional fusion, like the functional portion, retains the biological activity of the cytokine, e.g., the ability to enhance T lymphocyte survival to a similar extent, the same extent, or to a higher extent, as the full-length, wildtype cytokine. The other protein to which the cytokine, or functional portion or variant thereof, is fused can be any protein. Strictly by way of example, the protein can be a marker protein, which facilitates assaying the expression levels of the functional fusion.

The term "functional variant" as used herein is synonomous with "biologically equivalent variant, "biologically equivalent derivative," or "biologically equivalent analog," and refers to a protein comprising the wildtype amino acid sequence of the cytokine, e.g., IL-7 or IL-15, comprising at least one amino acid substitution, deletion, or insertion. The functional variant can comprise, for instance, the wildtype amino acid sequence of IL-7 or IL-15 comprising at least one conservative amino acid substitution.

Functional portions, fusions, or variants of IL-7 and IL-15 also include polypeptides that, when expressed by transformed, e.g., transduced, T lymphocytes, are capable of engaging their respective receptors and initiating signal transduction. Examples of functional portions of IL-7 include polypeptides lacking their wild type signal peptides (Namen et al., U.S. Pat. No. 4,965,195). Additionally, an epitope tag, such as the FLAG tag, may be fused to IL-7 without loss of IL-7 function (Namen et al., U.S. Pat. No. 4,965,195). Furthermore, for example (but not limited to), mutation of the tryptophan at IL-7 amino acid 143 to tyrosine or phenylalanine results in functional variants of IL-7 (vander Speck et al., Cytokine 17:227 (2002)). Portions of the IL-15 coding sequence lacking the sequences of some or all of the putative upstream start codons have been shown to produce functional IL-15 polypeptides. Similarly, fusions of the IL-15 polypeptide with, for example (but not limited to) the CD33 signal peptide or preprolactin leader sequence, produce functional IL-15 polypeptides. In addition, certain amino acids can be mutated without functional effect. For example (but not limited to), it is unlikely that the lysine at amino acid 35 of human IL-15 is important for its function (Pettit et al., J. Bio. Chem. 272:2312-2318 (1997)) and mutations at this position typically still yield a functional IL-15 polypeptide.

Variants of IL-7 and IL-15 that are capable of enhancing T lymphocyte survival can also be readily obtained by substituting an amino acid for an amino acid at a non-essential position of either the IL 7 or IL-15 sequence, or by deleting 1, 2, 3, 4, 4-10, or 11-30 nonessential amino acids. Similarly, 1, 2, 3, 4, 4-10, or 11-30 amino acids can be added in nonessential regions of the polypeptide.

Further, essential amino acids can be replaced by conservative or neutral amino acids. The skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the skilled artisan can readily group synthetic amino acids with naturally-occurring amino acids.

The variant IL-7 or IL-15 of the invention preferably comprises at least about 70% identical amino acids to unmodified IL-7 or IL-15. Also, the polypeptides desirably do not differ in length (i.e., due to deletion mutations) by more than about 10%.

The recombinant polynucleotide can comprise the wild-type, naturally-occurring coding sequence of a cytokine. Alternatively, the recombinant polynucleotide can comprise a non-native coding sequence which encodes the cytokine. By "non-native" is meant that the coding sequence does not occur in nature and is synonomous with "non-natural." The coding sequence can comprise any number of insertions, deletions, and/or substitutions, which substitutions may or may not cause a change in amino acid, e.g., a silent mutation. In some instances, it is preferable for the substitutions to not cause a change in amino acid, i.e., to be a silent mutation.

The non-native coding sequence of the recombinant polynucleotide can be a sequence that has undergone codon optimization, i.e., the non-native coding sequence is a product of codon optimization. Codon optimization is a strategy in which codons within a "rare codons," are changed by in vitro mutagenesis to preferred codons without changing the amino acids of the synthesized protein (Bradel-Tretheway et al., *J Virol Meth* 111: 145-156 (2003); Ramakrishna et al., *J Virol* 78: 9174-9189 (2004)). In addition, the recombinant polynucleotide encoding the cytokine can be further modified, e.g., codon optimized, to improve the folding of the RNA, such that the folding of the RNA transcript encoded by the recombinant polynucleotide is minimized. Without being bound to any particular theory, it is currently believed that the predicted minimized free energy, as determined by, for example, molecular modeling computer programs, correlates with minimized folding of the RNA, which, in turn, facilitates ribosome binding to the RNA and allows efficient expression of the RNA. Preferably, the non-native coding sequence has 90% or less of the predicted free energy of the native coding sequence. In other words, the non-native coding sequence is predicted to have a free energy that is 90% or less the predicted free energy of the native coding sequence. More preferably, the non-native coding sequence has 50% or less of the predicted free energy of the native coding sequence. Most preferable, the non-native coding sequence has 25% or less of the predicted free energy of the native coding sequence.

A given nucleotide sequence can be codon-optimized through the use of publicly-available computer programs, such as "Upgene: A Web-based DNA codon optimization algorithm," available on the internet at the website for the Recombinant Vaccine Center at the University of Pittsburgh Molecular Medicine Institute, and the "Codon Optimizer Tool," which is freeware available on the internet. Alternatively, a nucleotide sequence can be optimized through the services of companies, such as Blue Heron Bio, Inc. (Bothell, Wash.) and GenScript Corp. (Piscataway, N.J.).

For example, the recombinant polynucleotides encoding IL-7, IL-15, portions, fusions or variants thereof, can be modified to have alternative codons. For example, "rare" codons can be replaced by codons more commonly employed in the genome the mammals from which the transformed T lymphocyte is obtained. In this way, the efficiency of expression of the IL-7, IL-15 and/or portions, fusions, or variants thereof can be advantageously modified. Thus, the invention provides a recombinant polynucleotide encoding IL-7 (SEQ ID NO: 1) or IL-15 (SEQ ID NO: 2) with optimized codons expressed in a T lymphocyte to enhance its survival.

A recombinant polynucleotide can be synthesized and used to replace coding sequences of a wild type cytokine gene. For example, SEQ ID NO: 3 is an in vitro synthesized polynucleotide insert, with optimized codons, that is used to replace coding sequence in a recombinant IL-15 polynucleotide. SEQ ID NO: 4 shows, by way of an example and not limitation, a recombinant polynucleotide comprising the sequence of a genetically engineered polynucleotide encoding human IL-15 with specific codons optimized and optimized RNA folding for ribosome entry. Moreover, the inventive recombinant polynucleotides encoding forms of IL-7 or IL-15 or portions, fusions, or variants thereof, include ribonucleic acids, deoxyribonucleic acids, and peptide nucleic acids. In a preferred embodiment of the present invention, the recombinant polynucleotide comprising a non-native coding sequence encoding the cytokine that has undergone codon optimization comprises SEQ ID NO: 3 or SEQ ID NO: 4.

With respect to the present invention, the recombinant polynucleotide can comprise other nucleic acids other than the coding sequence of the cytokine. The recombinant polynucleotide can, for example, comprise a suicide gene, among other genes or expression elements, e.g., promoters, inducers, enhancers, markers, and the like. Preferably, the recombinant polynucleotide comprises a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase. Preferably, the suicide gene is the HSV TK gene. In this case, the agent to which the cell becomes sensitive is the drug ganciclovir.

Without being bound to any particular theory, it is believed that the expression of the cytokine encoded by the recombinant polynucleotide by the T lymphocyte confers upon the present inventive T lymphocyte desirable properties, which render the T lymphocyte especially useful in methods of treating or preventing a medical condition, e.g., a disease, in a human. In this regard, the present invention provides T lymphocytes having such desirable properties, including, for instance, enhanced survival or viability in vitro in the absence of any added or exogenous cytokine in the culture medium. In a preferred embodiment, the T lymphocyte of the present invention has the ability to survive in vitro in the absence of an exogenous or added cytokine, such as IL-2, for at least 20 days. In other words, the T lymphocyte can live for 20 days or more in vitro in a culture medium which lacks any exogenous or added cytokine. More preferably, the T lymphocyte has the ability to survive in vitro in the absence of an exogenous or added cytokine for at least 40 days. Most preferably, the T lymphocyte can survive in vitro in the absence of exogenous or added cytokine for at least 180 days.

The present invention also provides a T lymphocyte that is able to proliferate in the absence of any exogenous or added cytokine, e.g., IL-2. Further, the present invention provides a T lymphocyte that is able to resist IL-2 withdrawal-induced apoptosis in vitro. Furthermore, the present invention provides a T lymphocyte that has the capacity to recognize an antigen in vitro in the absence of an exogenous of added cytokine.

The T lymphocytes, or populations thereof, as well as the compositions comprising the same, have many uses. Preferred uses include the treatment or prevention of a medical condition, e.g., a disease such as cancer, infectious disease, and autoimmune disease, or immunodeficiency. In this respect, the T lymphocytes of the present invention or of the present inventive compositions can comprise other cellular components that aid in the ability of the T lymphocyte to treat or prevent a medical condition. For example, the T lymphocyte can comprise a receptor specific for an antigen of a medical condition. The receptor can be an antigen-specific receptor which recognizes any antigen that is characteristic of the medical condition, e.g., disease, to be treated or prevented, as discussed herein.

The receptor can be the endogenous T cell receptor, i.e., the antigen-specific T cell receptor that is endogenous or native to (naturally-occurring on) the T lymphocyte. In such a case, the T lymphocyte comprising the endogenous T cell receptor can be a T lymphocyte that was isolated from a mammal, which is known to express the particular medical condition-specific antigen. In one preferred embodiment, the mammal can be a mammal that is immunized with an antigen of, or specific for, a medical condition, e.g., a disease. Desirably, the mammal is immunized prior to obtaining the T lymphocytes from the mammal. In this way, the cells transformed with the polynucleotide capable of expressing the cytokine can include cells induced to have specificity for the medical condition to be treated, or can include a higher proportion of cells specific for the medical condition. The T lymphocytes so obtained from the mammal, can then be transformed, e.g., transduced, with the recombinant polynucleotide encoding the cytokine, prepared for re-introduction into a mammal having the medical condition, and re-introduced into the mammal, as discussed hereinafter.

The T lymphocyte comprising the endogenous T cell receptor can be a T cell which was obtained from a mammal already having the medical condition, e.g., disease, to be treated. In this way, the T lymphocytes obtained from the mammal include T lymphocytes having specificity for the antigens, cells, or tissues of the medical condition, e.g., disease (or harboring the etiological agent of a disease). In this embodiment, the T lymphocytes are preferably selected or sorted for the desired specificity and optionally expanded in vitro prior to reintroduction into the same or another mammal.

Alternatively, the T lymphocyte comprising the endogenous T cell receptor can be a T lymphocyte within a mixed population of cells isolated from a mammal, and the mixed population can be exposed to the antigen which is recognized by the endogenous T cell receptor, while being cultured in vitro. In this manner, the T lymphocyte which comprises the receptor that recognizes the medical condition-specific antigen, expands or proliferates in vitro, thereby increasing the number of T lymphocytes having the endogenous antigen-specific receptor.

The receptor which is specific for the medical condition-specific antigen can alternatively be a recombinant chimeric receptor which is specific for an antigen of a medical condition. For example, the receptor can be one that is encoded by a recombinant polynucleotide which is expressed by the T lymphocyte. The recombinant polynucleotide encoding the chimeric receptor can comprise, for example, an antigen-binding portion, such as antigen-binding portions of immunoglobulins (e.g., naturally occurring and synthetic, e.g., genetically engineered, antibodies or portions thereof, scFv, etc.), T cell receptors, B cell receptors, and the like, in addition to another portion that does not function to bind to the antigen. Such chimeric receptors are known in the art (see, for instance, Hwu et al., *JEM* 178: 361-366 (1993); Darcy et al., *J. Immunology* 164: 3705-3712 (2000); Haynes et al., *J Immunology* 166: 182-187 (2001); Dakappagari et al., *Can Res* 60: 3782-3789 (2000); and Weijtens et al., *J Immunology*, 157: 836-843 (1996).

For example, the T lymphocytes transformed, e.g., transduced, by cytokine-encoding recombinant polynucleotide can also be transformed, e.g., transduced, with polynucleotides encoding an exogenous (e.g., recombinant) T cell receptor (TCR) or other recombinant chimeric receptor. Such exogenous chimeric receptors, e.g., chimeric TCRs, can confer specificity for additional antigens to the transformed T lymphocyte beyond the antigens for which the endogenous T cell receptor is naturally specific. This can, but need not, result in the production of T lymphocytes having dual antigen specificities.

Any suitable polynucleotide encoding a chimeric receptor, TCR, or TCR-like protein can be used. TCRs for use in this embodiment are known in the art. For example, polynucleotides encoding TCRs for gp100, NY-ESO-1, and MART-1 have been used in immunotherapy. See, for example, U.S. Pat. No. 5,830,755, Zhao et al., *J Immunology* 174(7):4415-23 (2005); and Hughes et al., *Hum Gene Ther.* 16(4):457-472 (2005). In these embodiments, transformation with the cytokine encoding recombinant polynucleotide can occur before, after, or simultaneously with, T cell receptor transformation. The TCR encoded by the transformed nucleic acids can be of any suitable form including for example, a single-chain TCR or a fusion with other proteins (e.g., without limitation co-stimulatory molecules).

The antigen of a disease which antigen is recognized by the endogenous T cell receptor or recombinant chimeric receptor can be any antigen which is characteristic of a disease or a medical condition. For example, the antigen may be, but is not limited to, a tumor antigen (also termed tumor associated antigen) or a viral antigen. Tumor antigens are known in the art and include, for instance, gp100, MART-1, TRP-1, TRP-2, tyrosinase, NY-ESO-1 (also known as CAG-3), MAGE-1, MAGE-3, etc. Viral antigens are also known in the art and include, for example, any viral protein, e.g., env, gag, pol, gp120, thymidine kinase, and the like.

The disease or medical condition, which is associated with or is characterized by the antigen recognized by the endogenous T cell receptor or chimeric receptor, can be any disease or medical condition. For instance, the disease or medical condition can be a cancer, an infectious disease, an autoimmune disease, or an immunodeficiency, as discussed herein.

For purposes of the present invention, the cancer can be any cancer. As used herein, the term "cancer" is meant any malignant growth or tumor caused by abnormal and uncontrolled cell division that may spread to other parts of the body through the lymphatic system or the blood stream. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor. A specific example of cancer is melanoma.

For purposes herein, "infectious disease" means a disease that can be transmitted from person to person or from organism to organism, and is caused by a microbial agent (e.g., common cold). Infectious diseases are known in the art and include, for example, hepatitis, sexually transmitted diseases (e.g., Chlamydia, gonorrhea), tuberculosis, HIV/AIDS, diphtheria, hepatitis B, hepatitis C, cholera, and influenza.

For purposes herein, "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erytnematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

For purposes herein, "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

The present invention also provides a method of preparing a T lymphocyte with enhanced T cell survival, e.g., a T lymphocyte as described hereinabove. The method comprises contacting a T lymphocyte with a recombinant polynucleotide encoding a cytokine that enhances T lymphocyte survival during the contraction phase of an immune response, such that the contacting leads to the expression of the cytokine by the T lymphocyte.

Any suitable means can be used to contact or transfer the recombinant polynucleotide(s) transferred into the T lymphocytes. Examples of such means include, but are not limited to, the use of a lipid, protein, particle or other molecule capable of facilitating cell transformation with the polynucleotide. The polynucleotide can be carried in a plasmid or a viral vector. Suitable viral vectors include adenoviral, lentiviral, adeno-associated, pox, and herpes viral vectors. Viral vectors are preferably retroviral and derived from a virus that efficiently transduces T lymphocytes.

The T lymphocyte transformation, e.g., transduction, genetically alters the T lymphocytes resulting in the T lymphocytes possessing a recombinant polynucleotide encoding a cytokine that enhances T lymphocyte survival during the contraction phase of the immune response. Although the T lymphocytes are preferably engineered to encode and express such cytokines (i.e., not merely T lymphocytes altered to harbor such cytokine polypeptides), the expression of the cytokines can either be conditionally regulated or constitutive. The genetic alteration can lead to a permanent change in the germline DNA of the T lymphocyte, or it can be a temporary change. In some instances, the inventive genetic alteration is preferably not a permanent change in the germline DNA of the mammal from which the T lymphocyte is derived, unless the genetic alteration occurs in a precursor cell to the T lymphocyte, such as in a hematopoietic stem cell or a lineage restricted T lymphocyte progenitor. The cytokine expressed by the polynucleotide preferably acts on the cell secreting the cytokine and/or co-localized T lymphocytes.

Hematopoietic stem cells can be obtained from, for example (but not limited to), bone marrow, peripheral blood, or cord blood. Furthermore, a population of hematopoietic stem cells optionally can be enriched for by treatment of a mammal with G-CSF infusion or purified with, for example, antibodies such as CD34. Similarly, lineage restricted T lymphocyte precursors may be obtained from tissues such as, but not limited to, thymus by methods known in the art. Additionally, lineage restricted T lymphocyte precursors can be enriched for by treatments, such as but not limited to, thymic stromal lymphopoietin, or purification protocols, such as but not limited to the selection of CD4+/CD8+ cells.

The recombinant polynucleotides used in of the present invention are preferably exogenous to the cells they transform. Additionally, the recombinant polynucleotides of the present invention are preferably "isolated," such that the recombinant polynucleotide is removed from its natural environment or state.

The recombinant polynucleotides described herein preferably comprise a coding region operably linked to a suitable promoter, which promoter is preferably functional in T cells. Viral promoters, such as, without limitation, the major late CMV promoter, the RSV promoter, and the promoter found in the long-terminal repeat of the murine stem cell virus are among the preferred promoters useful in the context of the invention. Suitable non-viral promoters include, but are not limited to, the phosphoglycerokinase (PGK) promoter and the elongation factor 1α promoter. Non-viral promoters are desirably human promoters. Additional suitable genetic elements known in the art can also be ligated to, attached to, or inserted into the inventive nucleic acid and constructs to provide additional functions, level of expression, or pattern of expression. The native promoters for expression of the cytokines genes can also be used in which case they are preferably not used in the chromosome naturally encoding them unless modified by a process that substantially changes that chromosome. Such substantially changed chromosomes can include chromosomes transfected and altered by a retroviral vector or similar process. Alternatively, substantially changed chromosomes can comprise an artificial chromosome such as a HAC, YAC, or BAC.

The recombinant polynucleotides described for the present invention can be inserted into any suitable vector. Suitable vectors include without limitation viral vectors. Suitable viral vectors include, without limitation, retroviral vectors, alphaviral, vaccinial, adenoviral, adenoassociated viral, herpes viral, and fowl pox viral vectors, and preferably have a native or engineered capacity to transform T cells. Additionally, the vectors useful in the context of the invention can be "naked" nucleic acid vectors (i.e., vectors having little or no proteins, sugars, and/or lipids encapsulating them), or complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules. A preferred vector provided by the invention comprises a portion of the murine stem cell virus LTR or a known analog thereof. Vectors further comprising the gag region and env splice site, which is preferably obtained from the vector SFGtcLuc+ITE4-(which are known in the art), are more preferred. These vectors optionally can be used to transfect T lymphocytes in vivo.

Moreover, to optimize the ability of vectors, and particularly viral vectors, to enter the cell by the method of the invention, the method is carried out preferably in the absence of neutralizing antibodies directed against the particular vector being introduced intracellularly, which could impede transduction of target cells. The skilled artisan can routinely test for the presence of such neutralizing antibodies. Techniques are also known in the art to prevent the presence of neutralizing antibodies from impeding effective protein production (see, e.g., International Patent Application Publication No. WO 96/12406).

In another embodiment, the recombinant polynucleotide of the invention encodes two cytokines in a single polypeptide. It is convenient, however, to incorporate nucleic acids encoding portions of two cytokines (or portions, fusions, or variant thereof) into a single vector, in which event each of the two recombinant polynucleotides independently can be in any of the six reading frames, and positioned proximally or distally to each other. When the two recombinant polynucleotides are placed proximal to each other in a vector it is often convenient to drive the expression of both recombinant polynucleotides from a single promoter and to include an internal ribosome entry site (IRES) 5' for the second coding sequences translation. Alternatively, a second promoter, such as a phosphoglycerol kinase (PGK) promoter (Morgan et al., *J. Immunol.*, 171:3287-3295 (2003)) can be used to drive the expression of the second nucleic acid construct.

For purposes of the present inventive method of preparing a T lymphocyte, the T lymphocyte can be contacted with the recombinant polynucleotide in vivo, such as by way of a gene gun, for example. Suitable methods of administering a vector of the invention to a mammal for purposes of gene therapy are known (see, e.g., Rosenfeld et al., *Science* 252: 431-434 (1991); Jaffe et al., *Clin. Res.* 39:302A (1991); Rosenfeld et al., *Clin. Res.* 39:311A (1991); Berkner, *BioTechniques* 6:616-629 (1988); Crystal et al., *Human Gene Ther.* 6:643-666 (1995); Crystal et al., *Human Gene Ther.*, 6:667-703 (1995)). Alternatively, the T lymphocyte can be contacted with the recombinant polynucleotide in vitro or ex vivo. Such methods are within the skill of the artisan. The T lymphocytes are preferably transformed ex vivo by the recombinant polynucleotide.

The transformed cells preferably efficiently express IL-7 and IL-15. For example, without limiting the invention, transformed PBLs express IL-7 such that after 3 days in vitro the cell culture media have IL-7 at concentration of at least 30 pg/ml, more preferably 100 pg/ml, even more preferably 500 pg/ml or the equivalent function when the cytokine is an IL-7 variant. Similarly, for example (and without limiting the invention), the transformed PBLs preferably express IL-15 such that after 3 days in vitro the cell culture media have IL-15 at a concentration of at least 30 pg/ml, more preferably 100 pg/ml, even more preferably 500 pg/ml, or the equivalent function when the cytokine is an IL-15 variant. Although there is no theoretical maximum attainable expression level from transformed cells, expression above 50,000 pg/ml would not normally be necessary for either IL-7 or IL-15.

For purposes of the present inventive method of preparing a T lymphocyte with enhanced T cell survival, the cytokine, recombinant polynucleotide, T lymphocyte can be any of those described herein.

The present invention also provides any of the T lymphocytes, or a population thereof, that are prepared by the present inventive method of preparing a T lymphocyte with enhanced cell survival.

Also provided by the present invention is a method of treating a medical condition, e.g., a disease, in a mammal. The method comprises administering to a mammal any of the T lymphocytes described herein, or a population thereof, or a composition comprising any of the T lymphocytes described herein, in an amount effective to treat the medical condition in the mammal.

The present invention further provides a method of preventing a medical condition, e.g., a disease, in a mammal. The method comprises administering to a mammal any of the T lymphocytes described herein, or a population thereof, or a composition comprising any of the T lymphocytes described herein, in an amount effective to prevent the medical condition in the mammal.

In the treatment or prevention of a medical condition, e.g., a disease, in a mammal, the T lymphocytes that have been transformed, e.g., transduced, with a recombinant polynucleotide encoding and expressing a cytokine can be transferred into the same mammal from which T lymphocytes were obtained. In other words, the T lymphocyte used in the present inventive method of treating or preventing can be an autologous T lymphocyte, i.e., can be obtained from the mammal in which the medical condition is treated or prevented. Alternatively, the T lymphocytes can be transferred into another mammal, although, in most cases, it is preferable for the T lymphocyte to be autologous to the mammal.

In the instance that the T lymphocytes are autologous to the mammal, the mammal can be immunologically naïve, immunized, diseased, or in another condition prior to collection of T lymphocytes from the mammal. In some instances, it is preferable for the method to comprise immunizing the mammal with an antigen of the medical condition prior to obtaining the T lymphocytes from the mammal, transducing the obtained T lymphocytes with the recombinant polynucleotide, and the administering of the T lymphocyte or a composition thereof. As discussed herein, immunization of the mammal with the antigen of medical condition will allow the population of T lymphocytes having an endogenous T cell receptor reactive with the medical condition-specific antigen to increase in numbers, which will increase the likelihood that the T lymphocyte obtained for transduction with the recombinant polynucleotide encoding the cytokine will have the endogenous T cell receptor.

In accordance with the invention, a mammal with a medical condition can be therapeutically immunized with an antigen from, or associated with, that medical condition, including immunization via a vaccine. While not desiring to be bound by any particular theory, the vaccine or immunogen is provided to enhance the mammal's immune response to the medical condition antigen present in or on the infectious agent or diseased tissue. Such a therapeutic immunization includes, but is not limited to, the use of recombinant or natural disease proteins, peptides, or analogs thereof, or modified disease peptides, or analogs thereof that can be used as a vaccine therapeutically as part of adoptive immunotherapy. The vaccine or immunogen, can be a cell, cell lysate (e.g., from cells transfected with a recombinant expression vector), a recombinant expression vector, or antigenic protein. Alternatively, the vaccine, or immunogen, can be a partially or substantially purified recombinant disease protein, peptide or analog thereof or modified peptides or analogs thereof. The proteins or peptides may be conjugated with lipoprotein or administered in liposomal form or with adjuvant.

The present inventive method of treating or preventing a medical condition in a mammal can comprise additional steps. For instance, a variety of procedures, as discussed below, can be performed on the T lymphocytes prior to, substantially simultaneously with, or after their isolation from a mammal. Similarly, a variety of procedures can be performed on the T lymphocytes prior to, substantially simultaneously with, or after their transformation with a polynucleotide encoding at least one cytokine enhancing survival of the T lymphocytes during the contraction phase.

In accordance with the invention, it is not required that other cytokines should be contacted to the T lymphocytes or administered to a mammal receiving the transformed T lymphocytes. However, use of other cytokines is preferred in some embodiments. Suitable other cytokines include, without limitation, IL4, IL-12, IL-21, and IL-23. These other cytokines preferably also act to enhance the survival of T lymphocytes during the contraction phase, which can facilitate the formation and survival of memory T lymphocytes. Moreover, a mammal to which the transformed T lymphocytes are administered optionally can also be treated with additional cytokines, antibiotics, and other pharmaceutical agents. One such preferred cytokine is IL-2 which preferably is administered at low dosages. The transformed T lymphocytes may optionally be further transformed with nucleic acids to express other cytokines, which other cytokines can include but are not limited to IL-2 at low levels. These nucleic acids can be engineered to put the additional cytokine's expression under the control of constitutive, regulatable, or temporally-controlled promoters.

In this regard, the present invention provides a method in which IL-2 is administered to the mammal after the administration of the T lymphocyte or composition to the mammal, as well as a method in which no exogenous cytokine is administered to the mammal after administration of the T lymphocyte or composition.

The present inventive method can be performed on mammals for which other treatments of the medical condition have failed or have had less success in treatment through other means. Also, the present inventive method can be performed in conjunction with other treatments of the medical condition. For instance, the method can comprise administering a cancer regimen, e.g., nonmyeloablative chemotherapy, surgery, hormone therapy, and/or radiation, prior to the administration of the T lymphocyte or composition.

The T lymphocytes, which are preferably autologous to the mammal transfused, are preferably stimulated with the antigen of the medical condition, e.g., disease, in vitro prior to, simultaneously with, or after transformation with the cytokine encoding polynucleotide. The T lymphocytes can be stimulated in vitro with the antigen of the medical condition to be treated in any suitable manner. The antigen used to stimulate the cells in vitro is desirably the same antigen used to therapeutically immunize the mammal. In this regard, the present invention further provides a method of treating or preventing as described herein, wherein the method comprising immunizing the mammal with an antigen of the medical condition prior to the administration of the T lymphocyte or compositions.

The T lymphocytes can be expanded in vitro after transformation, e.g., transduction, but prior to transfer or re-introduction into, i.e., administration to, a mammal. Such an in vitro expansion can take advantage of stimulation with the population of lymphocytes by specific activation using one or more pre-selected strong antigens. The preselected, transformed lymphocytes can be cultured for several days. Between days 14 and 21 after transformation, the cells optionally can be screened for specific cytokine release when exposed to disease antigens, preferably in the context of a major histocompatibility complex (MHC). At this time, it may also be desirable to restimulate the lymphocyte population with the strong antigen. Restimulation using a strong antigen is preferably carried out at a similar concentration as used for the initial stimulation for a similar time period. If allogeneic donor cells are used as the strong antigen, restimulation is preferably carried out at a ratio of 0.5:1 to 4:1, more preferably at a ratio of 1:1 to 2:1 (donor:patient). These cells can be directly reintroduced into the patient or can be frozen for future use, i.e., for subsequent administrations to a mammal.

Antigen specific expansion optionally can be supplemented with expansion under conditions that non-specifically stimulate lymphocyte proliferation such as, for example (but not limited to), with anti-CD3 antibody, anti-Tac antibody, PHA, or IL-2 containing media. Advantageously, however, non-specific stimulation is not necessarily required when IL-7 or IL-15 expressing recombinant polynucleotides are transduced into the T lymphocytes.

The T lymphocytes, or populations thereof, of the present invention, can be formed as a composition, such as a pharmaceutical composition comprising a pharmaceutically acceptable carrier, diluent, and excipient. In this regard, the present invention provides a composition, e.g., a pharmaceutical composition, comprising a T lymphocyte, or a population thereof, expressing at least one recombinant polynucleotide encoding a cytokine that enhances T lymphocyte survival during the contraction phase of an immune response, and a pharmaceutically acceptable carrier. Preferably, the composition comprises T lymphocytes transformed with and expressing the recombinant polynucleotide.

Pharmaceutical compositions containing the present inventive T lymphocytes can comprise more than one type of T lymphocyte, e.g., can comprise T lymphocytes expressing two different cytokines that enhance T cell survival. The pharmaceutical composition can alternatively comprise a particular T lymphocyte of the present invention in combination with other pharmaceutically active agents or drugs, such as chemotherapeutic agents e.g., a cancer drug.

The carrier can be any suitable pharmaceutically acceptable carrier. With respect to pharmaceutical compositions, the carrier can be any of those conventionally used and is based on chemico-physical considerations, such as solubility and lack of reactivity with the active compound(s), and by the route of administration. It will be appreciated by one of skill in the art that, in addition to the following described pharmaceutical composition, the T lymphocytes of the present invention can be formulated as inclusion complexes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), e.g., the T lymphocyte, and one which has no detrimental side effects or toxicity under the conditions of use.

The choice of carrier will be determined in part by the T lymphocyte, as well as by the particular method used to administer the T lymphocyte. Accordingly, there are a variety of suitable formulations of the pharmaceutical composition of the present invention. The following formulations for administration are exemplary and are in no way limiting. More than one route can be used to administer the T lymphocyte, and in instances, a particular route can provide a more immediate and more effective response than another route.

A pharmaceutical composition comprising the transformed T lymphocytes can be prepared so that it does not contain living cells other than blood cells and lymphocytes. That is, the composition can be sterile except for the transduced blood cells, lymphocytes, or T cells. Such compositions can be readily prepared by positive and/or negative selection of the desired cells from a population of cells transformed with the inventive recombinant polynucleotides or vectors. Suitable positive selection techniques include bioaffinity separations, which are well known in the art. For example, an antibody specific for a cell surface antigen of a T lymphocyte can be linked to a magnetic bead, incubated with the transduced population, separated therefrom and optionally washed. Another alternative is to use similar antibodies that have been fluorescently conjugated and positively sort for cells with a fluorescence activated cell sorting capable flow cytometer. Similarly, undesired cells can be eliminated from the composition by any suitable technique. Suitable negative selection techniques include immunomagnetic removal of undesired cells, and the use of antibiotics to destroy microbes. Moreover, leukophoresis, other filtration techniques, sterile technique, differential centrifugation, and other conventional methods can be used to produce a composition suitable for administration to a human.

In an embodiment vectors and recombinant polynucleotides can be administered.

The following methods, formulations, and excipients for administering the inventive recombinant polynucleotides, vectors, and cells are merely exemplary and are in no way limiting.

T cells can be found in most locations in the mammalian body. Accordingly, any suitable route of administration can be used. Intravenous administration of cells is preferred when the mammal is human. A particular route can provide a more immediate and more effective reaction than another route. Suitable pharmaceutically acceptable carriers also are well-known to those who are skilled in the art, and are readily available. The choice of carrier will be determined in part by the particular method used to administer the recombinant vector. Accordingly, there is a wide variety of suitable formulations for use in the context of the invention.

Formulations suitable for oral administration of the nucleic acids and vectors can consist of (a) liquid solutions, such as an effective amount of the compound dissolved in diluents, such as water, saline, or orange juice; (b) suspensions in an appropriate liquid; and (c) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients.

Preferred formulations include aqueous and non-aqueous, isotonic sterile injection solutions, which can contain antioxidants, buffers, bacteriostats, and solutes that render the formulation isotonic with blood, and aqueous and non-aqueous sterile suspensions that can include suspending agents, solubilizers, thickening agents, stabilizers, and preservatives. The inventive nucleic acids and vectors can be stored in a freeze-dried (lyophilized) condition requiring only the addition of the sterile liquid excipient, for example (but not limited to), water, for injections, immediately prior to use. Extemporaneous injection solutions and suspensions can be prepared from sterile powders, granules, and tablets of the kind previously described.

The nucleic acids, vectors and cells of the invention can be formulated in unit-dose or multi-dose sealed containers, such as ampules and vials, and can be stored frozen. These nucleic acids, vectors and cells of the invention can be stored in light-resistant packaging, employing for example (but not limited to), colored glass vials or cardboard boxes. Similarly, instructions for use of the compositions, which preferably comply with the regulations of the U.S. Food and Drug Administration, and more preferably also with its European, Japanese and other equivalent agencies, can be included with these compositions. These nucleic acids, vectors and cells of the invention are preferably also free from non-recombinant microbes (including without limitation fungi and mycobacteria) and non-recombinant viruses. Preferably, the instructions suggest the use a certain quantity of one of these compositions (or range of quantities), or suggest administration of the composition to a mammal for research or therapy via a particular route of administration.

Additionally, a cell, and more preferably, a nucleic acid or vector of the invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the invention will vary with the inventive embodiment, the composition employed, the method of administration, and the particular site and organism being treated. However, the dose should be sufficient to provide a therapeutic response.

Any suitable number of transformed T lymphocytes can be administered to a mammal. While a single T lymphocyte is capable of expanding and providing a benefit, it is preferable to administer at least $10^3$, more preferably at least $10^5$, even more preferably at least $10^8$ and optionally $10^{12}$ or more transformed T lymphocytes. One preferred embodiment of the invention comprises administration of from about $10^8$ to about $10^{12}$ transformed T lymphocytes to a human. There is no theoretical upper limit on the number of transformed T lymphocytes that can be administered to a mammal or the number of times that T lymphocytes can be administered to a mammal. The ordinarily skilled artisan will appreciate, however, that the excessive quantities of administered T lymphocytes (e.g., in some embodiments more than $10^{15}$ or $10^{18}$ transformed cells) can exceed the mammal's ability to support them, lead to undesirable clinical sequelae, and unnecessarily increase costs. Similarly, excessive administrations of therapeutic compositions to mammals can lead to undesirable effects such as allergic responses and infection, and so are preferably avoided.

The invention further provides for the transfer or re-introduction of transformed T lymphocytes into mammals without the administration of exogenous cytokines. Similarly, the invention provides for the transfer or re-introduction of transformed T lymphocytes into mammals that undergo low-dose IL-2 therapy and/or nonmyeloablative chemotherapy in conjunction with adoptive immunotherapy. Such low-dose IL-2 therapy in humans includes, for example, treatment with 20,000 to 200,000 IU/kg intravenously one to three times a day for at least 3 doses, preferably at least 9 doses, and up to a maximum of 45, preferably 30, or more preferably 18 doses. A suitable nonmyeloablative chemotherapy-conditioning schedule will induce transient lymphopenia and can consist of, for example, cyclophosphamide (e.g., 15-80 mg/kg per day for 1 to 4 days) followed by fludarabine (10-50 mg/m² per day for at least 1, preferably 2 more preferably at least 3 days up to a maximum of 12, preferably 8, more preferably 5 days).

As used herein, the term "mammal" as used herein refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is further preferred that the mammals are from the order Artiodactyla, including Bovines (cows) and Swines (pigs) or of the order Perssodactyla, including Equines (horses). It is further preferred that the mammals are of the order Primates, Ceboids, or Simoids (monkeys) or of the order Anthropoids (humans and apes). An especially preferred mammal is the human.

The terms "enhance," "treat," and "prevent," as well as words stemming therefrom, as used herein, do not necessarily imply 100% or complete enhancement, treatment, or prevention. Rather, there are varying degrees of enhancement, treatment, or prevention of which one of ordinary skill in the art recognizes as having a potential benefit or therapeutic effect. In this respect, the present inventive methods can provide any amount of enhancement of T cell survival or any degree of treatment or prevention of a disease. In some instances, treatment can encompass the prevention of the medical condition.

The following examples further illustrate the invention but, of course, should not be construed as in any way limiting its scope.

EXAMPLES

The following cell lines were used in certain of the following examples. The cell lines used include the rhabdomyosarcoma line TE 671 (ATCC HTB-139), the highly-transfectable human renal epithelial line 293T (ATCC CRL-11268), the mouse fibroblast line NIH/3T3 (ATCC CRL-1658), the human lymphoid cell line Sup T1 (ATCC CRL-1942), the TAP-deficient lymphoblastoid cell line T2 (Salter et al., *Immunogenetics* 21: 235-246 (1985)), the PG13 gibbon ape leukemia virus-packaging cell line (ATCC CRL-10686), and the human ecotropic packaging cell line Phoenix Eco (kindly provided by G. Nolan, Stanford University, Stanford, Calif.). Cell culture medium consisted of RPMI 1640 (Invitrogen, Carlsbad, Calif.), supplemented with 10% FCS (Invitrogen), 100 U/ml penicillin (Invitrogen), 100 µg/ml Streptomycin (Invitrogen), 2 mM L-glutamine (Invitrogen), and 25 mM HEPES buffer solution (Invitrogen). Cells lines were cultured at 37° C. in a 5% $CO_2$ humidified incubator.

Example 1

This example demonstrates that recombinant polynucleotides with substitution of the IL-15 leader sequence and optimization of IL-15 codons has been used to express IL-15 polypeptide.

In those cells that express endogenous IL-15, expression is tightly regulated at many levels. A number of features of the IL-15 gene have been recognized that could contribute to this regulation. The 5' untranslated region of the endogenous IL-15 mRNA is very long with multiple AUG start codons and endogenous IL-15 polypeptides have unusually long, 48 amino acid signal peptides. In addition, 27% of the IL-15 codons are suboptimal. These factors are thought to contribute to the inefficient expression of IL15 and offer opportunities for inventive improvements.

An IL-15 cDNA, engineered to be downstream of the efficiently secreted preprolactin leader sequence in place of the long IL-15 signal peptide, was cloned into the pMSGV plasmid such that the IL-15 construct was expressed from plasmid retroviral LTR. This construct was named pMSGV-PPL-IL-15. A codon optimized version of the IL-15, "Super IL-15," was manufactured and substituted for the IL-15 coding sequences in pMSGV-PPL-IL-15 to generate the plasmid pMSGV-PPL-Super-IL-15. The Super IL-15 sequence increases the portion of optimized codons from 71% of all codons to 95% of all codons. The unoptimized, PPL-IL-15, and the codon optimized, PPL-Super-IL-15, coding sequences were then subcloned into the eukaryotic expression vector pEF-Neo. The resulting constructs, pEF-PPL-IL-15 and pEF-PPL-Super-IL-15, respectively, expressed the IL-15 coding sequences under the control of a human Elongation Factor-1α promoter.

The pEF-PPL-IL-15 and pEF-PPL-Super-IL-15 were transfected into 293T cells using the Perfectin reagent and IL-15 production determined using a direct ELISA. Both constructs produced detectable IL-15, while a control transfection (GWIZ) produced no detectable IL-15 (Table 1). Repeating the experiment in duplicate using more optimal amounts of DNA further demonstrated similar IL-15 production from 293T cells transfected with either pEF-PPL-IL-15 or pEF-PPL-Super-IL-15 (Table 2). ELISAs were performed at 24, 48, and 72 hours after transfection.

TABLE 1

IL-15 Production by Transfected 293T Cells

| Condition | IL-15 (pg/ml) |
|---|---|
| 24 h 1.0 µg PPL-IL15 | 1,332 |
| 24 h 1.0 µg PPL-Super-IL15 | 1,351 |
| 24 h 1.0 µg GWIZ | 0 |
| 24 h 0.5 µg PPL-IL15 | 3,854 |
| 24 h 0.5 µg PPL-Super-IL15 | 1,585 |
| 24 h 0.5 µg GWIZ | 0 |
| 48 h 1.0 µg PPL-IL15 | 6,484 |
| 48 h 1.0 µg PPL-Super-IL15 | 7,227 |
| 48 h 1.0 µg GWIZ | 0 |
| 48 h 0.5 µg PPL-IL15 | 12,557 |
| 48 h 0.5 µg PPL-Super-IL15 | 5,462 |
| 48 h 0.5 µg GWIZ | 0 |

TABLE 2

Reproducibility of IL-15 Production form Transfected 293T Cells (duplicate transfections).

| Condition | IL-15 (pg/ml) |
|---|---|
| 24 h-293T/PPL-IL15 | 5,500 |
| 24 h-293T/PPL-IL15 | 5,500 |
| 24 h-293T/PPL-Super-IL15 | 4,600 |
| 24 h-293T/PPL-Super-IL15 | 3,200 |
| 48 h-293T/PPL-IL15 | 23,000 |
| 48 h-293T/PPL-IL15 | 19,000 |
| 48 h-293T/PPL-Super-IL15 | 24,000 |
| 48 h-293T/PPL-Super-IL15 | 26,000 |
| 72 h-293T/PPL-IL15 | 44,000 |
| 72 h-293T/PPL-IL15 | 64,300 |
| 72 h-293T/PPL-Super-IL15 | 55,000 |
| 72 h-293T/PPL-Super-IL15 | 50,000 |

These results confirmed the ability of recombinant polynucleotides to encode a cytokine, such as human IL-15, that enhances T lymphocyte survival during the contraction phase of the immune response. Furthermore, these results confirm that such a cytokine can be expressed after the transformation of mammalian cells.

Example 2

This example demonstrates that recombinant polynucleotides with substitution of the IL-15 leader sequence and optimization of IL-15 codons cloned in a retroviral vector have been used to express IL-15 polypeptide.

The pMSGV-PPL-IL-15 plasmid was modified by cloning a woodchuck hepatitis virus postranscriptional regulatory element (WPRE) inframe between the preprolactin leader and the wildtype IL-15 sequences to generate pMSGV-PPL-IL-15-WPRE. In addition, a mutated version of the Super-IL-15 sequence, pMSGV-PPL-Super-IL-15 (clone 11), was generated. The pMSGV based plasmids were transfected into 293T cells using the Perfectin reagent and IL-15 production determined using ELISA at 24 and 48 hours after transfection. Control MGSIN and IL-15 mutated pMSGV-Super-IL-15 (clone 11) transfected cells produced either no or only barely detectable IL-15, while cells transfected with the pMSGV-PPL-IL-15, pMSGV-PPL-IL-15-WPRE, and the unmutated Super-IL-15 construct, pMSGV-PPL-Super-IL-15 (clone 15), produced significant amounts of IL-15.

TABLE 3

IL-15 Production from 293T Transfected with Retroviral Constructs

| Condition | IL-15(pg/ml) |
|---|---|
| 24 h MSGIN | 0 |
| 24 h MSGV-IL15 | 477 |
| 24 h MSGV-IL15-WPRE | 35 |
| 24 h MSGV-Super-IL15 (clone11) | 0 |
| 24 h MSGV-Super-IL15 (clone15) | 475 |
| 48 h MSGIN | 0 |
| 48 h MSGV-IL15 | 472 |
| 48 h MSGV-IL15-WPRE | 205 |
| 48 h MSGV-Super-IL15 (clone11) | 3 |
| 48 h MSGV-Super-IL15 (clone15) | 467 |

These results confirmed the ability of recombinant polynucleotides to be expressed from a retroviral promoter to produce immunoreactive human IL-15. Therefore, a cytokine, such as human IL-15, that enhances T lymphocyte survival during the contraction phase of the immune response can be expressed from a retroviral vector.

Example 3

This example demonstrates that mammalian cells can be transformed with a recombinant polynucleotide to express a cytokine, here IL-15, that enhances the survival of T lymphocytes during the contraction phase of the immune response.

Phoenix Eco cells were transfected with the IL-15 retroviral vectors and began producing retroviral particles. Retroviral supernatant was harvested and transferred to retronectin-coated plates. PG13 cells were then transduced by the retroviral particles attached to these plates. After 5 days in culture the transduced cells produced IL-15 as determined by ELISA. Bulk PG13 cells transduced with either pMSGV-PPL-IL-15 or pMSGV-PPL-Super IL-15 that were shown to produce IL-15 were then used for limiting dilution cloning. These cells were plated in 96-well plates at dilutions of 3, 1, and 0.3 cells/well. After 10-14 days in culture, wells containing single clones were selected. Cell culture media from the 96-well plate was sampled for IL-15 production by ELISA.

Analysis by ELISA revealed that 3/54 (5%) of the PG13/IL-15 clones produced and 49/61 (80%) of the PG13/Super IL-15 clones produced detectable amounts of cytokine. The PG13/SuperIL-15 clones produced considerably larger amounts of IL-15. Twenty four clones were selected for each vector (IL-15 and Super IL-15) and grown in 24 and then 6 well plates. Once the growth was confluent in 6 well plates, the supernatant was collected and frozen and the cells were cryopreserved. Several of the frozen supernatants were then assayed by ELISA and these results are shown in Table 4. Several packaging cell clones produced considerable amounts of IL-15.

TABLE 4

IL-15 Production by Retroviral Producer Clones

| PG13/MSGV-PPL-IL-15 Transductants | | PG13/MSGV-PPL-Super-IL-15 Transductants | |
|---|---|---|---|
| Clone No | IL-15(pg/ml) | Clone No | IL-15(pg/ml) |
| 2 | 0 | 1 | 1,659 |
| 4 | 0 | 2 | 13,079 |
| 5 | 0 | 11 | 7,245 |
| 7 | 1 | 12 | 1,312 |
| 8 | 0 | 15 | 5,624 |
| 9 | 0 | 18 | 2,439 |
| 10 | 1,438 | 19 | 5,973 |
| 11 | 0 | 21 | 3,538 |
| 15 | 1,041 | 23 | 18,746 |
| 17 | 0 | 31 | 1,473 |
| 18 | 0 | 32 | 2,423 |
| 19 | 0 | 36 | 1,820 |
| 23 | 0 | 38 | 14,754 |
| 27 | 0 | 39 | 2,121 |
| 32 | 0 | 47 | 4,640 |
| 48 | 0 | 49 | 5,640 |
| | | 50 | 5,966 |
| | | 52 | 1,087 |
| | | 54 | 3,400 |
| | | 55 | 13,561 |
| | | 56 | 6,345 |
| | | 57 | 5,990 |
| | | 58 | 2,779 |

Thus, this example demonstrates that mammalian cells can be transformed with a recombinant polynucleotide to express a cytokine, here IL-15, that enhances the survival of T lymphocytes during the contraction phase of the immune response.

Example 4

This example demonstrates that T lymphocytes have been transformed with a recombinant polynucleotide encoding a cytokine that enhances T lymphocyte survival during the contraction phase of the immune response and express that cytokine. In this example, retroviral vectors were used to transduce human T lymphocytes with recombinant polynucleotides resulting in the expression of human IL-15.

Sup-T1 is a human lymphoblastic cell line that can be grown in vitro and is receptive to retroviral transduction. Bulk PG13 supernantants were used to transduce Sup-T1 cells with MSGIN control, MSGV-IL15, and MSGV-Super-IL-15 vector supernatants. ELISA was then used to assay for immunoreactive IL-15. While control transductants did not produce significant IL-15, both IL-15 and Super-IL-15 Sup-T1 transductants produces significant quantities of IL-15 (Table 5). The Super-IL-15 transductants produced 10-fold more IL-15 compared to T-cells transduced with the unoptimized PPL-IL-15 polynucleotide.

TABLE 5

ELISA of Sup-T1 cells transduced with bulk viral supernatants

| Retroviral Vector | IL-15 (pg/ml) |
|---|---|
| MSGIN | 2 |
| MSGV-IL15 bulk supernatant | 27 |
| MSGV-Super IL15 supernatant | 344 |

Furthermore, individual transduced Sup-T1 clones were analyzed. Retroviral supernatants, generated with both IL-15 and Super-IL-15 constructs, shown previously by ELISA to produce IL-15, were thawed, serially diluted, and transferred to 24-well retronectin coated plates. Then $5 \times 10^4$ Sup-T1 cells were then transferred to each well of the retrovirus coated plates after thorough washing of each well with PBS. Cell culture media was then assayed for IL-15 production at 3 and 6 days post-transduction. Several clones from each group were selected for more precise examination. Selected clones were brought out of cryopreservation and expanded. Each group was then plated at $4 \times 10^6$ cells/flask in a T175 flask. Cells were grown to near confluence and retroviral supernatant was harvested on two consecutive days. Both sets of retroviral supernatant were serially diluted and applied to retronectin plates and Sup-T1 cells were again transduced. On day 5 of the culture, the Sup-T1 supernatant was harvested and assayed for IL-15 production by ELISA. In each of two replicate experiments, 4/6 transduced Sup-T1 clones where found to produce significant amounts of IL-15. Transduction of Sup-T1 using retrovirus from PG13/MSGV-Super IL-15 clones 2 and 38 led to the highest production of IL-15 (e.g., 1,549 pg/and 705 pg/ml at 1:1 dilutions, respectively.)

This example demonstrates that individual T lymphocytes can be transformed with a recombinant polynucleotide to express a cytokine that enhances the survival of T lymphocytes during the contraction phase of the immune response, here IL-15, and then these individual transformants can be expanded in vitro.

Example 5

This example demonstrates that T lymphocytes can be transformed with a polynucleotide encoding a cytokine that enhances T lymphocyte survival during the contraction phase of the immune response and produce functional cytokine. In this example retroviral vectors were used to transduce human T lymphocytes with recombinant polynucleotides resulting in the expression of functional human IL-15.

CTLL-2 is a C57BL/6 mouse cytotoxic T lymphocyte clone used to assay for "T lymphocyte growth factor." The cells can be stimulated to proliferate by IL-2 or IL-15. The CTLL-2 assay was used to determine whether IL-15 produced by transduced Sup-T1 cells was biologically active.

CTLL-2 cells were grown in culture for 4 days and then harvested and washed twice in PBS and then plated into a 96-well plate, $5 \times 10^3$ cells/well. The CTLL-2 cells were incubated in the absence of cytokines for 4 hours. Supernatants from the transduced Sup-T1 cells were then added to the culture in serial dilutions. Positive controls (IL-2 and IL-15) were also added to other wells. The CTLL-2 cells were cultured for a total of 24 hours; during the final six hours $^3$H-Thymidine was added to each well. The CTLL-2 cells were harvested to a filter and read on a β-counter.

The CTLL-2 cells did not proliferate in the absence of exogenous cytokine, while CTLL-2 cells did proliferate when control IL-2 or IL-15 were added to their media. In addition, supernatants from Sup-T1 cells transduced with GFP did not stimulate proliferation of CTLL-2. However, the addition of supernatants from Sup-T1 cells transduced with IL-15 vectors, particularly from the Super-IL-15 transductants, stimulated proliferation of CTLL-2 (FIG. 1). The left panel of FIG. 1 shows that the CTLL-2 cells used do not proliferate in the absence of cytokine such as IL-2, but are competent to proliferate if exposed to cytokine such as IL-2. The middle panel of FIG. 1 demonstrates that CTLL-2 cells used were responsive to recombinant IL-15. The right panel of FIG. 1 shows the results of the addition of Sup-T1 supernatants. Control, MSGIN, supernatant failed to induce any proliferation. MSGV-IL-15 suprenatant stimulated weak but detectable proliferation and MSGV-Super-IL-15 supernatant stimulated strong proliferation similar to recombinant IL-15.

Therefore, this example demonstrates that retrovirally transduced Sup-T1 cells produce biologically active IL-15. Moreover, this example demonstrates that the inventive recombinant polynucleotide encoding a cytokine that enhances T lymphocyte survival during the contraction phase of the immune response can transform T lymphocytes to produce biologically active cytokine.

Example 6

This example demonstrates that peripheral blood lymphocytes (PBLs) can be a source of transformed T lymphocytes which are transformed with a recombinant polynucleotide to express a cytokine that enhances T lymphocyte survival during the contraction phase of the immune response and produce function cytokine. Specifically, this example demonstrates how PBLs were transduced to produce IL-15.

On Day 0, fresh PBLs were obtained from human subjects and activated with the antibody OKT3. The next day, cells were transduced with retroviral vectors on retronectin coated plates. The transduction was repeated on Day 3. On Day 7, the cells were suspended in fresh media and plated at $1.5 \times 10^6$ cells/well in a 24-well plate. This was followed, on Day 9, by the removal of culture media and assaying for IL-15 production by ELISA. The results of this assay, presented in Table 6, indicated that the PBLs had been transduced with the Super IL-15 vector and produced measurable levels of IL-15.

TABLE 6

IL-15 Production by Transduced/OKT3 Stimulated PBLs

| Group | IL-15 (pg/ml) |
|---|---|
| 24 h PBL/MSGIN | 0 |
| 24 h PBL/MSGV-Super-IL-15 clone 2 | 39 |
| 24 h PBL/MSGV-Super-IL-15 clone 38 | 34 |

TABLE 6-continued

IL-15 Production by Transduced/OKT3 Stimulated PBLs

| Group | IL-15 (pg/ml) |
|---|---|
| 48 h PBL/MSGIN | 0 |
| 48 h PBL/MSGV-Super-L-15 clone 2 | 67 |
| 48 h PBL/MSGV-Super-IL-15 clone 38 | 61 |

Therefore, PBLs transduced with the Super IL-15 vector produce measurable levels of IL-15.

Example 7

This example demonstrates that peripheral blood lymphocytes (PBLs) can be a source of T lymphocytes transformed with a recombinant polynucleotide to express a cytokine that enhances T lymphocyte survival during the contraction phase of the immune response and produce functional cytokine. Specifically, this example demonstrates that PBLs were transduced with either IL-7 or IL-15. Furthermore, the transduced cells had enhanced in vitro survival and maintained their reactivity with tumor antigens.

T-cells do not naturally produce either IL-7 or IL-15. Accordingly, retroviral vectors capable of expressing IL-2, IL-7 and IL-15 were genetically engineered. To produce a vector capable of producing sufficient quantities of IL-15, several changes were made to the IL-15 expression cassette. First the leader sequence of the natural IL-15 was replaced with the more easily processed leader sequence from the preprolactin gene. Next the translation start codon was optimized according to the Kozak consensus sequence, and finally the protein coding sequence was optimized to both replace rare codons with more abundant ones, while at the same time, optimizing the folding of the RNA to minimize free energy and facilitate ribosome binding. This new IL-15 expression vector, Super-IL-15, produces significantly more IL-15 protein than previously reported vectors (see Examples above).

PBMC from patients previously vaccinated with gp100 peptides were transduced to test the three cytokine expression vectors in a side-by-side comparison. The cells were pulsed in vitro with gp100 peptide followed the next day by the addition of IL-2 and then were exposed to the cytokine vectors on days 3 and 4. 6-7 days post-transduction the cells were then assayed for cytokine production after being cultured in the absence of any added cytokine. The transduced PBLs produced the cytokines that they were engineered to express. Table 7 shows cytokine production by vector-transduced PBLs as measured by ELISA ("UT" is untransduced control). Cells were cultured in the presence or absence of OKT3 to stimulate T cell activation and anti-Tac antibody was added to some cultures to block uptake of secreted IL-2. All values were determined after 3 days of culture in the absence of added cytokines, except "Start Media" which represents media from beginning of IL-2 withdrawal.

Figure 2:
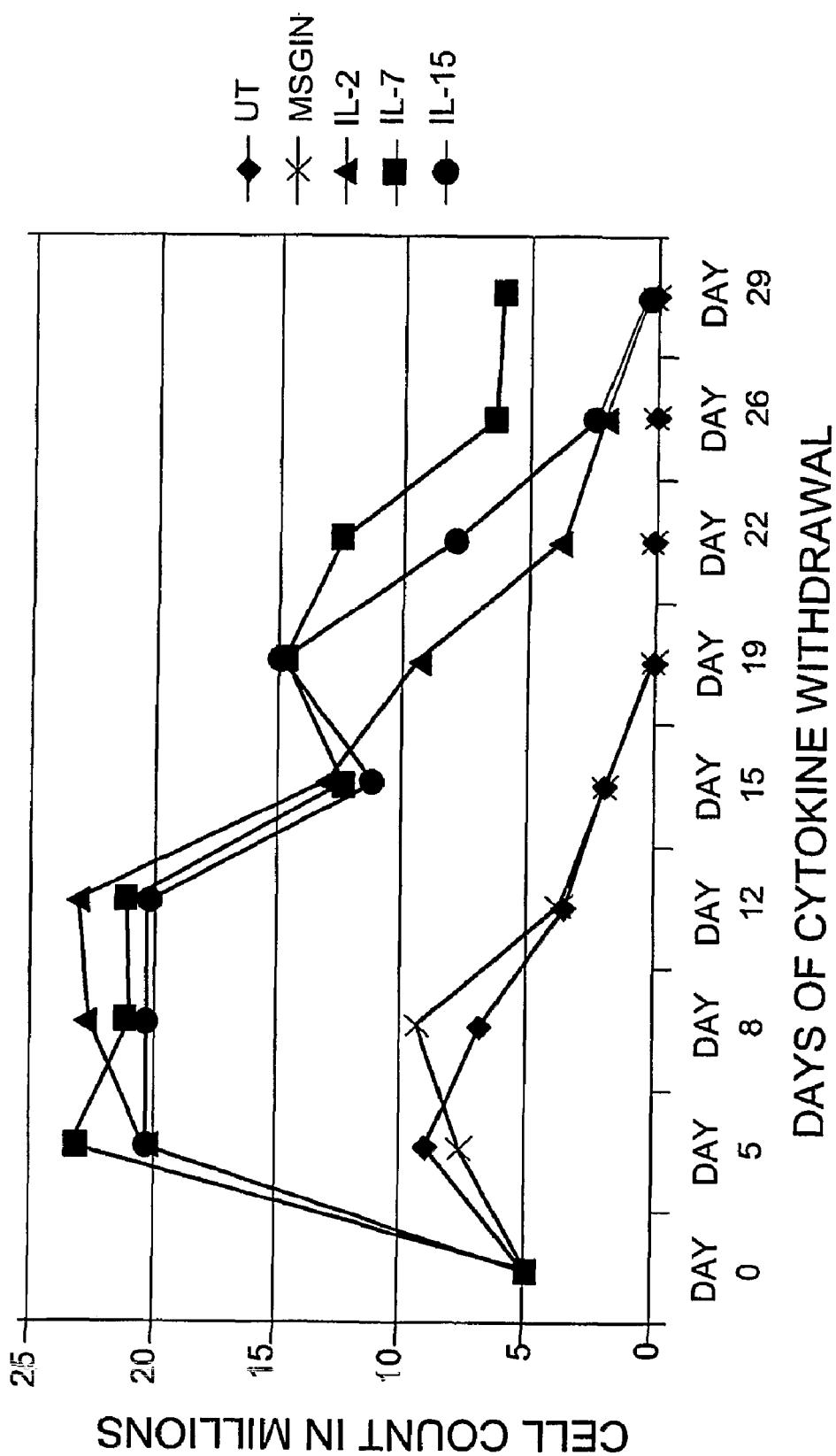
FIG. 2 illustrates the survival of peripheral blood lymphocytes (PBLs) in vitro after cytokine withdrawal, in accordance with an embodiment of the invention. Specifically.

Transduced PBLs were then cultured in medium lacking IL-2 (FIG. 2). Control vector ("MSGIN") and mock-transduced ("UT") cultures quickly lost viability within the first two weeks following withdrawal of IL-2. Cells engineered to produce the different cytokines expanded following cytokine withdrawal and continued to survive for up to four weeks post cytokine withdrawal with greater late survival of the IL-7 and IL-15 engineered cell populations than for the IL-2 engineered cells.

TABLE 7

Cytokine Expression by Transduced Cells

| Added to Media | Added to Media | IL-2 (pg/ml) UT | IL-2 (pg/ml) IL-2 Transduced | IL-15 (pg/ml) UT | IL-15 (pg/ml) IL-15 Transduced | IL-7 (pg/ml) UT | IL-7 (pg/ml) IL-7 Transduced |
|---|---|---|---|---|---|---|---|
| No OKT3 | No Ab | 0.0 | 122.3 | 0.0 | 239.9 | 11.8 | 4069.9 |
| No OKT3 | IgG2a | 0.0 | 188.4 | 25.5 | 232.3 | 6.8 | 3360.2 |
| No OKT3 | Anti-Tac | 0.5 | 191.7 | 0.0 | 246.3 | 6.7 | 3474.0 |
| No OKT3 | Start Media | 0.0 | 2.7 | 0.0 | 0.0 | 7.2 | 141.6 |
| + OKT3 | No Ab | 1.6 | 5103.0 | 0.0 | 1617.0 | 7.6 | 16557.0 |
| + OKT3 | IgG2a | 108.2 | 5999.0 | 0.0 | 2054.0 | 6.9 | 16467.0 |
| + OKT3 | Anti-Tac | 116.5 | 7073.0 | 0.0 | 2146.0 | 6.7 | 14480.0 |
| + OKT3 | Start Media | 0.0 | 252.0 | 0.0 | 36.0 | 7.8 | 152. |

Figure 3:
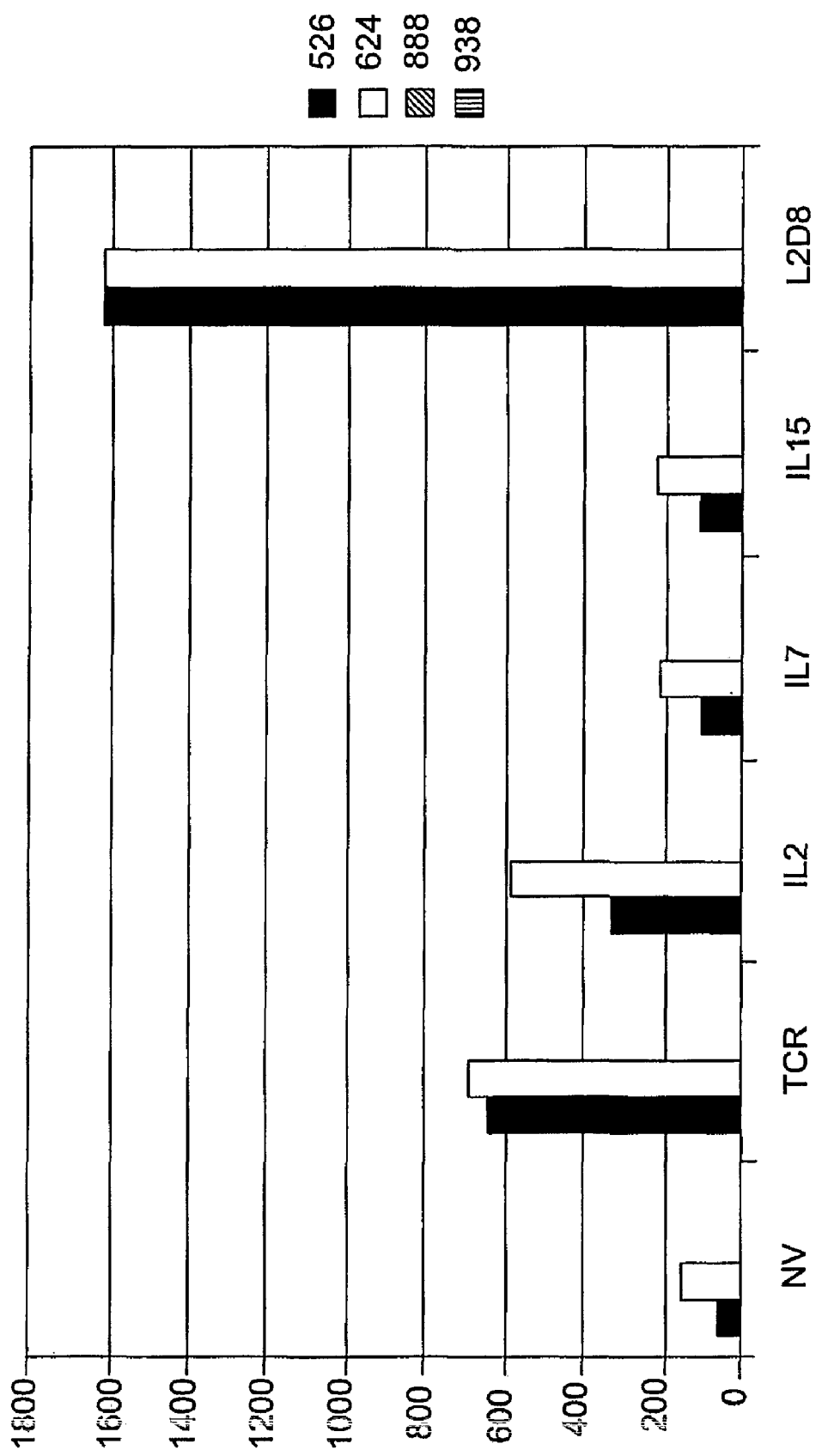
FIG. 3 illustrates interferon gamma production by transformed PBLs when co-cultured with melanoma cells, in accordance with an embodiment of the invention. Specifically.

To determine if the engineered cells retain their ability to recognize the melanoma cells or the gp100 protein, cells were cocultured with gp100 peptide pulsed T2 cells or gp100 expressing melanoma cell lines. T lymphocyte production of gamma interferon was measured by ELISA to determine reactivity. FIG. 3 demonstrates that gp100/HLA-A2 expressing melanoma cell lines were recognized by transduced cells. The melanoma cells lines 526, 624, 888, and 938 all express gp100 but only 526 and 624 express HLA-A2. In FIG. 3 IL-2, IL-7, and IL-15 are cytokine transduced T lymphocytes, L2D8 is an anti-gp100 cytotoxic T lymphocyte clone, TCR is a control transfectant, and NV is an untransduced control.

Figure 4:
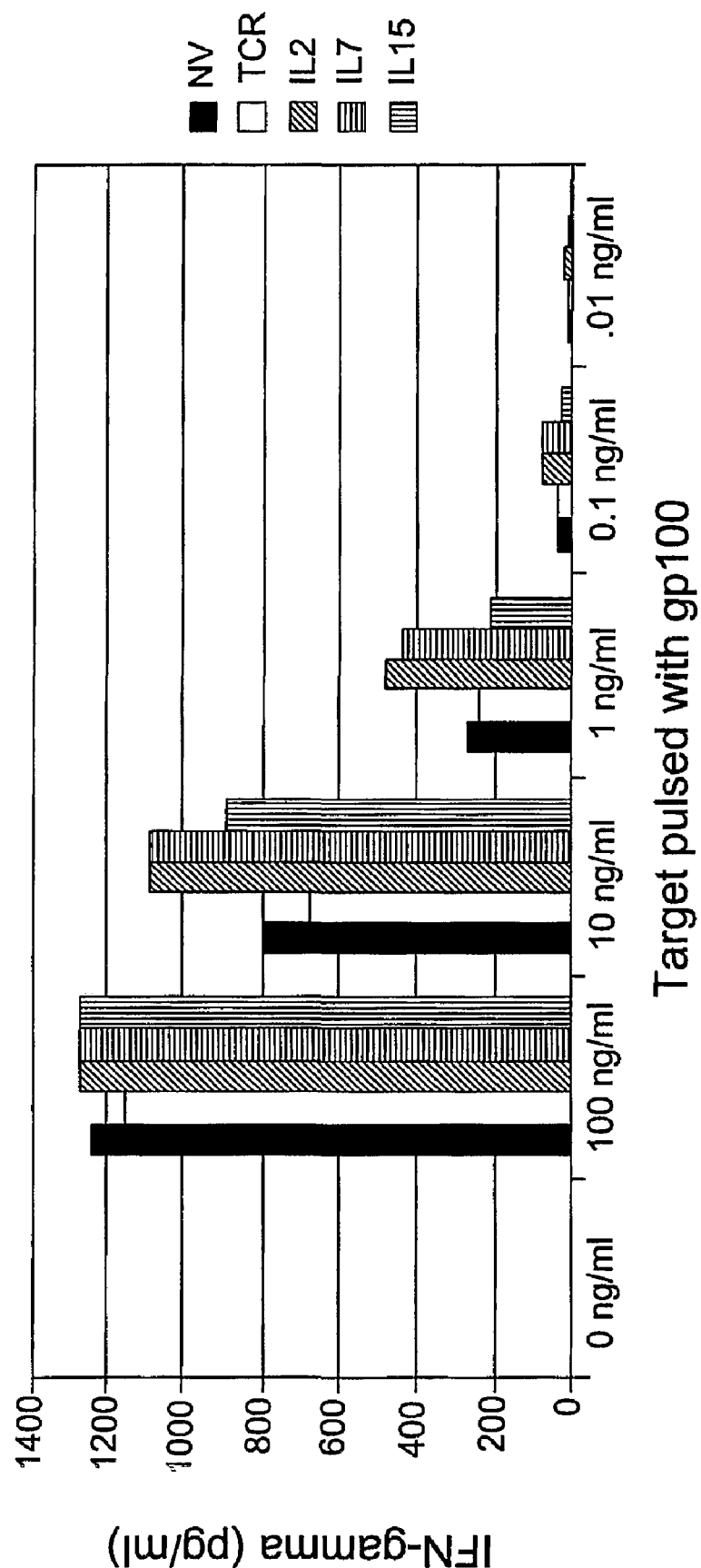
FIG. 4 illustrates interferon gamma production by transformed PBLs when stimulated with antigen (gp100), in accordance with an embodiment of the invention. Specifically.

FIG. 4 demonstrates that all recombinant cytokine polynucleotide transformed cell populations retained the ability to react with T2 cells pulsed with gp100 proteins. This reactivity was measured by interferon gamma production in response to antigen. FIG. 4 further reveals that cytokine transduced PBLs (IL-2, IL-7, and IL-15) produced more interferon when the T2 were pulsed with lower concentrations of gp100 antigen (10 ng/mL, 1 ng/mL) than control PBLs (TCR, vector control; NV, no virus control).

Therefore, this example demonstrates the successful transduction of PBLs with either IL-7 or IL-15 and that the cytokine transduced cells had enhanced in vitro survival and maintained (and even increased) their reactivity with tumor antigens.

Example 8

This example demonstrates the "REP Expansion" of cytokine transformed TILs to therapeutic numbers.

Cytokine transformed TILs are expanded using a single rapid expansion protocol (REP), then retested for activity and specificity according to the protocol as described above in Example 7. Eight days prior to cell harvest and re-infusion, an aliquot of cells is removed for counting and re-assay. Cells are assayed for peptide specificity and tumor recognition by coincubation assay and ELISA as described above. If cell density is greater than $1\times10^6$/mL, cells are split into additional flasks or transferred to Baxter 3 liter culture bags. Then IL-2 is added to 1,000 CU/ml, fungizone is added to 1.25 µg/ml, and cipro is added to 5-10 µg/ml. On day 11, IL-2 is added to REP flasks at 1,000 CU/ml. Cell cultures are split as needed.

On day 14, cells are harvested and either prepared for additional REP cycles or cryopreserved. If cells have grown to sufficient numbers for patient treatment, a sample is collected from each flask for microbiology tests 2-3 days before the beginning of TIL therapy (the test takes 2 days). IL-2 is again added to 1,000 CU/ml on day 14 and every 3 days until the final product is prepared for infusion.

On day 12-20 the final product is prepared for patient infusion. The contents (cells and media) of flasks are transferred to 250 ml centrifuge tubes, while cells in Baxter culture bags are harvested using a Baxter/Fenwal continuous centrifuge cell harvester system. Aliquots are taken from representative bags and pooled for a gram test. Cells are spun to pellet (1,000 rpm, 15 min, about 25° C.) and combined in a single tube, then washed by resuspension in 0.9% (w/v) sodium chloride, followed by centrifugation, and finally resuspended in 45-400 ml of 0.9% sodium chloride. Human albumin (25% w/v) is added to a final concentration of 2.5% (w/v). Aliquots are removed for cell count and viability testing by trypan blue exclusion, and for quality control testing. The final product is infused intravenously as soon as possible.

This example demonstrates how TILs can be prepared and transferred to a patient after transformation with a recombinant polynucleotide encoding a cytokine that enhances T lymphocyte survival during the contraction stage of the immune response.

Example 9

This example demonstrates the generation of wild type and codon-optimized IL-15 vectors.

The construction of retroviral vector plasmids was carried out as follows: pMSGV1 retroviral vector, which contains a murine stem cell virus LTR and RNA processing signals similar to the MFG-class of retroviral vectors, was used as the vector backbone. The detailed construction of this vector was recently described (Hughes et al., *Hum Gene Ther* 16: 457-472 (2005)).

Two retroviral vector plasmids coding for human IL-15 were constructed. pMSGV1 PPL IL-15, which carries the native IL-15 sequence linked to the bovine preprolactin leader sequence (PPL IL-15), was assembled by insertion of an Nco I/BamH I fragment of an IL-15 expression construct (kindly provided by Y. Tagaya, National Institutes of Health, Bethesda, Md.) (Marks-Konczalik et al., *Proc Natl Acad Sci USA* 97: 11445-11450 (2000)) into the Nco I/SnaB I sites of pMSGV1. A codon-optimized IL-15 gene was synthesized in which 63 codon substitutions were made in the mature protein region of the PPL IL-15 sequence (Blue Heron Biotechnology, Bothell, Wash.). These changes in the coding sequence minimized the use of rare codons while maintaining a low free energy as calculated by the Vienna RNA package (Hofacker, *Nucleic Acids Res* 31: 3429-3431 (2003)). This synthetic gene was then subcloned and inserted into the Nco I/SnaB I sites of pMSGV1 to yield pMSGV1 PPL CO IL-15.

The anti-MART-I T-cell receptor retroviral vector, designated AIB, was used for control transductions. This vector also utilizes the pMSGV11 retroviral vector backbone (Hughes et al., *Hum Gene Ther* 16: 457-472 (2005)).

The redundancy of the genetic code is not reflected in a homogeneous distribution of tRNAs for certain amino acids, leading to the potential for "rare codons" in any given cistron. Analysis of the DNA sequence of the mature IL-15 protein revealed that 29 of the 114 codons (25%) were utilized with a frequency of <20% in human genes. In comparison, the IL-2 gene contains 20 rare codons in a coding sequence totaling 133 codons (15%). An alternate IL-15 coding sequence was designed taking into consideration: 1) codon frequency and 2) minimization of nucleic acid folding, as predicted through free energy calculations. The final nucleic acid sequence of the synthetic IL-15 gene includes a total of 63 codon substitutions. 19 of these alternate codons replace native codons with utilization frequencies less than 20%. The amino acid sequence of the optimized IL-15 gene remains identical to the wild type sequence (FIG. 5). The wild type RNA transcript has a predicted free energy of 76 kcal/mol; the codon-optimized molecule has a predicted free energy of 38 kcal/mol. This synthetic gene was subcloned into the wild type IL-15 retroviral vector, replacing the wild type mature protein sequence while leaving the bovine preprolactin leader sequence intact.

Example 10

This example demonstrates that wildtype and codon-optimized IL-15 retroviral vectors have comparable expression in transfected cell lines.

The activity of the vectors pMSGV1 PPL IL-15 and pMSGV1 PPL CO IL-15 was tested by transfecting NIH/3T3, TE671, and 293T cell lines in triplicate with serial dilutions of retroviral vector plasmid DNA. Retroviral transduction was carried out as follows: Non-tissue culture treated 24-well plates (Becton Dickinson Labware, Franklin Lakes, N.J.) were coated with 25 µg/ml of recombinant fibronectin fragment (RetroNectin, Takara, Otsu, Japan). Retroviral vector supernatants were added and the plates were incubated at 32° C. for 2-4° followed by storage at 4° C. overnight. Plates were warmed to room temperature, supernatant was removed, and $0.1-1.0\times10^6$ cells were added to each well with 1 ml of tissue culture medium per well. The plates were then incubated overnight in a 5% $CO_2$ humidified incubator at 37° C. The cytokine production of each cell line was assessed by ELISA.

Figure 6:
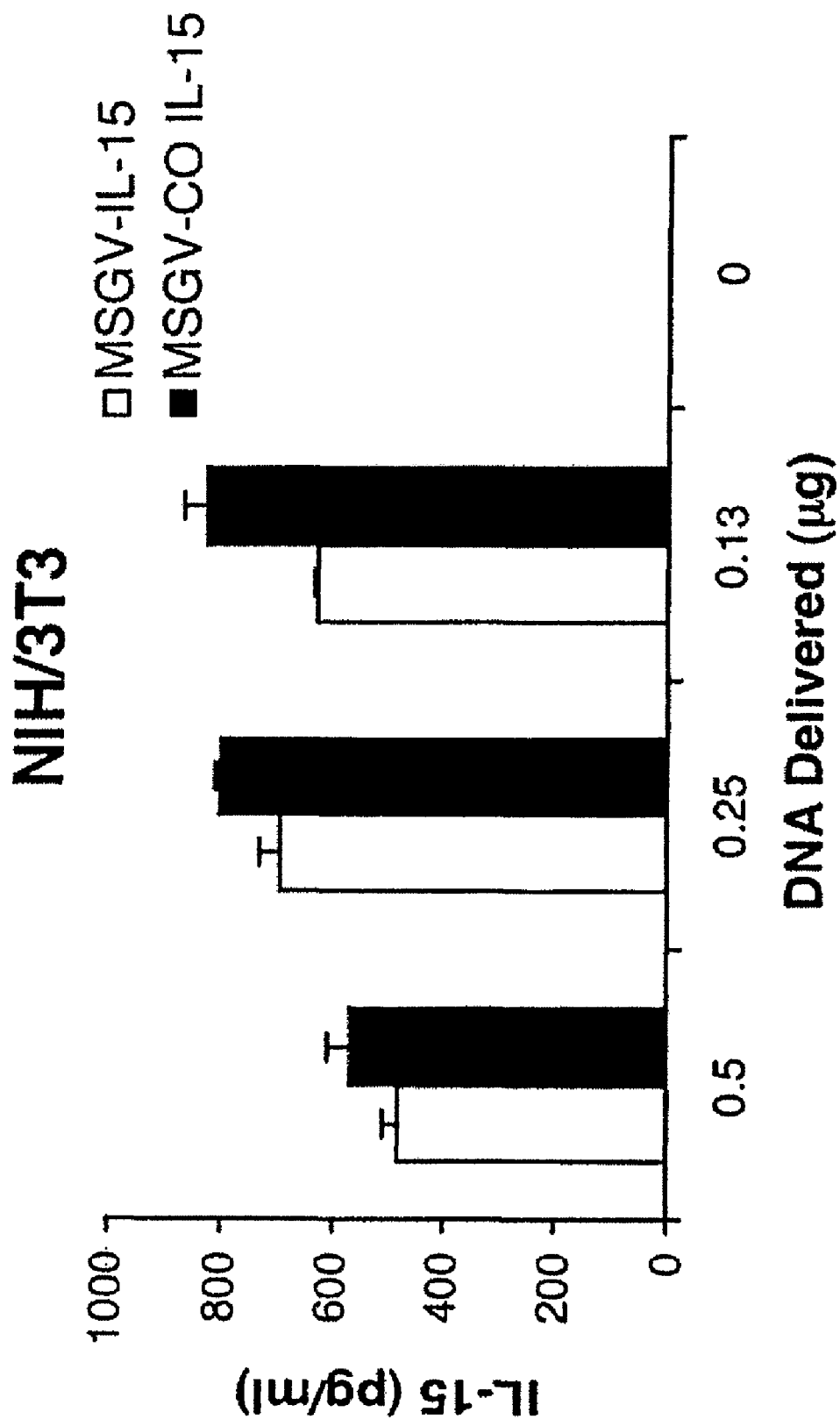
FIG. 6 is a graph of the amount of IL-15 produced by NIH/3T3 cells, in accordance with an embodiment of the invention. NIH3T3 cells were transduced with different amounts of either a vector comprising a wildtype IL-15 gene (MSGV-IL-15; white bars) or a codon optimized (CO) IL-15 gene (MSGV-CO IL-15; black bars). Data are representative or two experiments.
Figure 7:
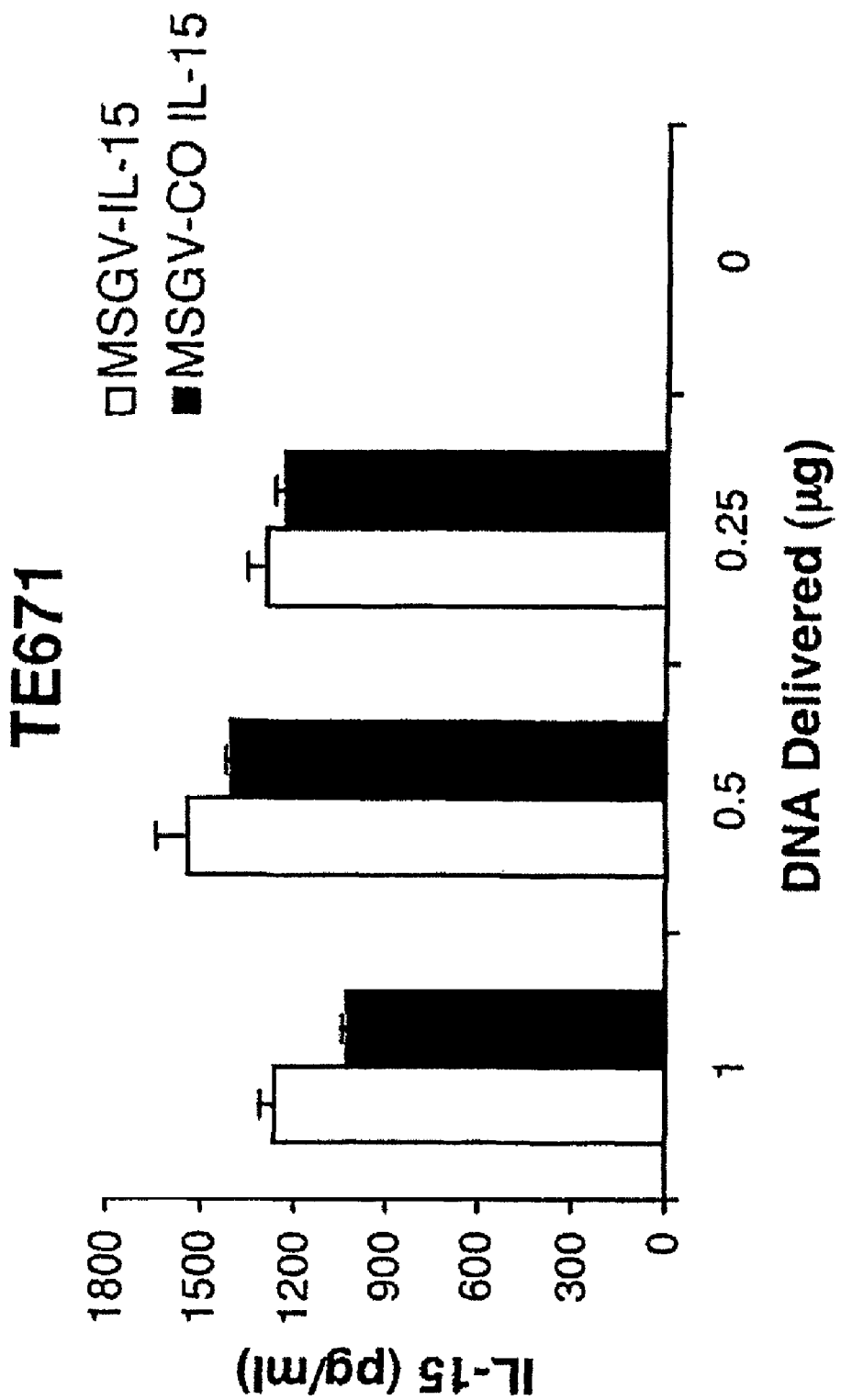
FIG. 7 is a graph of the amount of IL-15 produced by TE671 cells, in accordance with an embodiment of the invention. TE671 cells were transduced with different amounts of either a vector comprising a wildtype IL-15 gene (MSGV-IL-15; white bars) or a codon optimized (CO) IL-15 gene (MSGV-CO IL-15; black bars). Data are representative of two experiments.
Figure 8:
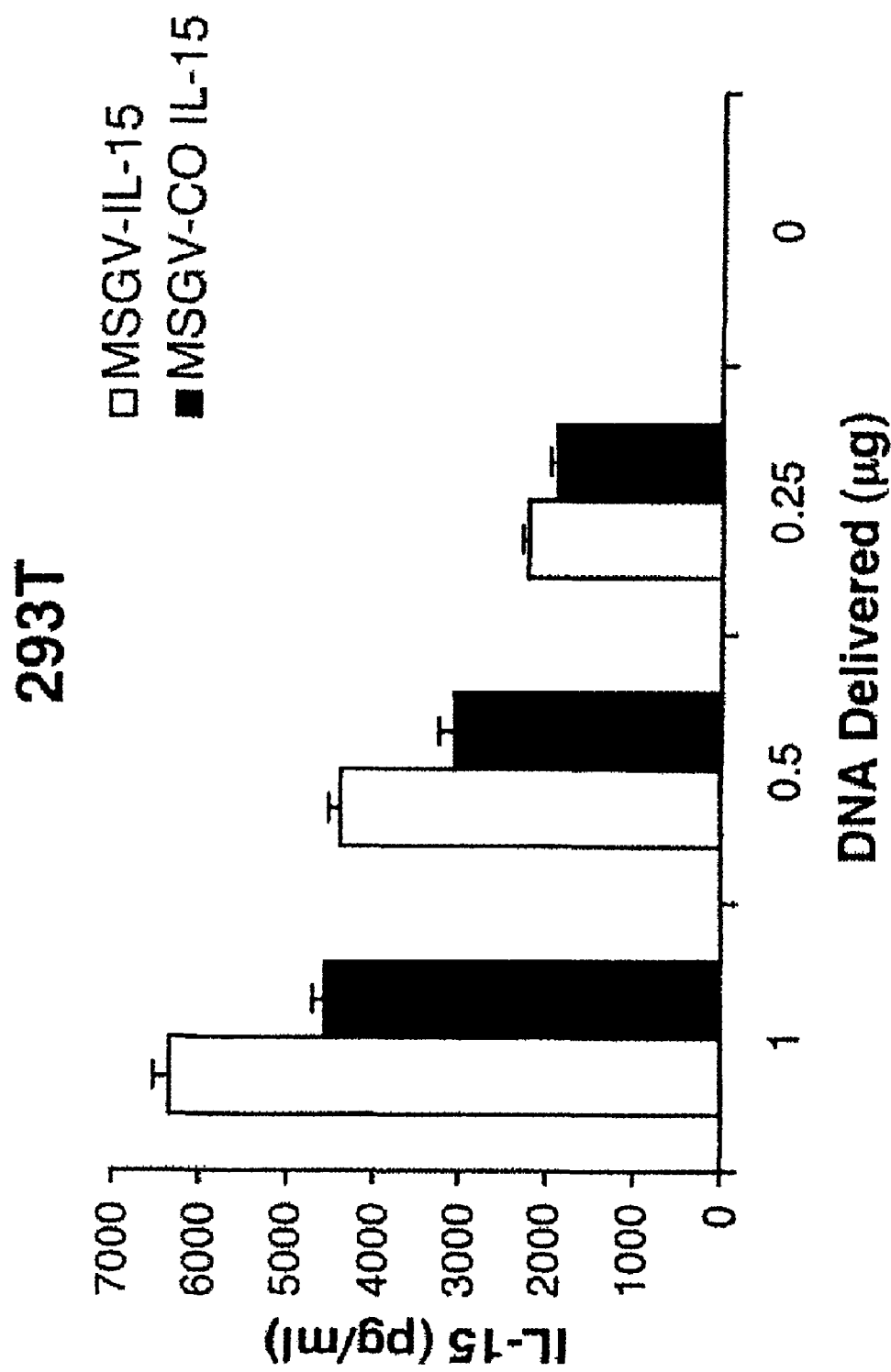
FIG. 8 is a graph of the amount of IL-15 produced by 293T cells, in accordance with an embodiment of the invention. 293T cells were transduced with different amounts of either a vector comprising a wildtype IL-15 gene (MSGV-IL-15; white bars) or a codon optimized (CO) IL-15 gene (MSGV-CO IL-15; black bars). Data are representative of two experiments.

Under all conditions tested and in every cell line, IL-15 was produced at similar levels by cells receiving either the native or codon-optimized vector DNA (FIGS. 6-8).

Example 11

This example demonstrates that codon optimization does not influence the production of retrovirus by packaging cell lines.

To assess whether codon optimization influences the production of retrovirus by packaging cell lines, Phoenix Eco packaging cells were transfected with pMSGV1 PPL IL-15 and pMSGV1 PPL CO IL-15. $5 \times 10^5$ Phoenix Eco packaging cells were plated into each well of a 6-well tissue culture plate. On the following day, the cells were transfected with 2 μg of plasmid DNA from either pMSGV1 PPL IL-15 or pMSGV1 PPL CO IL-15 using the GenePorter2 reagent (Gene Therapy Systems, San Diego, Calif.). 24 h later, the media was aspirated and replaced with 2 ml of fresh media/well. 48 h post-transfection, the performed in triplicate for each plasmid, thus 3 separate preparations of retrovirus were produced from each plasmid.

The generation of high-titer packaging cell clones was carried out as follows: Phoenix Eco packaging cells were transfected with pMSGV1 PPL IL-15 or pMSGV1 PPL CO IL-15 using the GenePorter2 reagent. The retroviral supernatant was harvested 48 h post-transfection and transferred to non-tissue culture plates coated with recombinant fibronectin (Takara). PG13 cells were then transduced on these plates. Clones were isolated by limiting dilution culture and screened for IL-15 production by ELISA (R&D Systems). Retroviral supernatants produced by these clones were then applied to RetroNectin (Takara) coated plates and used to transduce Sup T1 cells. A high-titer clone produced from pMSGV1 PPL CO IL-15 was selected on the basis of IL-15 production by transduced Sup T1 cells. Genomic DNA was then extracted from the selected PG13 clone and a Southern blot was performed in order to verify vector integrity and evaluate the number of integrations. This clone was used to produce retrovirus for all subsequent experiments in which human lymphocytes were transduced.

The resultant retrovirus was titered by Northern dot blot analysis (Onodera et al., *Hum Gene Ther* 8: 1189-1194 (1997)) using a probe common to both vectors. Retroviral supernatants from Phoenix Eco cells transduced with either native or codon-optimized vector contained comparable amounts of RNA (data not shown).

Example 12

This example demonstrates the enhanced IL-15 expression in cells transduced with the codon-optimized retroviral vector.

Retroviral vector preparations described in the previous example were used to transduce NIH/3T3 cells. Retroviral supernatants were used to transduce NIH3T3 cells to assess target cell IL-15 production. 400 μl of undiluted and serially diluted retroviral supernatants were applied to recombinant fibronectin-coated non-tissue culture 24-well plates as described previously. $1 \times 10^5$ NIH/3T3 cells were then transduced in each well of the retrovirus-coated plates. 24 h post transduction, the wells were washed three times with 2 ml PBS (Biofluids, Rockville, Md.) and then filled with 2 ml of fresh medium. The cell culture medium was collected at 72 h post-transduction and the IL-15 content was analyzed by ELISA (R&D Systems, Minneapolis, Minn.).

Figure 9:
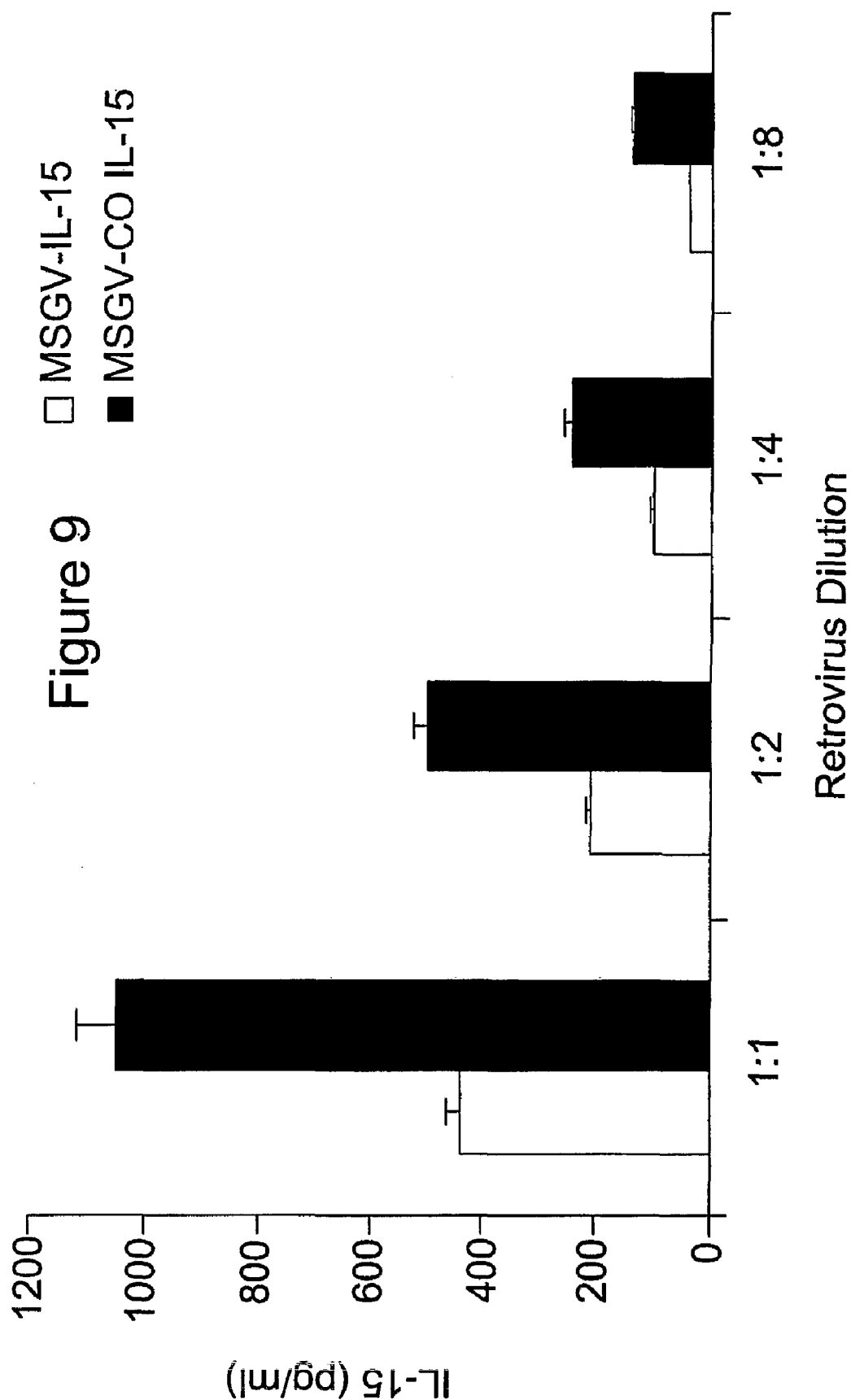
FIG. 9 is a graph of the amount of IL-15 produced by cells transduced with vectors comprising the wildtype (MSGV-IL-15; white bars) or codon optimized (MSGV-CO-IL-15; black bars) IL-15 gene at the indicated retrovirus dilutions, in accordance with an embodiment of the invention.

Twenty four hours after the transduction, the plates were washed to eliminate any trace of IL-15 that could be carried over from the retroviral supernatant. Forty-eight hours later, the cell culture media was collected and assayed for IL-15 (FIG. 9). Cells transduced with a retrovirus coding for GFP did not produce detectable levels of IL-15 (data not shown). The cell culture media from NIH/3T3 transduced with 2-fold serial dilutions of pMSGV1 PPL IL-15 retrovirus contained 436, 205, 98, and 44 pg/ml of IL-15. In contrast, cell culture media from NIH/3T3 transduced with similar dilutions of pMSGV1 PPL CO IL-15 retrovirus contained 1051, 498, 248, and 135 pg/ml of IL-15, an approximately 2.5-fold increase in IL-15 production.

In order to rule out differences in transduction efficiencies of the wild type and codon-optimized IL-15 retroviral vectors, genomic DNA was isolated and analyzed for vector sequences. Using identical oligonucleotide primers, PCR was performed and vector specific amplification was normalized to co-amplified β-actin. PCR amplification utilized genomic DNA extracted from cell lysates using QuickExtract solution (Epicentre, Madison, Wis.). Oligonucleotide primers flanking the multiple cloning site of the pMSGV1 retroviral vector backbone were synthesized: ggggtggaccatcctctaga (SEQ ID NO: 7)+accgtcgactgcagaattcg (SEQ ID NO: 8). Oligonucleotide primers for the amplification of β-actin were also employed. PCR was performed for 30 cycles at 96° C. for 30 s, 60° C. for 30 s, and 72° C. for 90 s in a PTC-200 Thermal Cycler (Global Medical Instrumentation, Ramsey, Minn.). The PCR products were run on a 1% agarose gel and subsequently imaged and quantitated with a LAS-1000 luminescent image analyzer system (Fujifilm Medical Systems USA). The ratio of vector insert band intensity compared to the corresponding β-actin band was calculated for each of the cell lysate samples.

Figure 10:
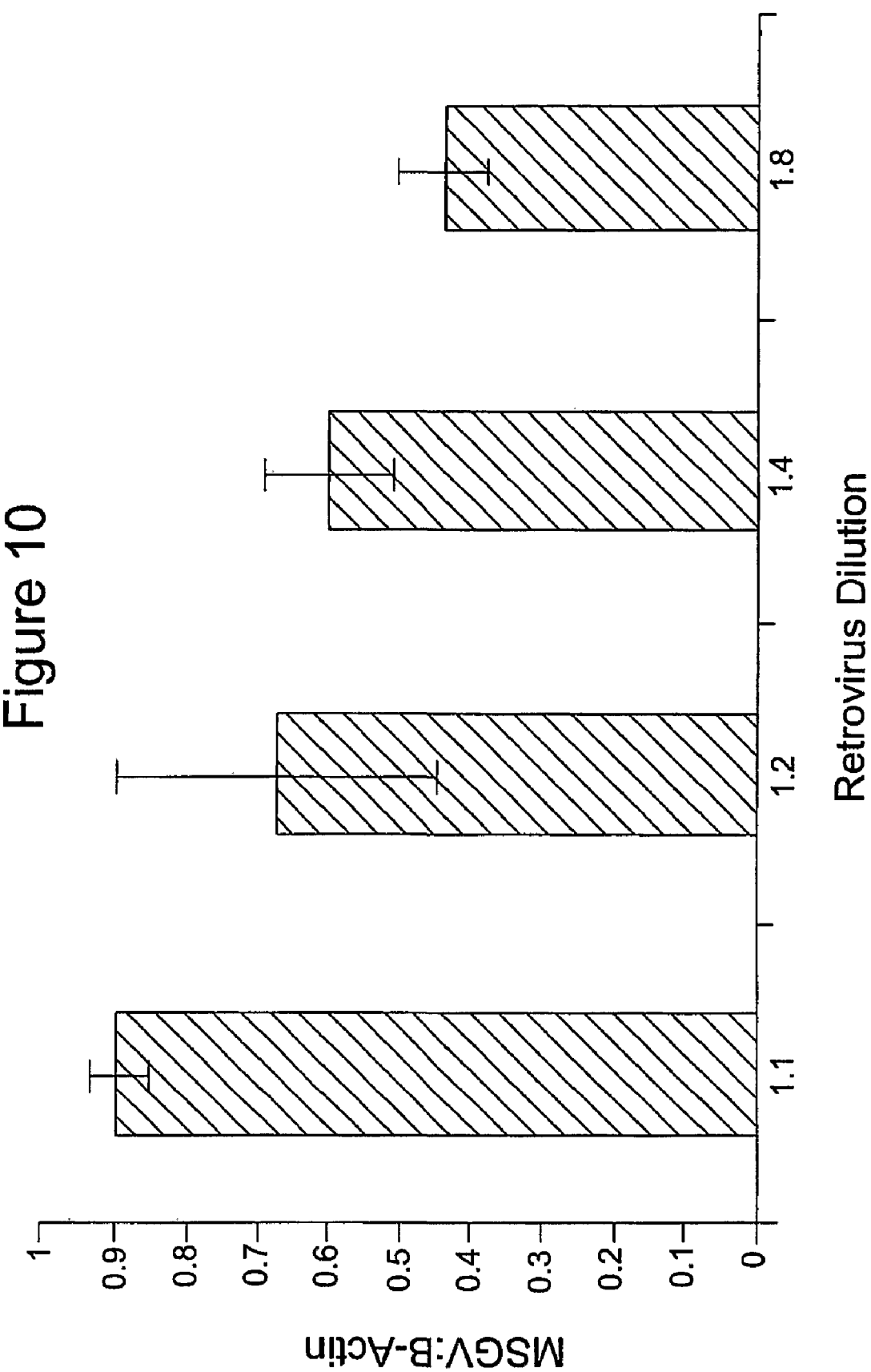
FIG. 10 is a graph of the amount of β-actin DNA detected by PCR from the cells of FIG. 9 transduced with wildtype IL-15 gene-containing vectors, in accordance with an embodiment of the invention.
Figure 11:
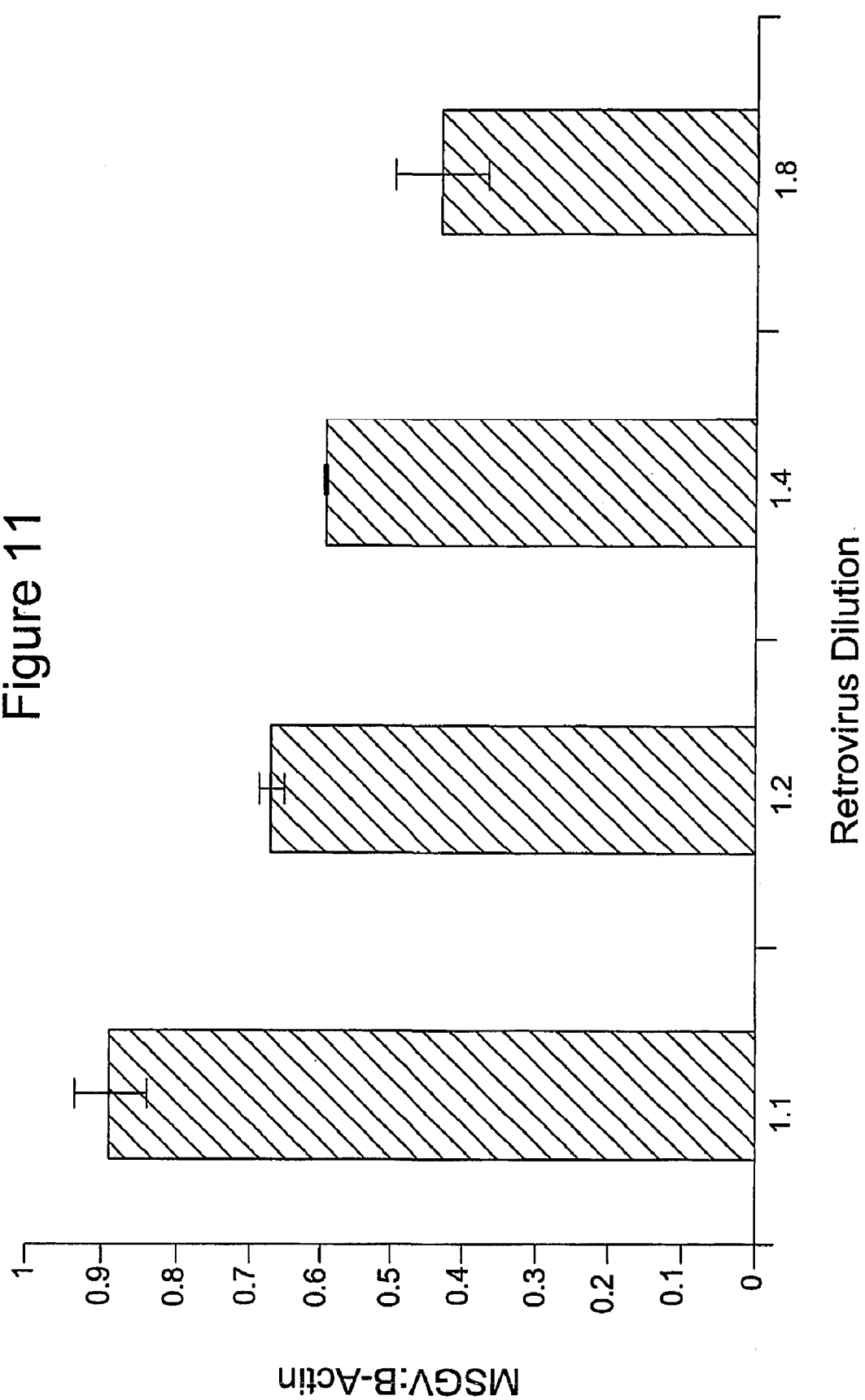
FIG. 11 is a graph of the amount of β-actin DNA detected by PCR from the cells of FIG. 9 transduced with codon optimized IL-15 gene-containing vectors, in accordance with an embodiment of the invention.

As shown in FIGS. 10 and 11 transduction with either the wild-type or codon-optimized retrovirus led to comparable efficiencies of gene transfer.

Example 13

This example demonstrates that IL-15 vector transduction of human PBLs results in stimulation-dependent cytokine production and persistence of the cells in the absence of exogenous cytokine support.

The transduction of PBLs and cytokine withdrawal studies were carried out as follows: PBLs were obtained by leukapheresis from patients with a history of melanoma who were treated on an adjuvant peptide vaccine protocol at the National Cancer Institute. Lymphocytes were purified by centrifugation on a Ficoll/Hypaque cushion, washed in HBSS, and cultured in medium consisting of AIM-V medium (Invitrogen) supplemented with 300 IU/ml IL-2, 5% human AB serum (Valley Biomedical, Winchester, Va.), 100 U/ml penicillin (Invitrogen), 100 μg/ml Streptomycin (Invitrogen), 2 mM L-glutamine (Invitrogen), 55 μM 2-mercaptoethanol, and 25 mM HEPES buffer solution (Invitrogen). Polyclonally-activated lymphocytes were generated by adding 50 ng/ml of OKT3 on culture day 0. Peptide-reactive lymphocytes were generated from PBLs obtained from patients previously vaccinated with the anchor residue modified gp100: 209-217(210M) peptide (20); these PBLs were activated by adding 1 μg/ml of gp100:209-217(210M) to the lymphocyte culture medium, in the absence of IL-2, on day 0. On day 1, 300 IU/mil of IL-2 was added to the cells. Lymphocytes were cultured at 37° C. in a 5% $CO_2$ humidified incubator. OKT3 activated cells were transduced on culture days 2 and 3 while peptide-stimulated cells were transduced between culture days 5 and 7. Each culture was exposed to retrovirus a total of two times, on successive days, by transferring $0.5-1.0 \times 10^6$ cells in a volume of 1 ml of media to each well of a 24-well non-tissue culture plate which had been coated sequentially with RetroNectin (Takara) and then retrovirus.

Studies requiring withdrawal of the cells from exogenous IL-2 were undertaken by harvesting and washing lymphocytes three times in lymphocyte culture medium without IL-2. After the final wash, the media was tested by IL-2 and/or IL-15 ELISA (Endogen, Cambridge, Mass., and R&D Systems, respectively) to verify that no residual cytokine was present. The cells were then resuspended in lymphocyte culture medium without IL-2 at a concentration of $1 \times 10^6$ cells/ml and returned to tissue culture vessels. The cells were enumerated and assessed for viability by trypan exclusion every 3-7 days. The media was refreshed every 3-7 days by removing half of the spent media and replacing the volume with lymphocyte culture medium without IL-2.

PG13 retroviral packaging cell clones carrying the IL-15 gene were generated using pMSGV1 PPL CO IL-15. A high-titer producer cell clone was selected on the basis of its ability to transduce Sup T1 cells to express IL-15. A Southern blot verified vector integrity and demonstrated 4 sites of vector integration (data not shown). This codon-optimized IL-15 retroviral vector packaging cell was used to produce the retrovirus used in all of the subsequent studies involving IL-15 transduced human lymphocytes. Transduction efficiencies were 50-70% after two sequential transductions as assessed through semi-quantitative PCR and real time PCR (data not shown).

A lymphocyte IL-15 production assay was carried out as follows: Control or IL-15 transduced lymphocytes were washed three times in culture medium. $2 \times 10^5$ lymphocytes were then resuspended in cell culture medium without IL-2 and plated in round-bottom 96-well plates. Half of the wells were precoated with OKT3 antibody (200 µg/well). After 3 days in culture, the cell culture supernatants were harvested for analysis by ELISA (R&D Systems).

Figure 12:
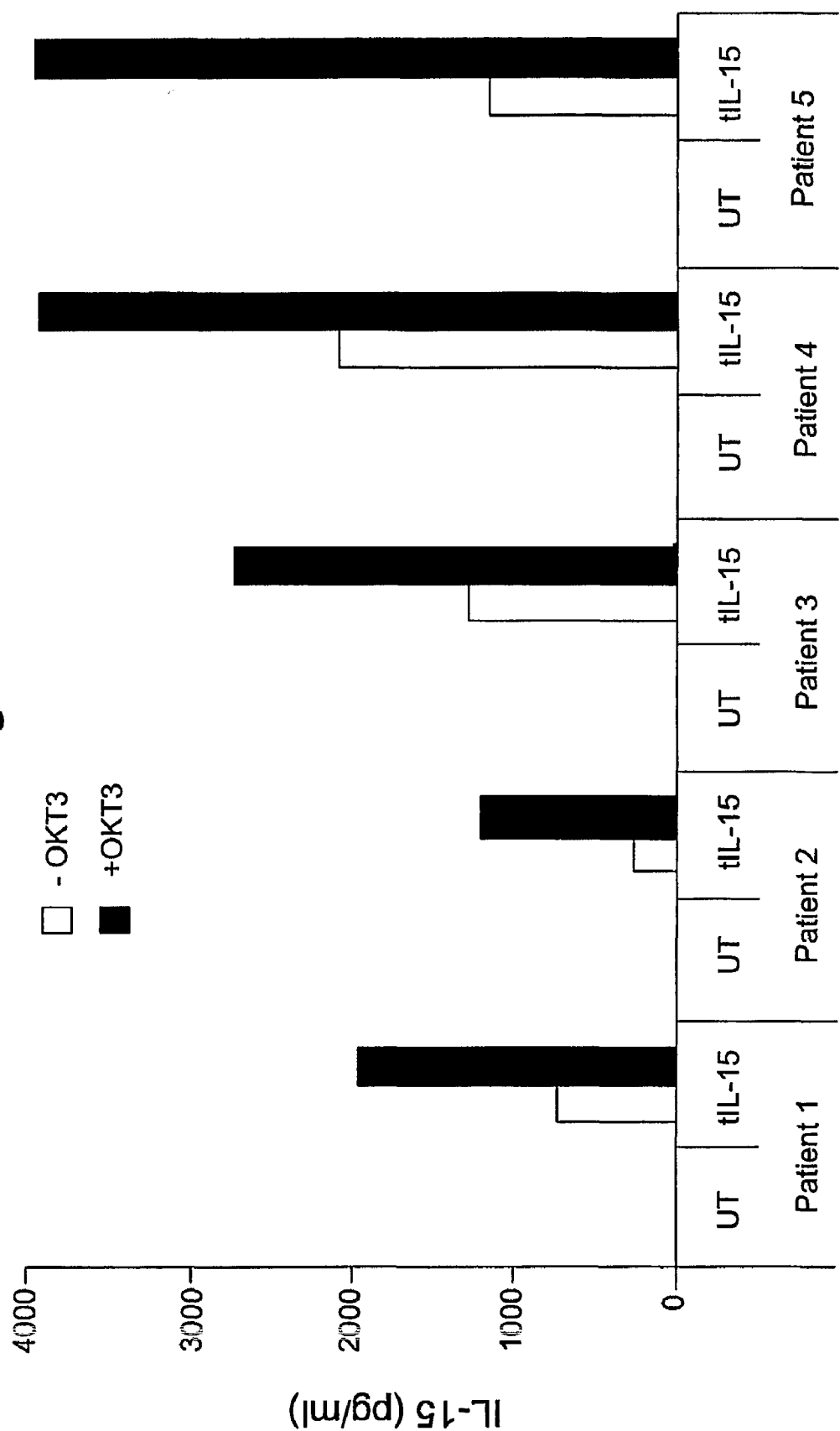
FIG. 12 is a graph of the amount of IL-15 produced by untransduced or IL-15-transduced cells isolated from different patients and stimulated (black bars) or non-stimulated with OKT3 (white bars), in accordance with an embodiment of the invention.

OKT3 stimulated PBLs from 5 patients were transduced with the IL-15 vector. Cytokine production from these cells ranged from 251 to 2095 pg/ml (untransduced cells did not produce detectable quantities of IL-15). Stimulation of the cells with plate-bound OKT3 resulted in a 2 to 5-fold increase in cytokine production; between 1186 and 3957 pg/ml of IL-15 was produced post-stimulation (FIG. 12). Stimulation-dependent activation of the retroviral LTR is well described (Plavec et al., *Gene Ther* 4: 128-139 (1997); Auten et al., *Hum Gene Ther* 10: 1389-1399 (1999); Parkman et al., *Annu Rev Med* 51: 33-47 (2000)) and was previously reported in lymphocytes retrovirally transduced with IL-2 (Liu et al., *J Immunother* 26: 190-201 (2003)).

Figure 13:
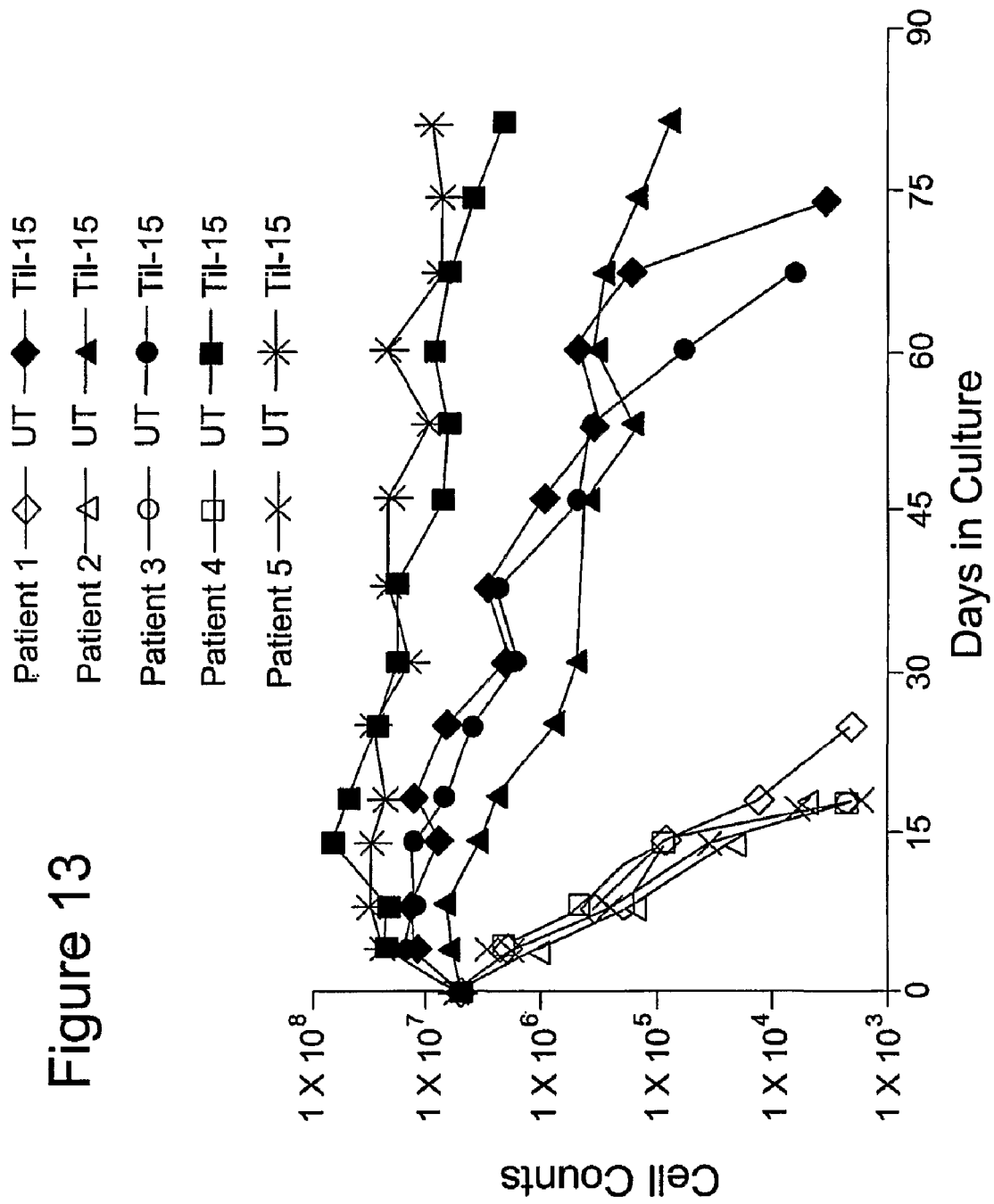
FIG. 13 is a graph of the numbers of cells from FIG. 12 in culture in the absence of exogenous cytokine, in accordance with an embodiment of the invention. Untransduced cells from Patient 1 ◇; IL-15-transduced cells from Patient 1 ◆; untransduced cells from Patient 2 △; IL-15-transduced cells from Patient 2 ▲; untransduced cells from Patient 3 ○; IL-15-transduced cells from Patient 3 ●; untransduced cells from Patient 4 □; IL-15-transduced cells from Patient 4 ■; untransduced cells from Patient 5 X; and IL-15-transduced cells from Patient 5*.
Figure 14:
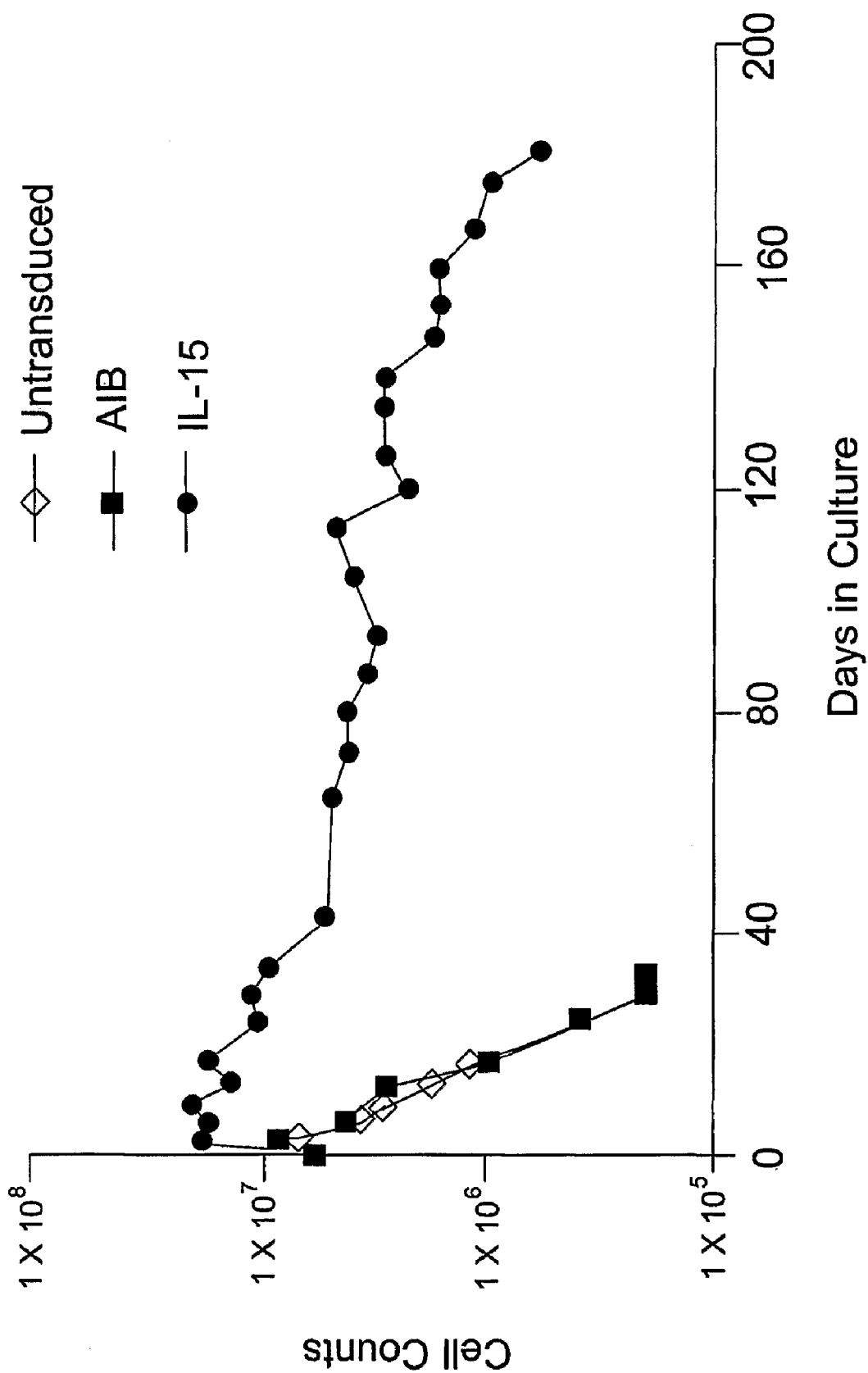
FIG. 14 is a graph of the numbers of cells (untransduced ◇; transduced with a control vector ■; or transduced with IL-15 vector ●) in culture for more than 180 days, in accordance with an embodiment of the invention. AIB represents lymphocytes transduced with a control vector.

After 7 days in culture and 4 days after the final transduction, the lymphocytes were thoroughly washed to remove all traces of soluble cytokines and returned to culture in the absence of exogenous cytokine. Untransduced lymphocytes rapidly declined in both viability and cell counts. By day 30 after cytokine withdrawal, no untransduced cells could be detected. In contrast, IL-15 transduced lymphocytes uniformly persisted in vitro for greater than 60 days (FIG. 13). After 60 days, 2 of 5 IL-15 vector transduced cultures significantly declined in viability while the remaining 3 cultures persisted beyond 80 days in the absence of added cytokine. In a similar experiment, carried out over a longer time course, IL-15 transduced cells persisted in vitro for 181 days, while untransduced lymphocytes and lymphocytes transduced with a control gene were undetectable after culture for 30 days in the absence of exogenous cytokine (FIG. 14).

During the course of these studies, lymphocytes from 17 patients were transduced with the IL-15 vector. Consistently, IL-15 transduced lymphocyte cultures demonstrated prolonged in vitro persistence after IL-2 withdrawal compared to control cultures. In 16 of 17 cultures, viable IL-15 transduced lymphocytes were detected from 40-181 days after cytokine withdrawal. However, one of the 17 IL-15 transduced cultures exhibited logarithmic, clonal expansion for more than 365 days (data not shown); this cell line is under active investigation.

Example 14

This example demonstrates that activated human T cells express IL-15Rα.

Figure 15:
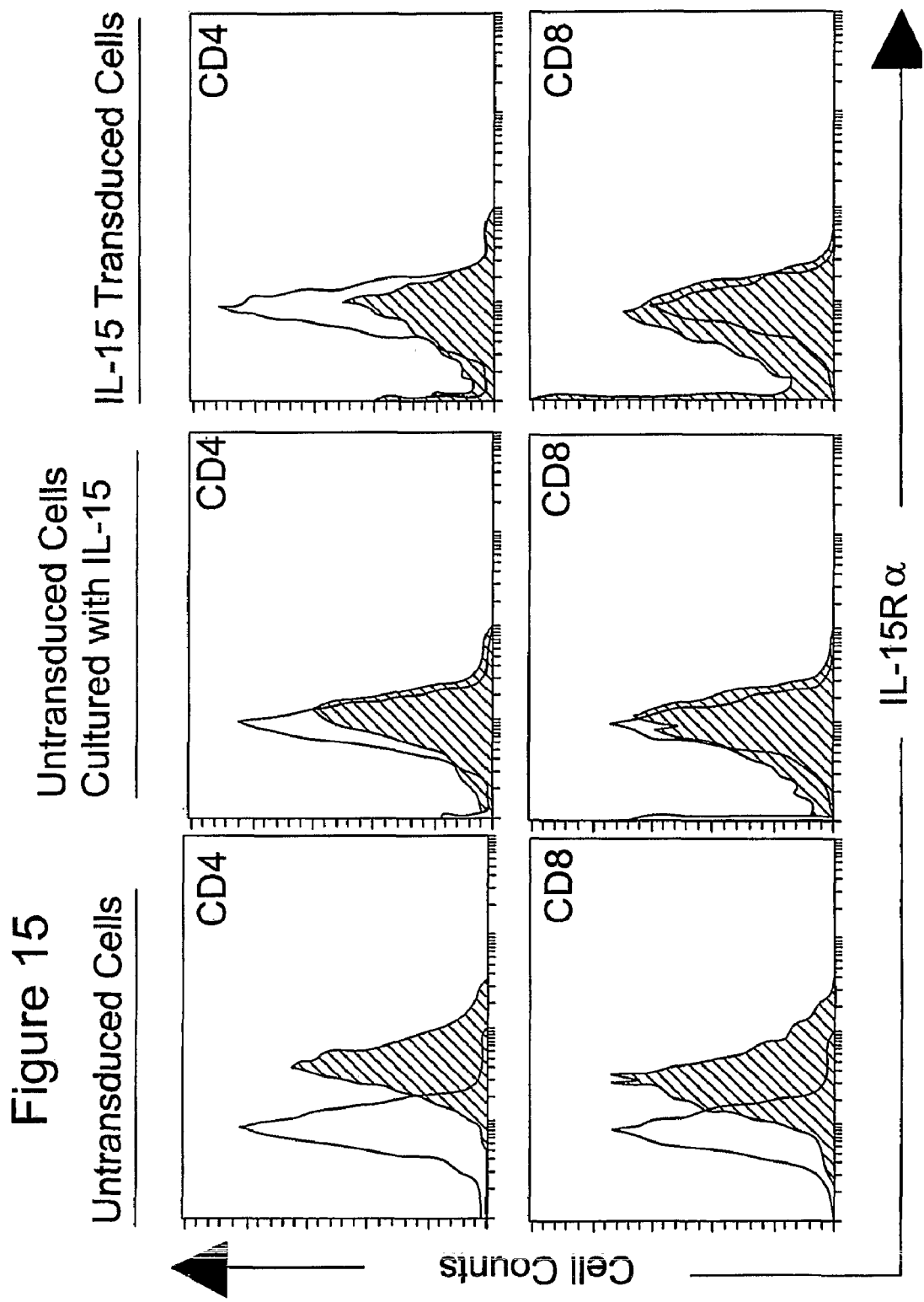
FIG. 15 is a graphical representation of the expression of certain cell surface molecules by untransduced cells, untransduced cells cultured with IL-15, and IL-15 transduced cells, in accordance with an embodiment of the invention.

IL-15- and IL-15Rα-deficient mice manifest similar phenotypes, exhibiting decreased numbers of $CD8^+$ cells and nearly a total lack of memory CD8 cells suggesting that the high affinity IL-15Rα is critical to the function of IL-15 in vivo (Kovanen et al., *Immunol Rev* 202: 67-83 (2004)). In vitro, supraphysiologic levels of cytokine can engage intermediate and low affinity IL-15 receptors on lymphocytes lacking IL-15Rα. To determine whether IL-15Rα was expressed in OKT3 activated T cells, IL-15 transduced lymphocytes, as well as untransduced control cells, grown in media containing either IL-2 or IL-15 were evaluated (FIG. 15). IL-15Rα was detected with a polyclonal, biotinylated antibody and biotinylated isotype-matched control antibody; cell surface-bound antibody was then labeled with streptavidin-PE (R&D Systems). PE was detected through flow cytometry.

Untransduced lymphocytes, stimulated with OKT3 and IL-2 at day 0 of culture, expressed IL-15Rα in both $CD4^+$ and $CD8^+$ subsets (86% and 69% positive compared to isotype control, respectively. Untransduced lymphocytes stimulated with OKT3 and grown in media containing 100 ng/ml of IL-15 did not manifest IL-15Rα staining, nor did IL-15 vector transduced lymphocytes. Thus, exogenous or endogenous IL-15 appeared to downregulate the expression of IL-15Rα.

Example 15

This example demonstrates the phenotype of IL-15 transduced lymphocytes.

T lymphocyte subsets are often defined by cell surface expression of costimulatory molecules, adhesion molecules, and receptors; these cell surface proteins, in turn, are subject to influences such as TCR stimulation and cytokine engagement. In order to further define the influence of IL-15 transduction on T lymphocytes, long-term cultures of IL-15 transduced lymphocytes grown in the absence of exogenous cytokine, as well as untransduced lymphocytes grown in media containing either IL-2 or IL-15, were evaluated. Cell surface expression of CD3, CD4, CD8, CD27, CD28, CD45RA, CD45RO, CD62L, and CCR7 was measured using FITC, PE, or APC conjugated antibodies and the corresponding isotype controls (BD Pharmingen, San Diego, Calif.). FITC, PE, or APC was detected using flow cytometry.

Figure 16:
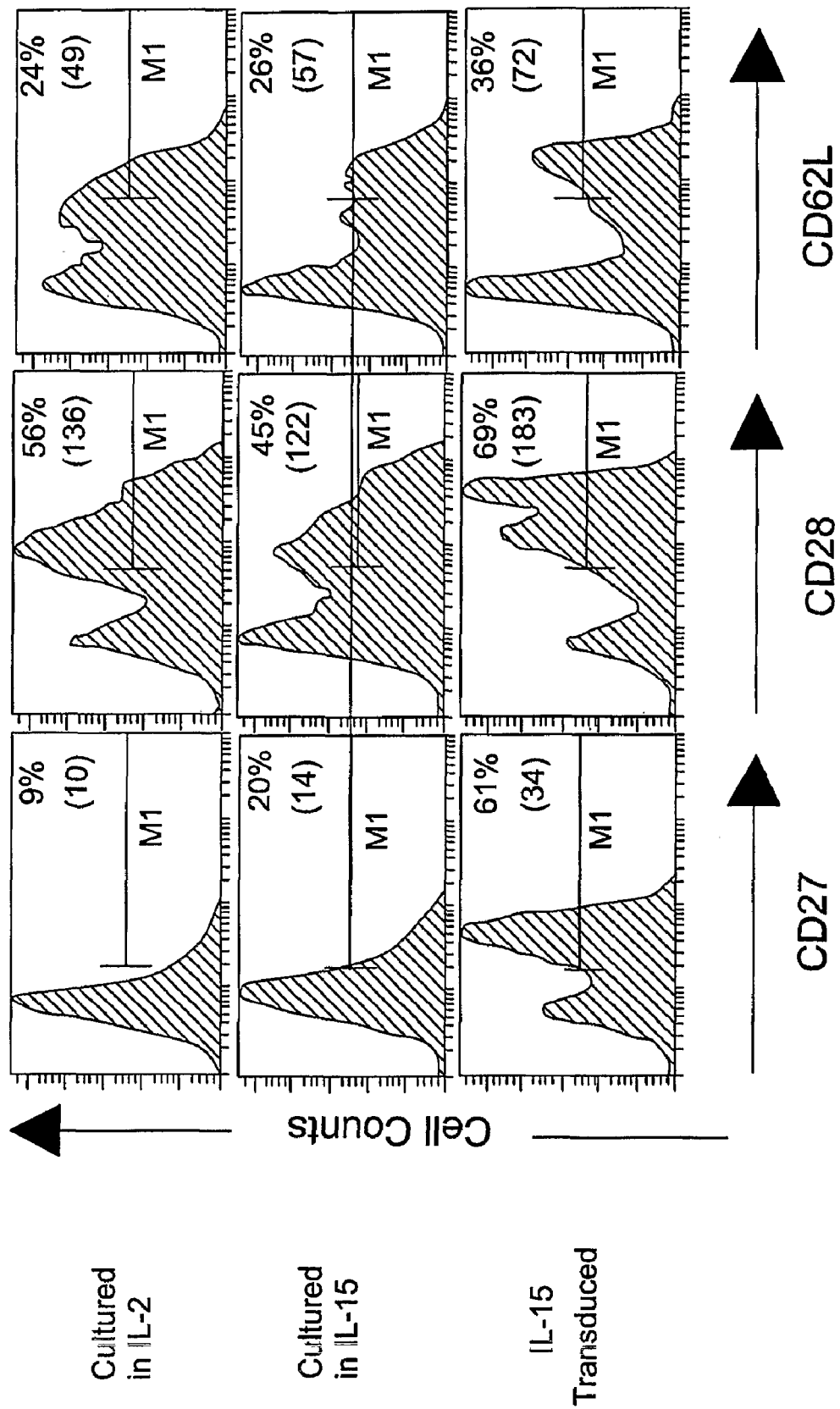
FIG. 16 is a graphical representation of the expression of certain cell surface molecules by untransduced cells cultured in IL-2-containing media, untransduced cells cultured in IL-15-containing media, or IL-15-transduced cells, in accordance with an embodiment of the invention.

IL-15 transduced lymphocytes demonstrated modest increases in staining for CD27, CD28, and CD62L with respect to untransduced lymphocytes cultured in IL-2 or IL-15 (FIG. 16). This was reflected both in the percentage of cells exhibiting positive staining compared to isotype controls and the mean fluorescence intensity. No differences were seen in the expression of CD45RA, CD45RO, nor CCR7 (data not shown).

Example 16

This example demonstrates that OKT3 stimulated PBLs transduced with IL-15 continue to proliferate in the absence of exogenous cytokine support and resist cytokine withdrawal induced apoptosis When OKT3 stimulated PBLs were transduced with the IL-15 gene, they remained viable for prolonged periods in culture, but ceased to increase in cell number. The mechanisms for this persistence was analyzed by first evaluating thymidine incorporation. The lymphocyte proliferation assay was carried out as follows: Lymphocytes were washed three times with culture medium and plated at $1\times10^5$ cells/well in a 96-well, round-bottom microplate in the presence or absence of 300 IU/ml IL-2. The cells were cultured for a total of four days and in the final 16 hours of culture, 1 µCi/well [methyl-3H]thymidine (PerkinElmer Life Sciences, Boston, M) was added to each well. Cellular DNA was harvested and counted by liquid scintillation counting.

Figure 17:
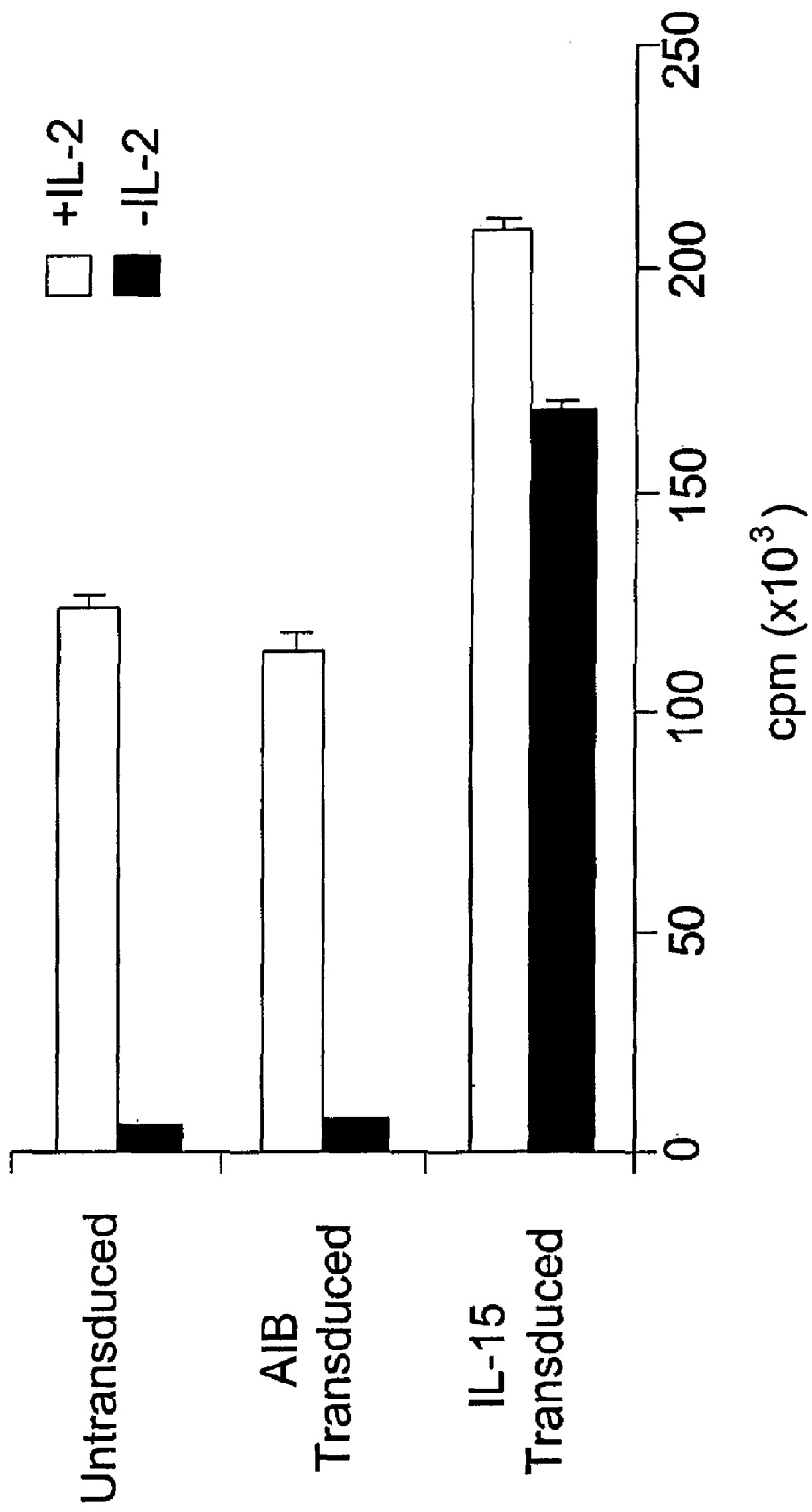
FIG. 17 is a graph of the proliferation (as determined by the uptake of 3H-thymidine) of untransduced cells, or cells transduced with a control vector or IL-15-encoding vector cultured in the presence (white bars) or absence (black bars) of IL-2, in accordance with an embodiment of the invention.

On culture day 7, untransduced, control vector transduced, and IL-15 transduced lymphocytes were washed free of IL-2, then cultured in the presence or absence of IL-2 for 4 days. $^3$H-thymidine was added during the final 16 hours of culture. Assessment of thymidine incorporation revealed that the IL-15 transduced cells continued to proliferate in the absence of exogenous cytokine, while the untransduced or control transduced cells did not (FIG. 17).

Figure 18:
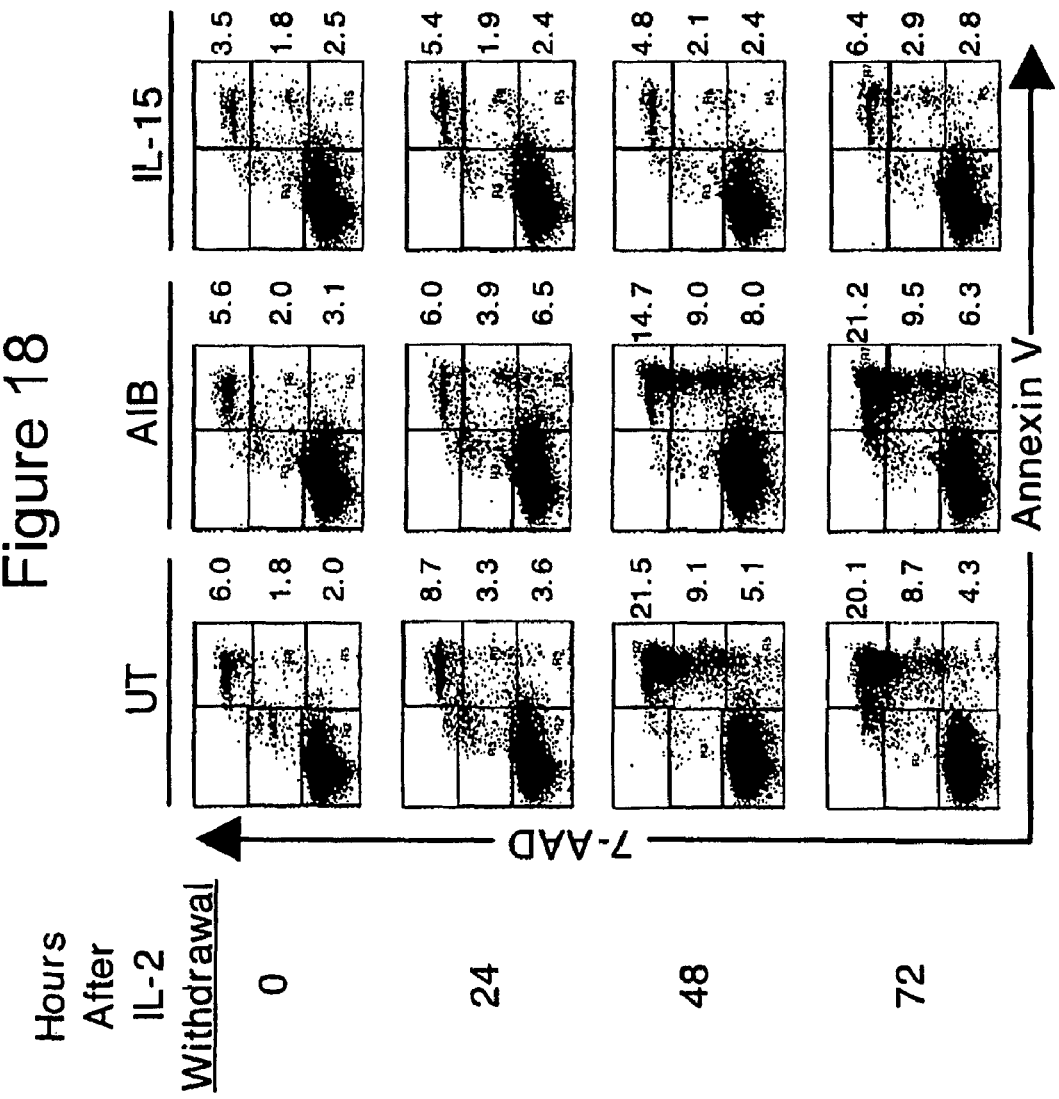
FIG. 18 is a graphical representation of a time course of 7-AAD/Annexin-V staining of untransduced cells (UT), or cells transduced with a control vector (AIB) or an IL-15-encoding vector, which cells were cultured in the absence of IL-2 and stimulated by OKT3, in accordance with an embodiment of the invention.

Whether the IL-15 transduced cells were protected from apoptotic death upon IL-2 withdrawal was next evaluated. Fractions of cultures of untransduced, control vector transduced, and IL-15 transduced PBLs were sequentially withdrawn from IL-2 for 3 consecutive days, starting on culture day 7. Four days later, cells were stained for 7-AAD/Annexin V and analyzed by flow cytometry (FIG. 18). Annexin V and 7-AAD staining for the detection of apoptotic cells was performed using the Annexin V-PE Apoptosis Kit I (BD Pharmingen). Immunofluorescence was measured using a FACscan flow cytometer and analyzed using CellQuest Pro software (Becton Dickinson).

Untransduced and control gene transduced cell populations demonstrated an increase in apoptotic cells within 24 hours after cytokine withdrawal; the percentage of cells undergoing apoptosis (positively for Annexin V, but not 7-AAD) peaked at approximately 14-17%, 48 hours after cytokine withdrawal. Necrotic cells, defined by 7-AAD positively, accumulated continuously in these cultures after IL-2 was withdrawn and approximately 35% of the cells in the populations lacking cytokine support were necrotic or undergoing apoptosis by 72 hours. In contrast, IL-15 transduced PBLs resisted apoptosis after withdrawal from IL-2. Over 72 hours, the percentage of apoptotic cells increased slightly from 4.3 to 5.7%, while necrotic cells increased from 3.5 to 6.4%.

Example 17

This example demonstrates that IL-15 transduced PBLs maintain Bcl-2 and Bcl-XL expression after withdrawal from IL-2.

Figure 19:
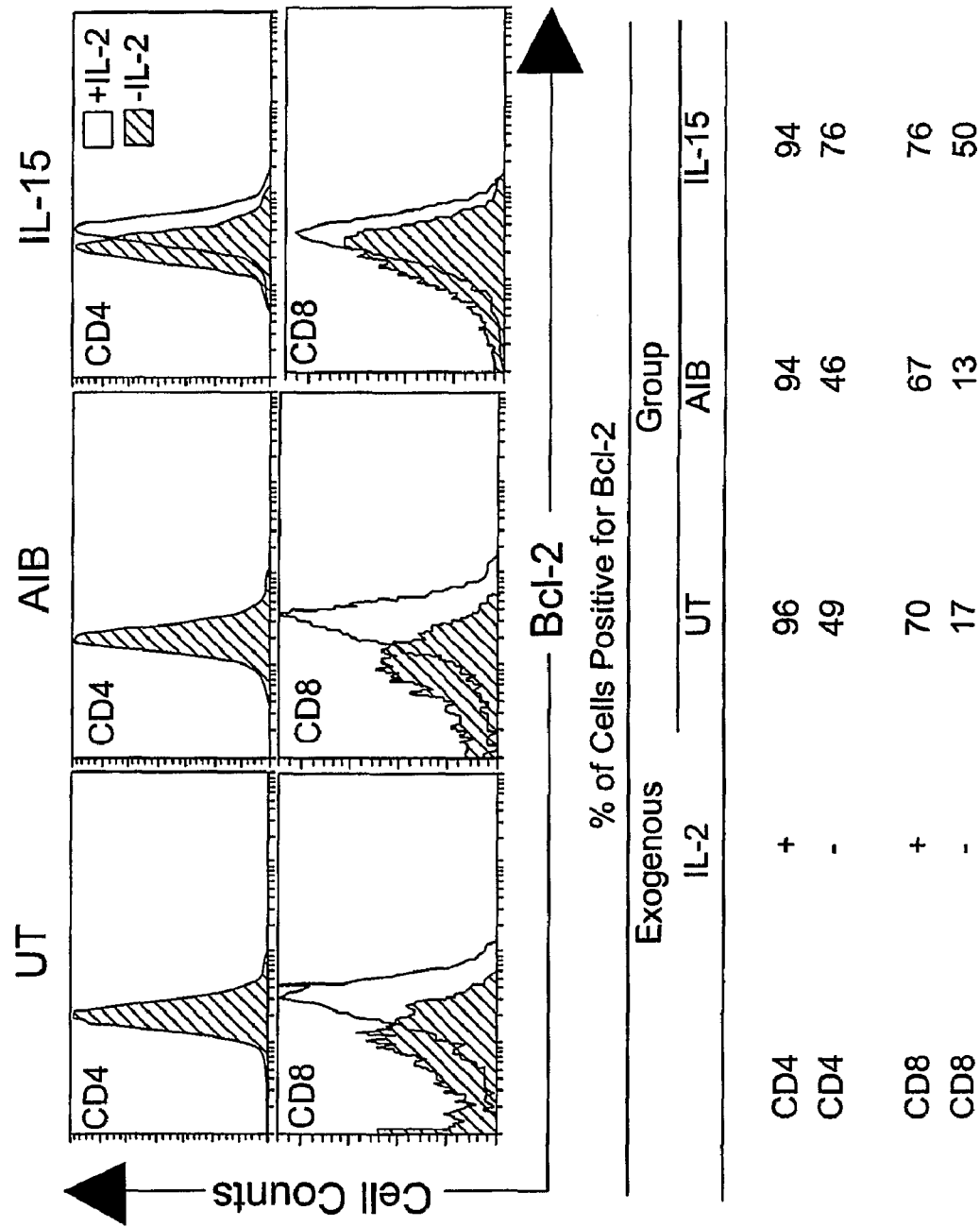
FIG. 19 is a graphical representation of the expression of Bcl-2 by untransduced cells (UT), or cells transduced with a control vector (AIB) or an IL-15 encoding vector, which cells were cultured in the presence (white histograms) or absence (gray histograms) of IL-2, in accordance with an embodiment of the invention.
Figure 20:
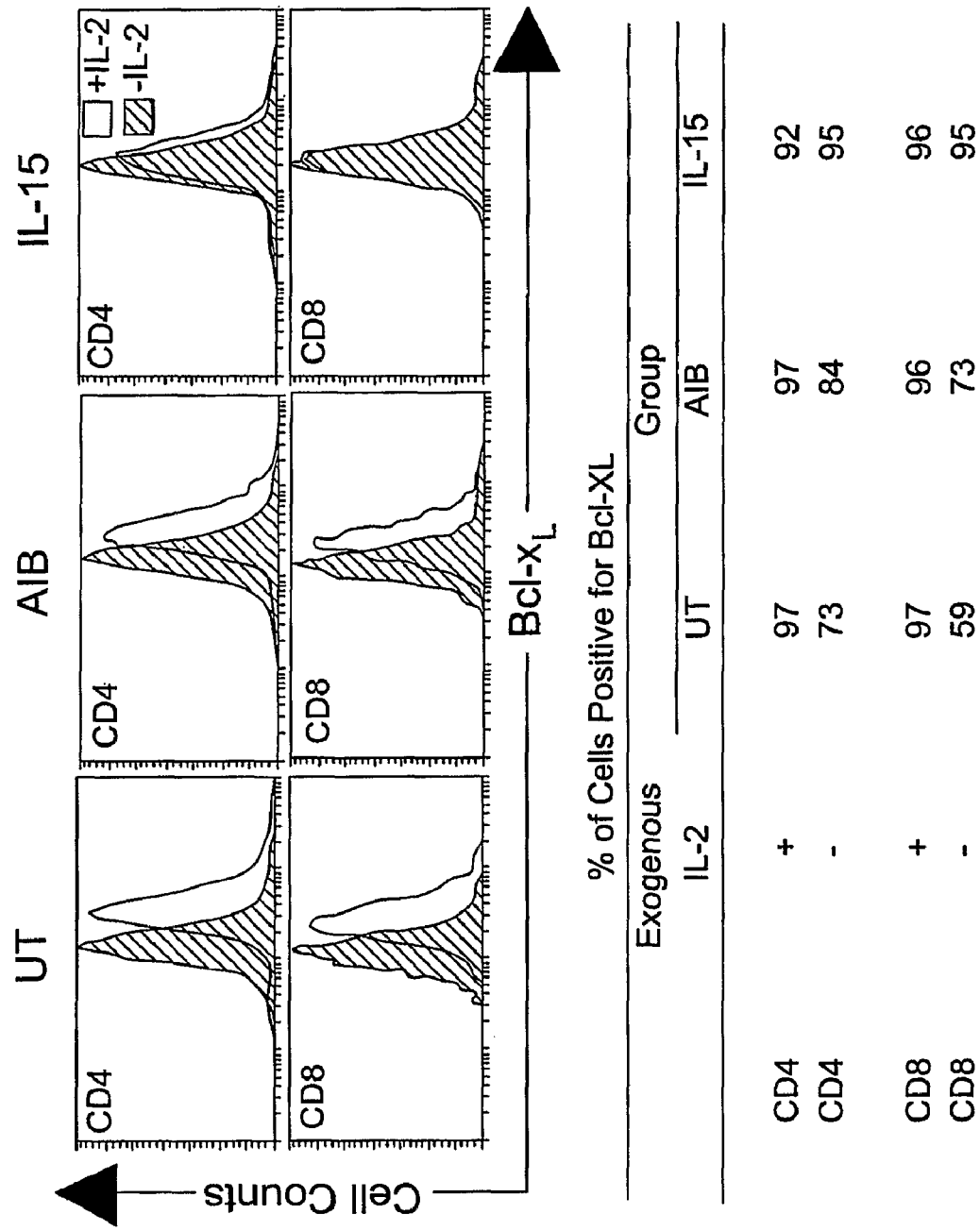
FIG. 20 is a graphical representation of the expression BCl-$X_L$ by untransduced cells (UT), or cells transduced with a control vector (AIB) or an IL-15 encoding vector, which cells were cultured in the presence (white histograms) or absence (gray histograms) of IL-2, in accordance with an embodiment of the invention.

CD8 lymphocytes from HIV patients demonstrate decreased levels of anti-apoptotic proteins Bcl-2 and Bcl-XL which can be reversed by exposure to IL-15 (27). Because IL-15 transduced lymphocytes resisted apoptosis after cytokine withdrawal, CD4 and CD8 lymphocytes were evaluated for Bcl-2 and Bcl-XL expression (FIGS. 19 and 20). Intracellular proteins Bcl-2 and Bcl-XL were detected using FITC and PE conjugated antibodies and their respective isotype controls (BD Pharmingen and Southern Biotechnology Associates, Inc., Birmingham, Ala.). Cells were washed two times in staining buffer composed of PBS with 0.5% BSA and stained with cell surface antibodies or matched isotype controls followed by incubation in the dark for 20 m at 4° C. Cells were then washed two more times with staining buffer prior to analysis. Intracellular staining was performed by fixing and permeableizing the cells with Cytofix/Cytoperm solution (BD Pharmingen), two washes in Perm/Wash buffer (BD Pharmingen), staining with intracellular antibodies or isotype controls, and two additional washes prior to analysis.

Levels of Bcl-2 and Bcl-XL were downregulated in untransduced and control transduced cells 2 days post-cytokine withdrawal. In contrast, expression of these proteins was maintained in IL-15 transduced CD4 and CD8 lymphocytes following withdrawal from IL-2; Bcl-XL demonstrated no decrease in expression while Bcl-2 displayed a modest decrease in expression (18% and 16% decrease in IL-15 transduced CD4 and CD8 cells versus 47-48% and 53-54% decrease in control CD4 and CD8 cultures).

Example 18

This example demonstrates that the specific peptide recognition by IL-15 transduced lymphocytes is maintained after withdrawal from IL-2.

To further evaluate the function of IL-15 transduced lymphocytes, peptide-stimulated lymphocyte cultures with reactivity to the melanoma antigen gp100 were generated and subsequently transduced with the codon-optimized IL-15 vector. Untransduced and IL-15 transduced lymphocytes exhibited identical patterns of staining with gp100 tetramer, with 50-80% of CD8 cells staining positively after one round of peptide stimulation (data not shown). Subsequently, coculture experiments were performed utilizing peptide-pulsed T2 cells as stimulators. The lymphocyte antigen reactivity assay was carried out as follows: Target cells were prepared by pulsing T2 cells with 10-1000 ng/ml of peptide in cell culture medium for 2 h at 37° C. The following HLA-A2 restricted peptides were used: influenza peptide (GILGFVFTL) (SEQ ID NO: 9), MART-1:27-35 peptide, or native gp100:209-217. $1\times10^5$ effector cells (PBL) were co-cultured with $1\times10^5$ target cells (peptide-pulsed T2) in a final volume of 0.2 ml in each well of a round-bottom 96-well plate. 24 hours later, cell culture supernatants were harvested and assayed for interferon-γ production by ELISA (Endogen).

Figure 21:
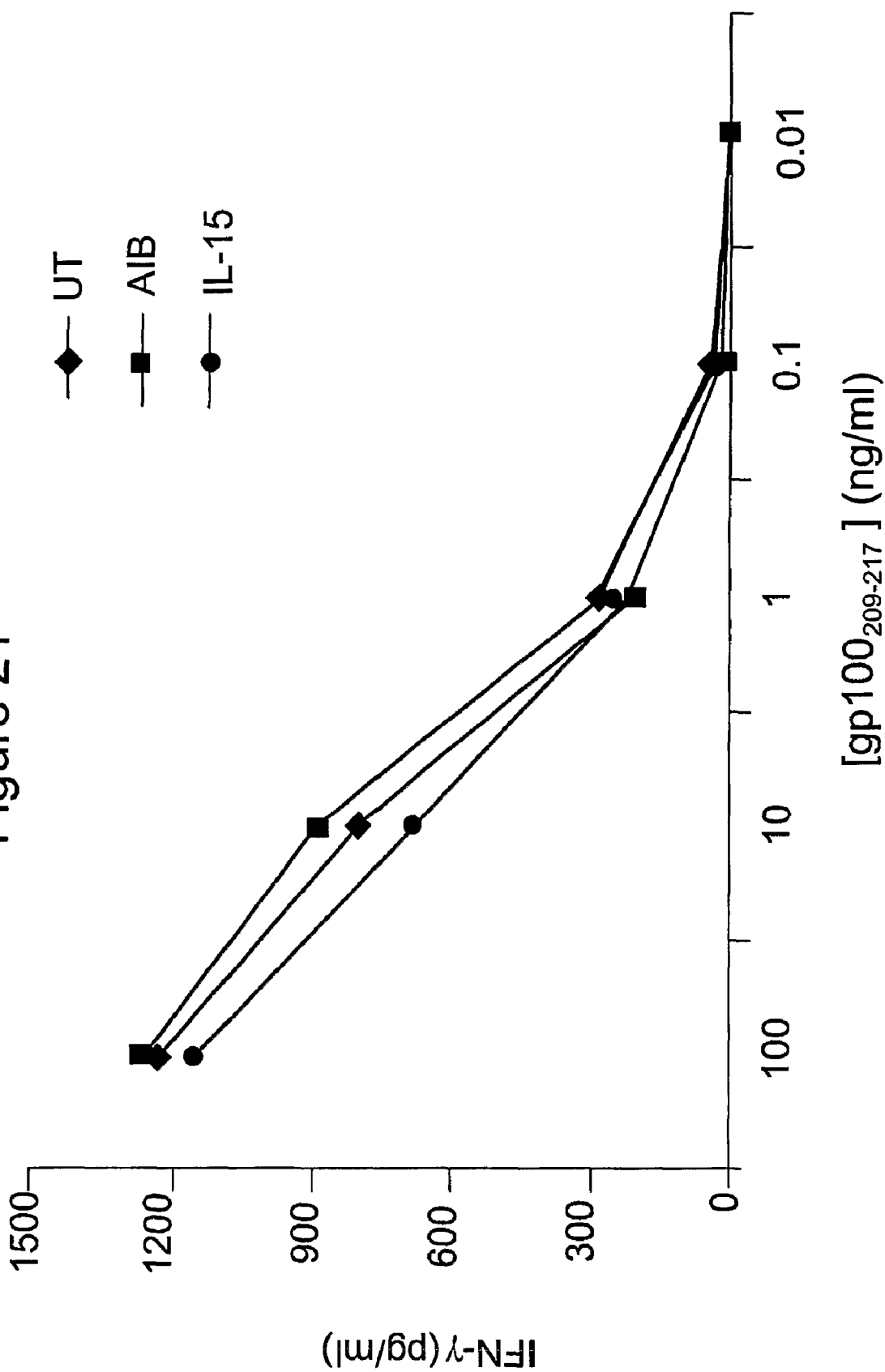
FIG. 21 is a line graph depicting the IFN-γ produced by untransduced cells (UT; ◆), or cells transduced with a control vector (AIB; ●) or with an IL-15 encoding vector (IL-15; ■), in response to stimulation with T2 cells pulsed with varying amounts of gp100 peptide, in accordance with an embodiment of the invention.
Figure 22:
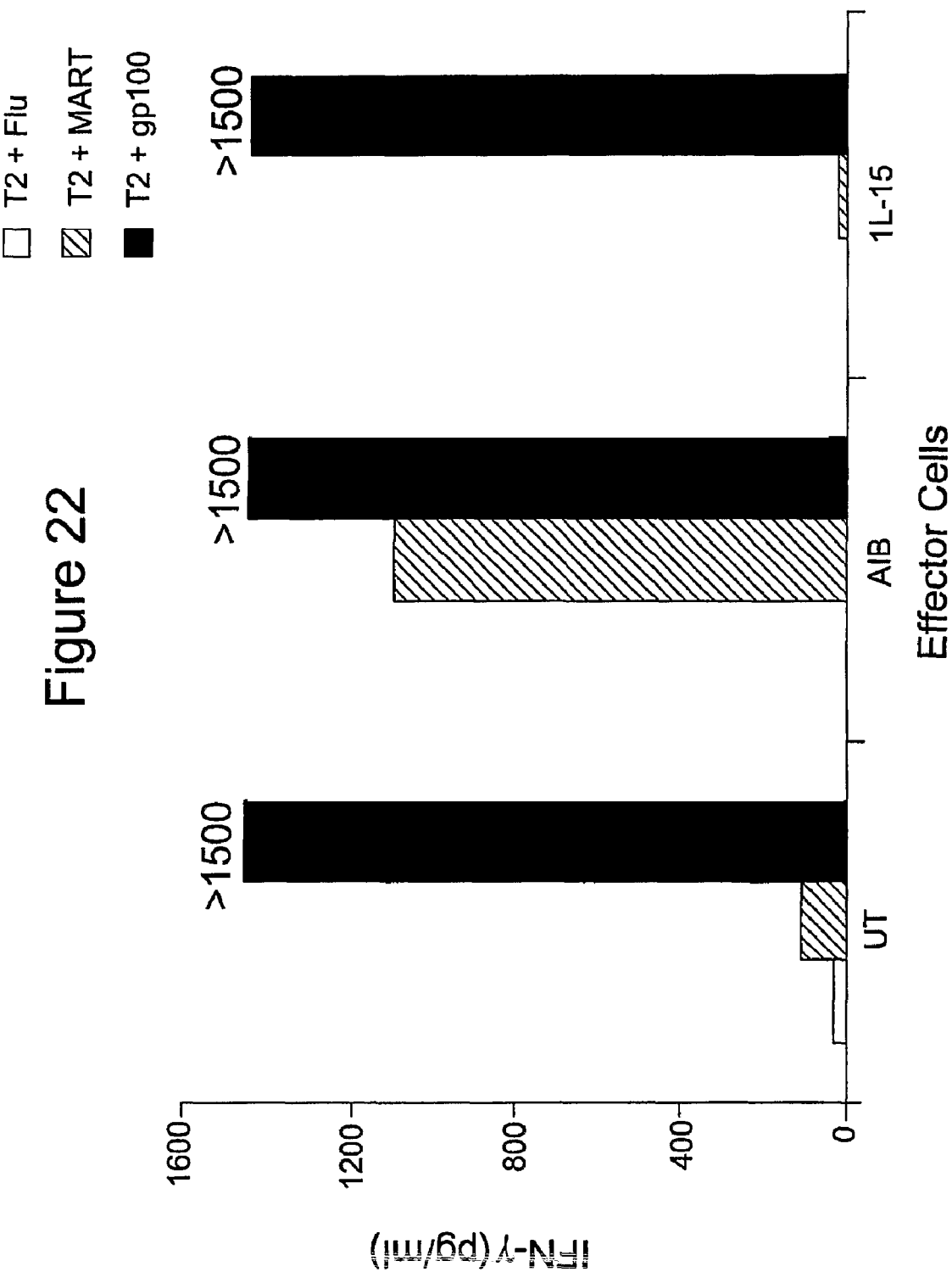
FIG. 22 is a graph of the IFN-γ produced by untransduced cells (UT), or cells transduced with a control vector (AIB) or with an IL-15 encoding vector, in response to stimulation with T2 cells pulsed with different antigenic peptides: influenza viral peptide (Flu; white bars), MART-1 peptide (MART; gray bars), or gp100 peptide (gp100; black bars), before IL-2 was withdrawn from the cell culture media, in accordance with an embodiment of the invention.
Figure 23:
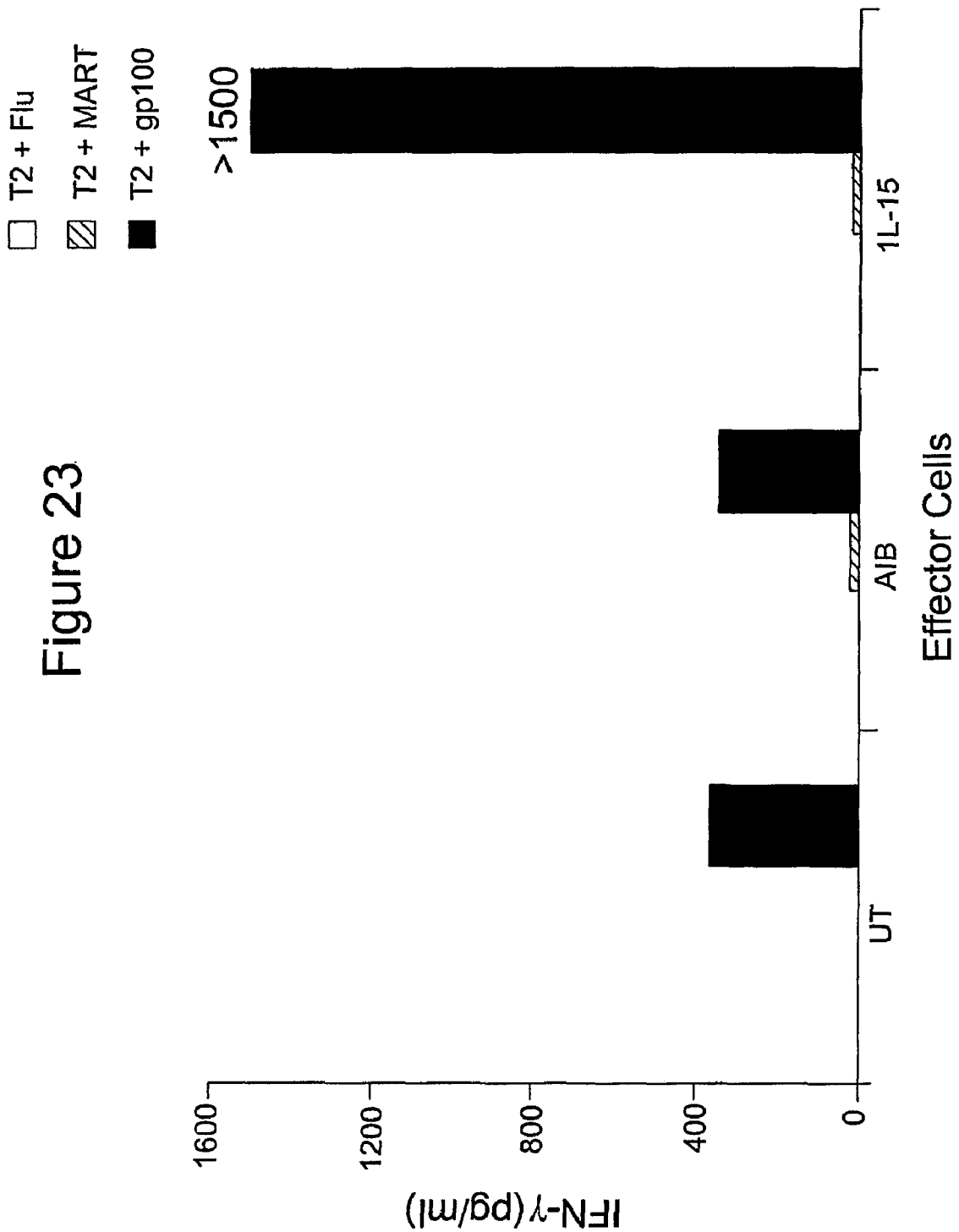
FIG. 23 is a graph of the IFN-γ produced by untransduced cells (UT), or cells transduced with a control vector (AIB) or with an IL-15 encoding vector, in response to stimulation with T2 cells pulsed with different antigenic peptides: influenza viral peptide (Flu; white bars), MART-1 peptide (MART; gray bars), or gp100 peptide (gp100; black bars), after IL-2 was withdrawn from the cell culture media, in accordance with an embodiment of the invention.
Figure 24:
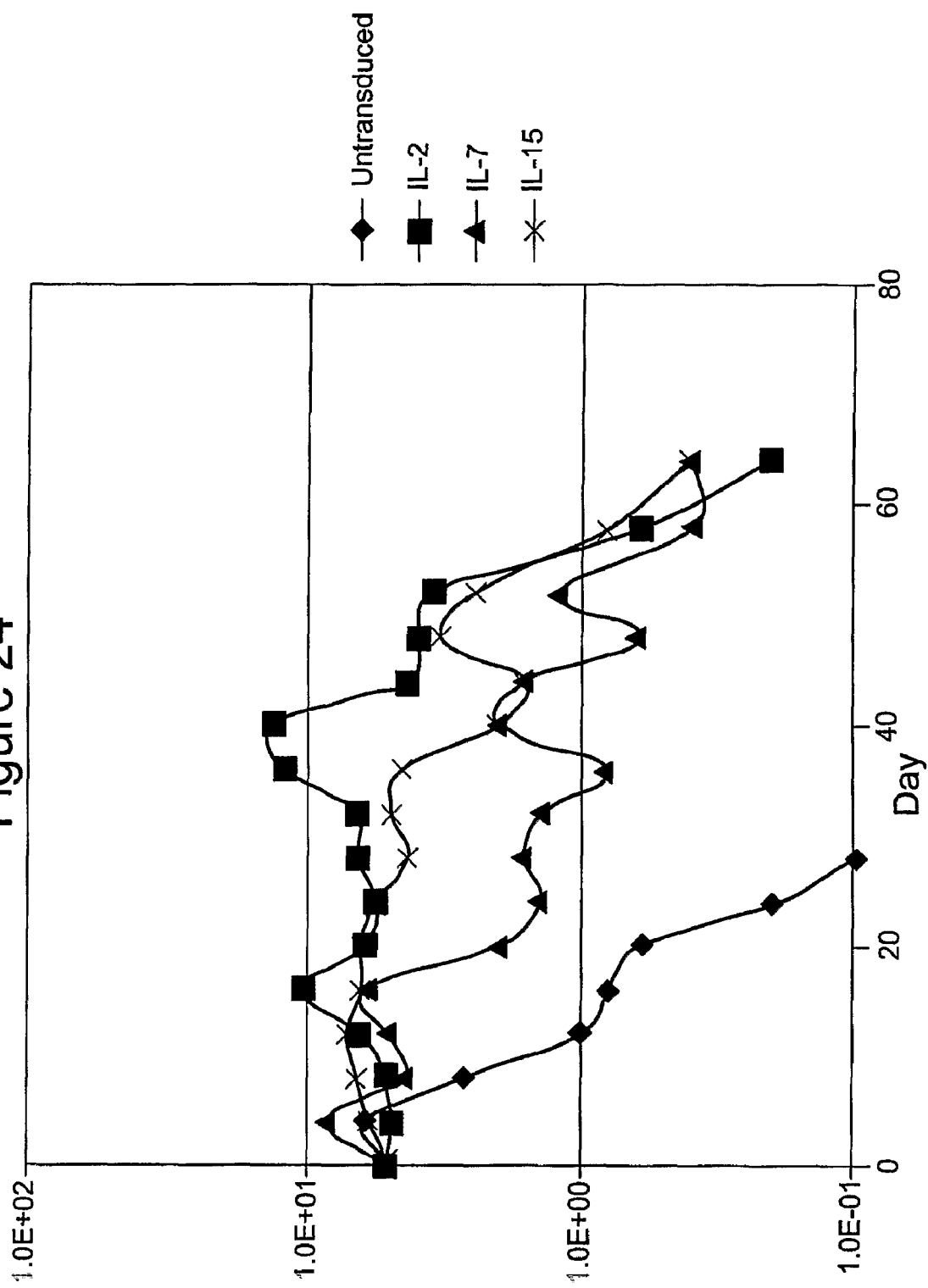
FIG. 24 is a graph of the number of cells (untransduced (UT; ◆), or transduced with IL-2 (■), IL-7 (▲), or IL-15 (X) vectors) surviving in vitro after exogenous cytokine has been withdrawn from the culture media, in accordance with an embodiment of the invention. Cells were freshly isolated.
Figure 25:
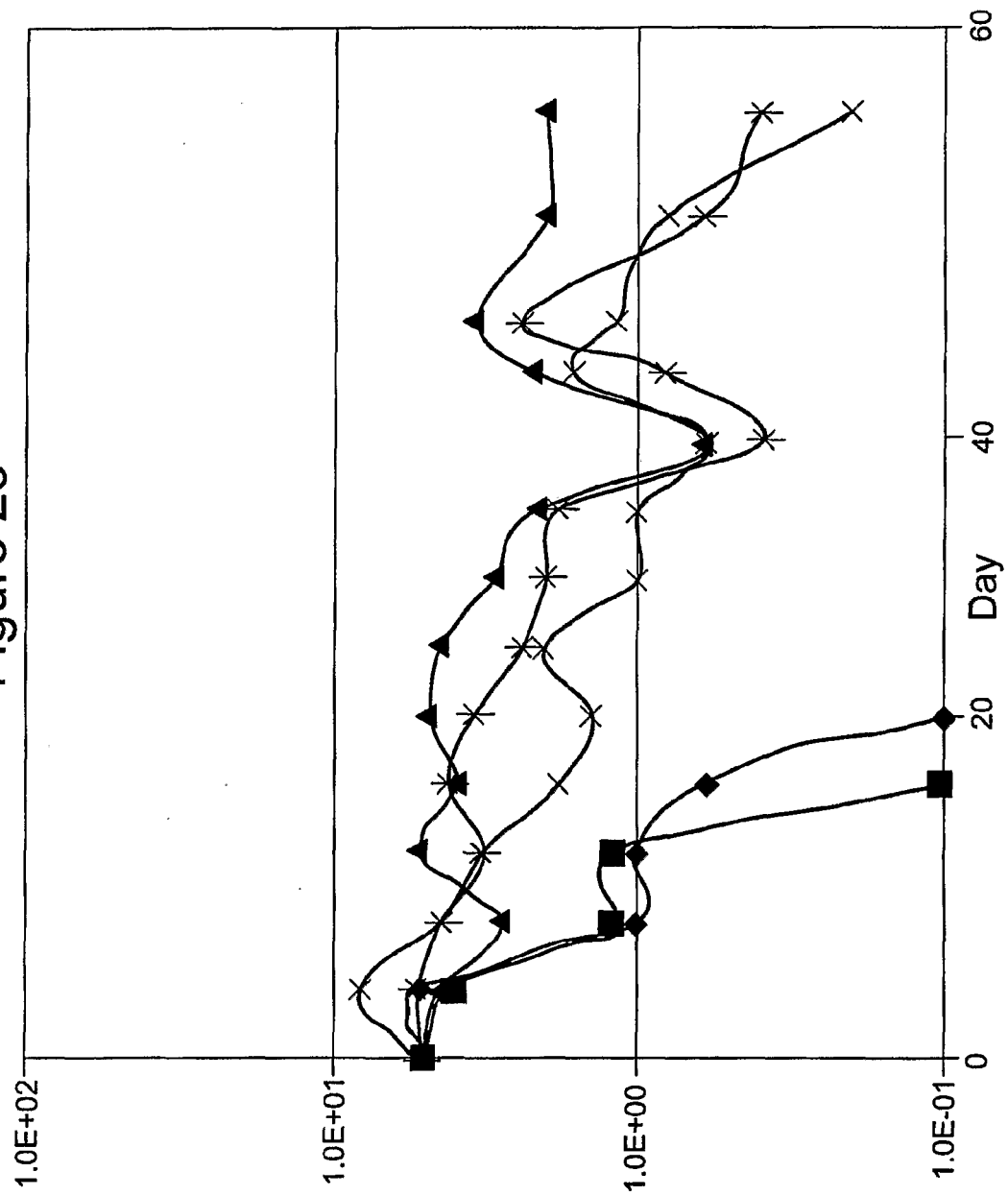
FIG. 25 is a graph of the number of cells (untransduced (UT; ♦), or transduced with control vector MSGIN (■), IL-2 (▲), IL-7 (X), or IL-15 (✱) vectors) surviving in vitro after exogenous cytokine has been withdrawn from the culture media, in accordance with an embodiment of the invention. Cells were thawed cryopreserved cells.

Comparable quantities of IFN-γ were released by control and IL-15 transduced lymphocytes upon exposure to T2 cells pulsed with serial dilutions of the gp100 peptide (FIG. 21). Peptide-specific reactivity was demonstrated by secretion of IFN-γ upon culture of control and IL-15 transduced lymphocytes with T2 cells pulsed with gp100, but not the HLA-A2 restricted influenza peptide (Flu). MART peptide reactivity was seen only in the culture transduced with the MART T-cell receptor (FIG. 22). When the lymphocyte cultures were withdrawn from IL-2, control cultures (untransduced and MART TCR transduced) declined in viability and number while IL-15 transduced lymphocytes remained viable; this was similar to the pattern previously demonstrated in OKT3 activated lymphocytes (data not shown). 5 days after IL-2 withdrawal, the cells were again tested for peptide-reactivity against T2 pulsed target cells; control cultures demonstrated diminished IFN-γ secretion upon encounter with gp100 pulsed T2, while IL-15 transduced cells maintained a high level of specific IFN-γ secretion (FIG. 23).

Example 19

This example demonstrates the ability of the transduced TIL to proliferate upon stimulation with allogeneic dendritic cells (allo-DC).

It is hypothesized that allo-DC cell stimulation of TIL would be enhanced in the cells transduced with common gamma chain cytokines. Furthermore, dendritic cells are able to capture IL-15 via the IL-15Rα and present it in trans to T cells (which do not express the IL-15Rα.

Figure 26:
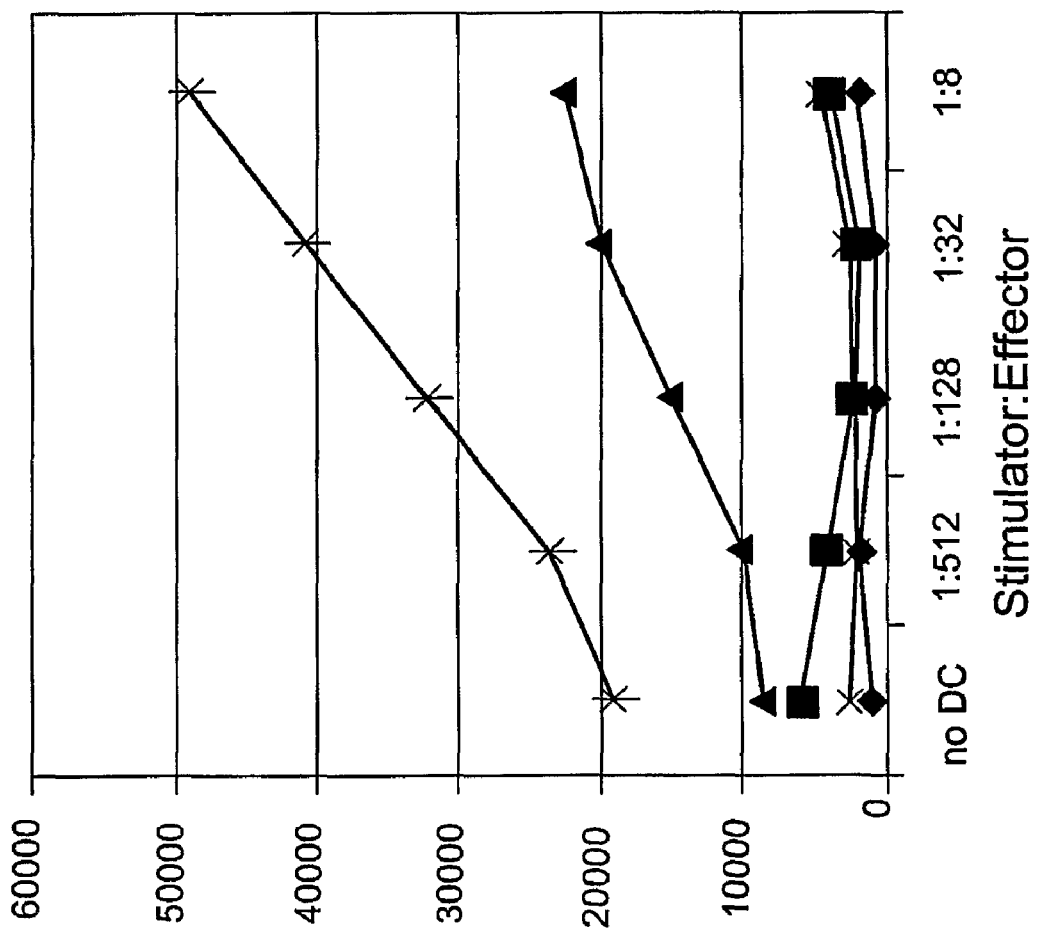
FIG. 26 is a graph of the proliferation (as determined by the uptake of $^3$H-thymidine) of cells (untransduced (UT; ♦), or transduced with control vector MSGIN (■), IL-2 (▲), IL-7 (X), or IL-15 (✱) vectors) in response to stimulation with allogenenic dendritic cells, in accordance with an embodiment of the invention.

Allogeneic DC were generated and co-cultured with the TIL for 4 days in the absence of exogenous IL-2. $^3$H-thymidine was added to the culture in the last 18 hours of culture. The IL-15 transduced cells exhibited the greatest ability to proliferate (FIG. 26). IL-2 also exhibited the ability to proliferate upon stimulation with allogeneic DC.

This example demonstrated the ability of IL-2, IL-7, and IL-15 expressing cells to proliferate in the absence of exogenous cytokine.

Example 20

This example demonstrates that transduced PBL exhibit enhanced survival in the absence of exogenous cytokine in the culture medium.

Figure 27:
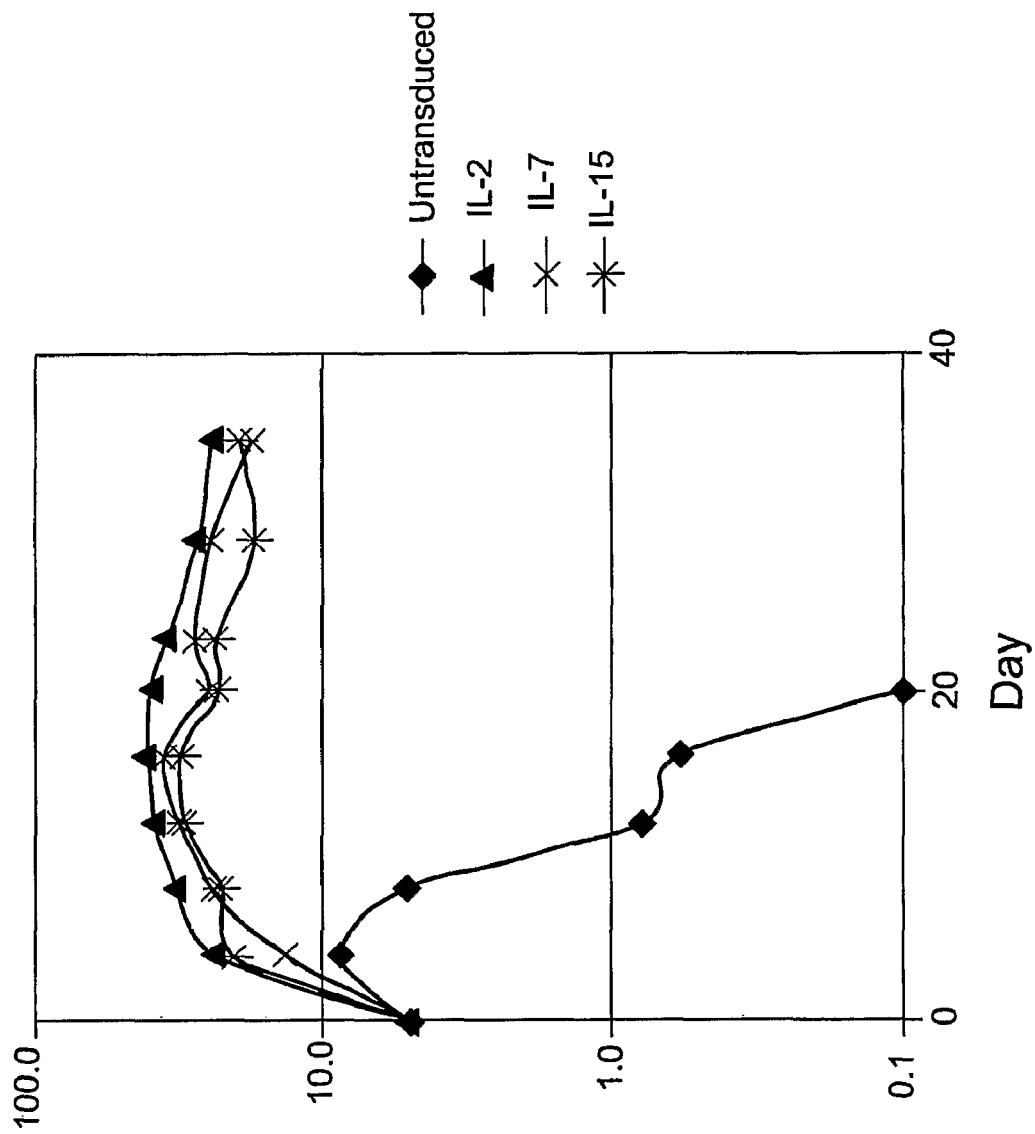
FIG. 27 is a graph of the number of cells (untransduced (♦), or transduced with IL-2-(▲), IL-7 (x), or IL-15 (✱) encoding vectors) surviving after exogenous cytokine has been withdrawn from the culture medium, in accordance with an embodiment of the invention.

PBL isolated from Patient JS were stimulated with OKT3 and then transduced with IL-2-, IL-7-, or IL15-encoding retroviral vectors. Cells were then cultured in the absence of exogenous cytokine for up to 40 days. As shown in FIG. 27, the cells transduced with IL-2, IL-7, or IL-15 exhibited survival past 35 days, whereas untransduced cells did not survive past 20 days.

This example demonstrated that cells transduced with vectors encoding IL-2, IL-7, or IL-15 have enhanced survival in the absence of exogenous cytokine and resist IL-2 withdrawal induced apoptosis.

Example 21

This example demonstrates the ability of PBL transduced with IL-2, IL-7, or IL-15 retroviral vectors to proliferate.

Figure 28:
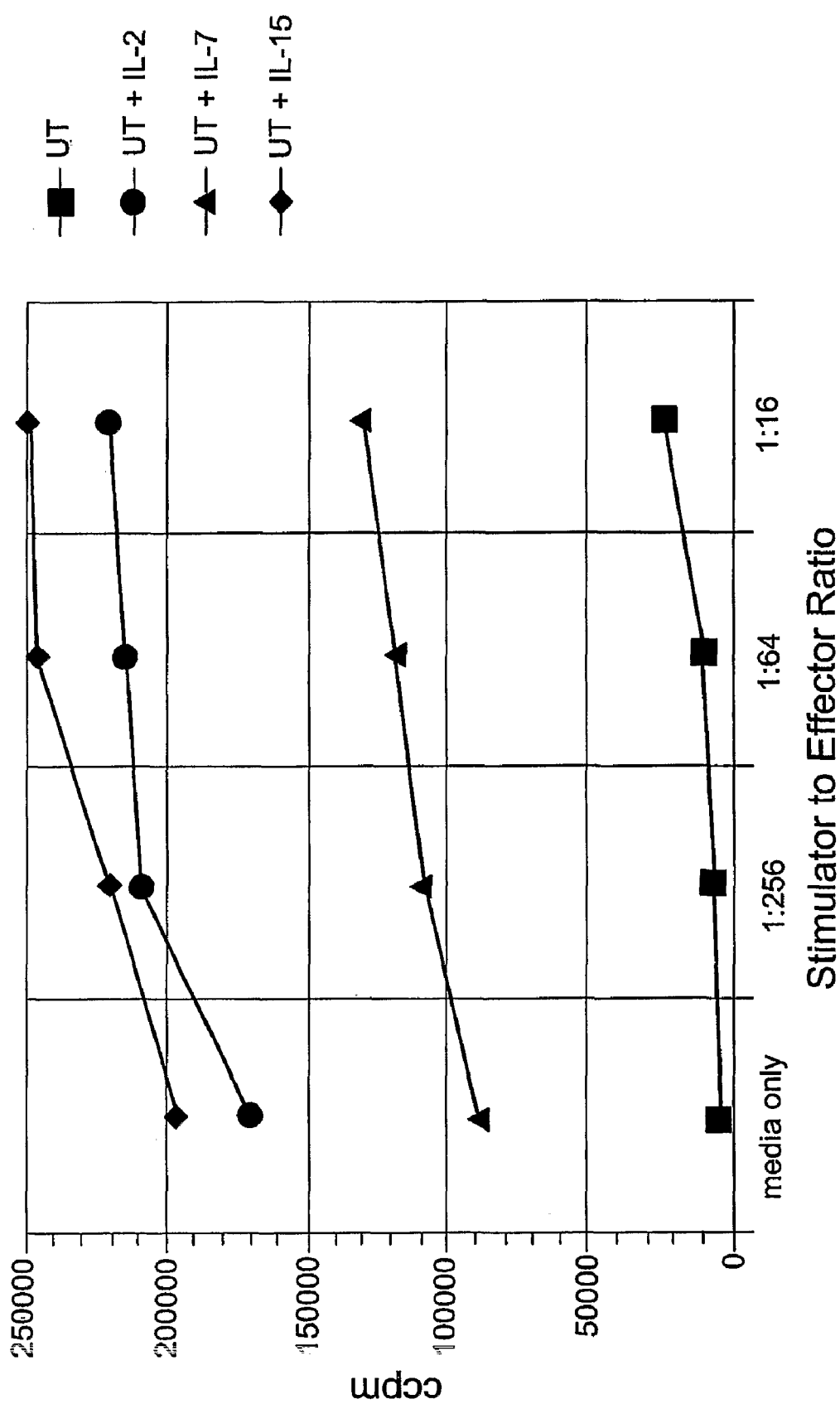
FIG. 28 is a graph of the proliferation (as determined by the uptake of $^3$H-thymidine) of untransduced cells cultured in the absence (■) or presence of exogenous cytokines: IL-2 (●), IL-7 (▲), IL-15 (●), upon stimulation with different ratios of allogeneic dendritic cells, in accordance with an embodiment of the invention.
Figure 29:
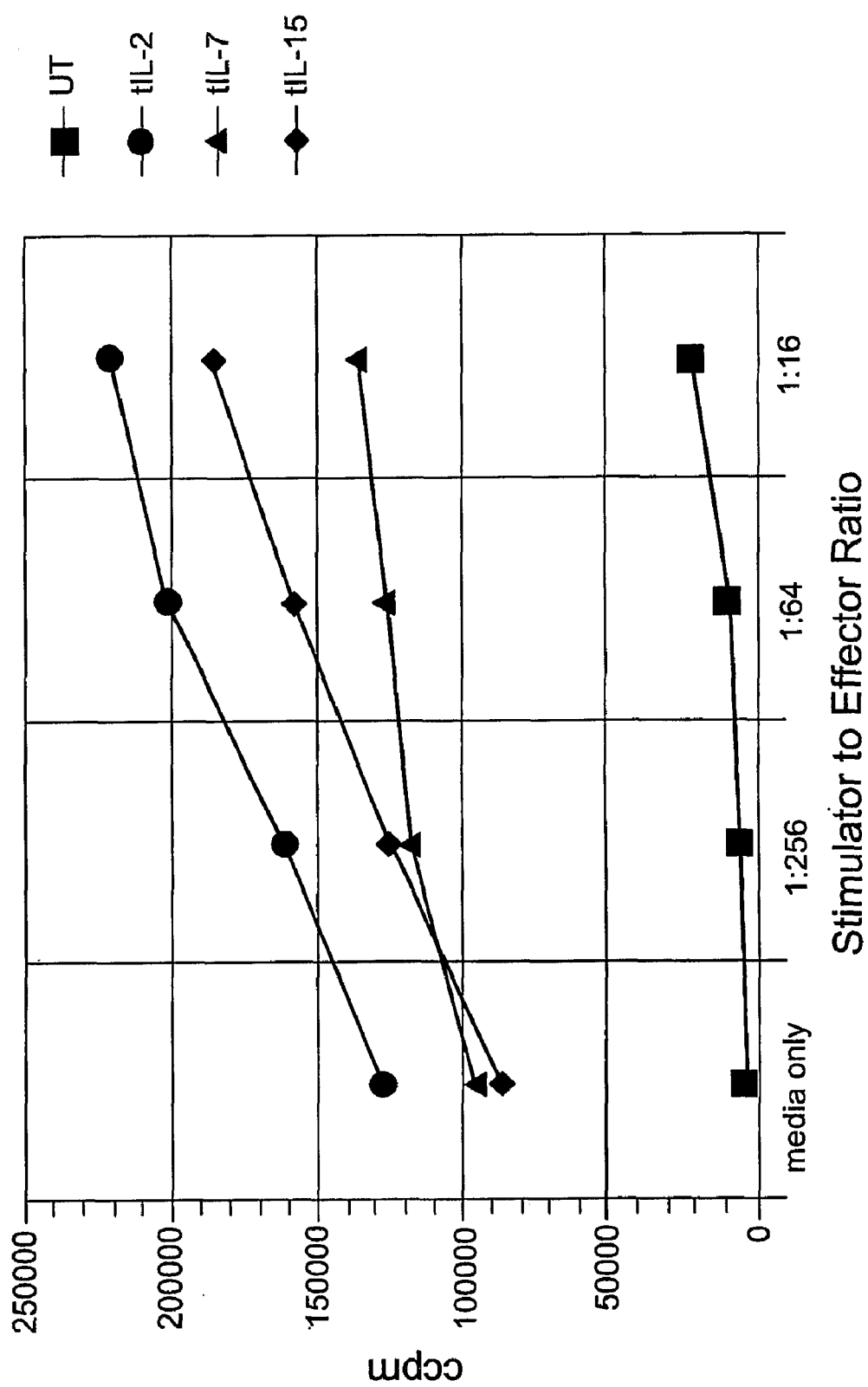
FIG. 29 is a graph of the proliferation (as determined by the uptake of $^3$H-thymidine) of untransduced cells (UT; ■), or cells transduced with a vector encoding IL-2 (●), IL-7 (▲), or IL-15 (●), upon stimulation with different ratios of allogeneic dendritic cells, in accordance with an embodiment of the invention.

PBL transduced with IL-2-, IL-7-, or IL-15-encoding retroviral vectors were co-cultured for 3 days with allogeneic DC and pulsed with $^3$H-thymidine in the last 18 hours of culture. As shown in FIG. 29, the transduced PBL exhibited the ability to proliferate in response to stimulation with allogeneic DC, in the absence of exogenous cytokine, whereas untransduced cells demonstrated very little, if any, ability to proliferate under the same conditions. However, the untransduced cells were able to proliferate in the presence of exogenous IL-2, IL-7, or IL-15 in the media (FIG. 28).

This example demonstrated the ability of PBL's transduced with IL-7 or IL-15 to proliferate in the absence of exogenous cytokine.

Example 22

This example demonstrates a method of constructing a vector encoding IL-15 and comprising a suicide gene and a method of testing for the expression of each gene.

Eight retroviral constructs comprising the codon-optimized or wildtype IL-15 gene and the codon-optimized or wildtype Herpes Simplex Virus (HSV) thymidine kinase (TK) gene were constructed into the pMSGV backbone: pMSGV-wtHSVtk-IRES-CO IL15, pMSGV-wtHSVtk-PGK-CO IL15, pMSGV-wtIL15-PGK-wtHSVtk, pMSGV1-CO-IL-15-IRES-CO—HSV-TK, pMSGV1-wtIL15-IRES-wtHSVtk, pMSGV1ppl-CO IL15-IRES-wtHSVtk, pMSGV1ppl-CO IL15-PGK-CO—HSV TK, and pMSGV1ppl-CO IL15-PGK-wtHSVtk. Specifically, the wild-type or codon-optimized IL-15 were modified by the insertion of wild-type or codon-optimized HSV-TK genes where the expression of the HSV-TK is mediated by either an IRES element or using the PGK promoter. The structure of the vectors is indicated by the name of the vector. For example, the pMSGV-wtHSVtk-IRES-CO IL15 vector has the wild-type HSV-TK gene preceding the IRES element, which precedes the codon-optimized IL-15 gene.

To determine if both IL-15 and HSV TK can be expressed in cells transduced with the vectors, Phoenix Eco retroviral packaging cells are transfected with the eight different suicide gene vectors (and IL-15 vectors without the HSV-TK). The retroviral supernatant is applied to Retronectin coated plates, which are then used to transduce NIH/3T3 cells. Cells are also transduced with the GFP retroviral vector (MSGIN) as a control.

On Day 0, NIH/3T3 cells were plated with serial dilutions of ganciclovir (GCV) (0, 0.001, 0.01, 0.1, 1.0 and 10 µM). On Day 1, the media of these cell cultures were replaced. On Day 2, cell culture supernatants were collected and tested by ELISA for IL-15. Also, live cell numbers were determined by trypan blue exclusion. Cell counts decreased upon increasing doses of GCV for all cells transduced with a vector encoding either codon-optimized or wildtype HSV-TK, whereas cell counts of cells transduced with control vectors, MSGIN, wtIL-15, and CO-IL-15, did not decrease in a GCV dose-dependent manner. Also, the amounts of IL-15 decreased in a GCV dose-dependent manner in cell cultures Of cells transduced with vectors encoding either wildtype of codon-optimized HSV-TK and wildtype or codon-optimized IL-15, whereas no IL-15 was produced by cells transduced with the control vector MSGIN and the amounts of IL-15 did not decrease in a GCV dose-dependent manner for cells transduced with a vector lacking the HSV-TK gene.

To determine whether the IL-15/TK vectors can be expressed by T lymphocytes, PBLs are stimulated with OKT3 and cultured in media containing IL-2. On culture days 2 and 3, the cells are transduced on Retronectin plates pre-coated with retroviral supernatants. The IL-15 vector supernatant is diluted 1:4 and used as a control condition. On culture day 6, a 3-day cytokine production assay is performed, wherein the production of cytokine is assayed by ELISA.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated T lymphocyte expressing at least one recombinant polynucleotide encoding a cytokine that enhances T lymphocyte survival during the contraction phase of an immune response, wherein the recombinant polynucleotide comprises a non-native coding sequence encoding the cytokine and wherein the recombinant polynucleotide comprises SEQ ID NO: 4.

2. The isolated T lymphocyte of claim 1, wherein the T lymphocyte survives in vitro in the absence of an exogenous cytokine for at least 40 days.

3. The isolated T lymphocyte of claim 2, wherein the T lymphocyte survives in vitro in the absence of an exogenous cytokine for at least 180 days.

4. The isolated T lymphocyte of claim 1, wherein the T lymphocyte proliferates in vitro in the absence of an exogenous cytokine.

5. The isolated T lymphocyte of claim 1, wherein the T lymphocyte resists IL-2 withdrawal-induced-apoptosis in vitro in the absence of an exogenous cytokine.

6. The isolated T lymphocyte of claim 1, wherein the T lymphocyte recognizes antigen in vitro in the absence of an exogenous cytokine.

7. The isolated T lymphocyte of claim 1, wherein the non-native coding sequence has undergone codon optimization.

8. The isolated T lymphocyte of claim 7, wherein the non-native coding sequence has 50% or less the predicted free energy of the native coding sequence.

9. The isolated T lymphocyte of claim 1, wherein the recombinant polynucleotide comprises a suicide gene.

10. The isolated T lymphocyte of claim 9, wherein the suicide gene is the Herpes Simplex Virus (HSV) thymidine kinase (TK) gene.

11. The isolated T lymphocyte of claim 1, wherein the T lymphocyte is a tumor infiltrating lymphocyte (TIL).

12. The isolated T lymphocyte of claim 1, wherein the T lymphocyte is a human T lymphocyte.

13. The isolated T lymphocyte of claim 1, wherein the T lymphocyte comprises a receptor specific for an antigen of a medical condition.

14. The isolated T lymphocyte of claim 13, wherein the receptor is an endogenous T cell receptor (TCR) or a recombinant chimeric receptor.

15. The isolated T lymphocyte of claim 13, wherein the medical condition is cancer.

16. The isolated T lymphocyte of claim 15, wherein the cancer is melanoma.

17. A population of cells comprising the T lymphocyte of claim 1.

18. A pharmaceutical composition comprising the isolated T lymphocyte of claim 1, and a pharmaceutically acceptable carrier.

19. A pharmaceutical composition comprising a T lymphocyte, or a population of T lymphocytes, expressing at least one recombinant polynucleotide encoding a cytokine that enhances T lymphocyte survival during the contraction phase of an immune response, wherein the recombinant polynucleotide comprises a codon-optimized coding sequence encoding the cytokine and wherein the recombinant polynucleotide comprises SEQ ID NO: 4, and a pharmaceutically acceptable carrier.

20. A composition comprising T lymphocytes transformed with and expressing at least one recombinant polynucleotide encoding a cytokine that enhances T lymphocyte survival during the contraction phase of the immune response, wherein the recombinant polynucleotide comprises a codon-optimized coding sequence encoding the cytokine and wherein the recombinant polynucleotide comprises SEQ ID NO: 4.

21. An isolated peripheral blood mononuclear cell (PBMC) expressing at least one recombinant polynucleotide encoding a cytokine that enhances PBMC survival during the contraction phase of an immune response, wherein the recombinant polynucleotide comprises a non-native coding sequence encoding the cytokine and wherein the recombinant polynucleotide comprises SEQ ID NO: 4.

* * * * *